(12) United States Patent
Fischer et al.

(10) Patent No.: US 8,247,351 B2
(45) Date of Patent: Aug. 21, 2012

(54) INSECTICIDAL COMPOSITIONS HAVING IMPROVED EFFECT

(75) Inventors: Reiner Fischer, Monheim (DE); Stefan Lehr, Liederbach (DE); Peter Marczok, Köln (DE); Udo Reckmann, Köln (DE); Christian Arnold, Langenfeld (DE); Waltraud Hempel, Liederbach (DE); Erich Sanwald, Kiel (DE); Rolf Pontzen, Leichlingen (DE)

(73) Assignee: Bayer Cropscience AG, Monheim (DE)

( * ) Notice: Subject to any disclaimer, the term of this patent is extended or adjusted under 35 U.S.C. 154(b) by 242 days.

(21) Appl. No.: 12/096,904

(22) PCT Filed: Dec. 11, 2006

(86) PCT No.: PCT/EP2006/011912
§ 371 (c)(1),
(2), (4) Date: Oct. 6, 2008

(87) PCT Pub. No.: WO2007/068428
PCT Pub. Date: Jun. 21, 2007

(65) Prior Publication Data
US 2009/0209513 A1 Aug. 20, 2009

(30) Foreign Application Priority Data
Dec. 13, 2005 (DE) .................. 10 2005 059 469

(51) Int. Cl.
*A01N 43/36* (2006.01)
*A01N 43/38* (2006.01)
*A01N 33/12* (2006.01)
*A01N 59/00* (2006.01)
*A01N 59/26* (2006.01)
*A01N 57/20* (2006.01)

(52) U.S. Cl. ........ 504/128; 504/138; 504/148; 424/601; 424/719; 424/720; 514/75; 514/112; 514/129; 514/134; 514/409; 514/642; 514/946

(58) Field of Classification Search .................. 504/128, 504/138, 148; 424/601, 719, 720; 514/75, 514/112, 129, 134, 409, 642
See application file for complete search history.

(56) References Cited

U.S. PATENT DOCUMENTS

| | | | |
|---|---|---|---|
| 2,842,476 A | 7/1958 | Schreiber | |
| 4,091,006 A | 5/1978 | Durden, Jr. et al. | |
| 4,175,135 A | 11/1979 | Haines | |
| 4,209,432 A | 6/1980 | Roth | |
| 4,209,532 A | 6/1980 | Wheeler | |
| 4,256,657 A | 3/1981 | Wheeler | |
| 4,256,658 A | 3/1981 | Wheeler | |
| 4,256,659 A | 3/1981 | Wheeler | |
| 4,257,858 A | 3/1981 | Wheeler | |
| 4,283,348 A | 8/1981 | Wheeler | |
| 4,303,669 A | 12/1981 | D'Silva | |
| 4,338,122 A | 7/1982 | Wheeler | |
| 4,351,666 A | 9/1982 | Koerwer | |
| 4,409,153 A | 10/1983 | Hodakowski | |
| 4,436,666 A | 3/1984 | Wheeler | |
| 4,526,723 A | 7/1985 | Wheeler et al. | |
| 4,551,547 A | 11/1985 | Wheeler | |
| 4,613,617 A | 9/1986 | Sousa | |
| 4,632,698 A | 12/1986 | Wheeler | |
| 4,659,372 A | 4/1987 | Wheeler | |
| 4,844,734 A | 7/1989 | Iwasaki et al. | |
| 4,888,049 A | 12/1989 | Iwasaki et al. | |
| 4,925,868 A | 5/1990 | Terao et al. | |
| 4,985,063 A | 1/1991 | Fischer et al. | |
| 5,045,560 A | 9/1991 | Fischer et al. | |
| 5,094,681 A | 3/1992 | Kramer et al. | |
| 5,116,836 A | 5/1992 | Fischer et al. | |
| 5,164,179 A | 11/1992 | Hioki et al. | |
| 5,225,434 A | 7/1993 | Bertram et al. | |
| 5,258,527 A | 11/1993 | Krauskopf et al. | |
| 5,262,383 A | 11/1993 | Fischer et al. | |
| 5,298,501 A | 3/1994 | Cummings | |
| 5,332,720 A | 7/1994 | Krueger et al. | |
| 5,393,729 A | 2/1995 | Fischer et al. | |
| 5,462,912 A | 10/1995 | Hioki et al. | |
| 5,462,913 A | 10/1995 | Fischer et al. | |
| 5,494,890 A | 2/1996 | Cederbaum et al. | |
| 5,504,057 A | 4/1996 | Fischer et al. | |
| 5,506,193 A | 4/1996 | Cederbaum et al. | |
| 5,538,937 A | 7/1996 | Hasebe et al. | |
| 5,565,450 A | 10/1996 | Fischer et al. | |
| 5,567,671 A | 10/1996 | Fischer et al. | |

(Continued)

FOREIGN PATENT DOCUMENTS

CA 2 382 432 A1 3/2001

(Continued)

OTHER PUBLICATIONS

Fischer, R. et al., "Spirotetramat (Movento)—discovery, synthesis and physicochemical properties," Bayer CropScience Journal, vol. 61, pp. 127-140 (2008).*
Ziegler et al., "Synthesen von Heterocyclen, 52. Mitt: Ueber Derivate des 2-Phenyl-4-hydroxy-[1,3-thiazinons-(6)]," Monatsch 95, 52 (1964) pp. 147-155.
Ketcham et al., "Synthesis of Heterocycles. 174 (1,2) Substituted Thiazines and Bisthiazinyls from Dithiooxamide and Trichlorophynyl Malonates," J. Heterocycl. Chem. (1973) pp. 223-228.
Sousa et al., "Esters of 3-Hydroxy-2-Arylindones, a New Class of Acaricide," Journal of Economic Entomology, vol. 66, No. 2 (1973) pp. 584-586.
Wheeler, T. "Novel Photochemical Synthesis of 2-Aryl-1,3-cyclohexanediones," J. Org. Chem., vol. 44, No. 26 (1979) pp. 4906-4912.

(Continued)

*Primary Examiner* — John Pak
(74) *Attorney, Agent, or Firm* — Baker Donelson Bearman Caldwell & Berkowitz, PC

(57) ABSTRACT

The present invention concerns boosting the activity of crop protection materials comprising active ingredients from the class of the phenyl-substituted cyclic ketoenols through the addition of ammonium salts and/or phosphonium salts or through the addition of ammonium salts and/or phosphonium salts and penetrants, the corresponding materials, processes for preparing them, and their use in crop protection.

22 Claims, No Drawings

U.S. PATENT DOCUMENTS

| | | | |
|---|---|---|---|
| 5,589,469 A | 12/1996 | Fischer et al. |
| 5,610,122 A | 3/1997 | Fischer et al. |
| 5,622,917 A | 4/1997 | Fischer et al. |
| 5,703,132 A | 12/1997 | Sagenmuller et al. |
| 5,705,476 A | 1/1998 | Hoffarth |
| 5,789,440 A | 8/1998 | Ellsworth et al. |
| 5,792,755 A | 8/1998 | Sagenmuller et al. |
| 5,808,135 A | 9/1998 | Fischer et al. |
| 5,830,825 A | 11/1998 | Fischer et al. |
| 5,830,826 A | 11/1998 | Fischer et al. |
| 5,840,661 A | 11/1998 | Fischer et al. |
| 5,945,444 A | 8/1999 | Fischer et al. |
| 5,960,443 A | 9/1999 | Young et al. |
| 5,977,029 A | 11/1999 | Fischer et al. |
| 5,994,274 A | 11/1999 | Fischer et al. |
| 6,071,937 A | 6/2000 | Bretschneider et al. |
| 6,133,296 A | 10/2000 | Lieb et al. |
| 6,140,358 A | 10/2000 | Lieb et al. |
| 6,172,255 B1 | 1/2001 | Fischer et al. |
| 6,200,932 B1 | 3/2001 | Fischer et al. |
| 6,251,833 B1 | 6/2001 | Erdelen et al. |
| 6,255,342 B1 | 7/2001 | Lieb et al. |
| 6,288,102 B1 | 9/2001 | Hagemann et al. |
| 6,316,486 B1 | 11/2001 | Lieb et al. |
| 6,358,887 B1 | 3/2002 | Fischer et al. |
| 6,410,480 B1 | 6/2002 | Muehlebach et al. |
| 6,451,843 B1 | 9/2002 | Lieb et al. |
| 6,458,965 B1 | 10/2002 | Lieb et al. |
| 6,472,419 B1 | 10/2002 | Fischer et al. |
| 6,515,184 B1 | 2/2003 | Fischer et al. |
| 6,555,499 B1 | 4/2003 | Glock et al. |
| 6,569,810 B1 | 5/2003 | Fischer et al. |
| 6,589,976 B1 | 7/2003 | Fischer et al. |
| 6,602,823 B1 | 8/2003 | Roechling et al. |
| 6,608,211 B1 | 8/2003 | Hagemann et al. |
| 6,645,914 B1 | 11/2003 | Woznica et al. |
| 6,861,391 B1 | 3/2005 | Fischer et al. |
| 6,894,005 B1 | 5/2005 | Maetzke et al. |
| 2001/0004629 A1 | 6/2001 | Lieb et al. |
| 2002/0022575 A1 | 2/2002 | Fischer et al. |
| 2002/0072617 A1 | 6/2002 | Hagemann et al. |
| 2002/0188136 A1 | 12/2002 | Lieb et al. |
| 2003/0045432 A1 | 3/2003 | Fischer et al. |
| 2003/0073851 A1 | 4/2003 | Lieb et al. |
| 2003/0096806 A1 | 5/2003 | Lieb et al. |
| 2003/0171219 A1 | 9/2003 | Lieb et al. |
| 2003/0176464 A1 | 9/2003 | Fischer et al. |
| 2003/0199572 A1 | 10/2003 | Lieb et al. |
| 2003/0216260 A1 | 11/2003 | Ruther et al. |
| 2003/0224939 A1 | 12/2003 | Miles |
| 2003/0228984 A1 | 12/2003 | Hagemann et al. |
| 2004/0019061 A1 | 1/2004 | Fischer et al. |
| 2004/0102516 A1 | 5/2004 | Fischer et al. |
| 2004/0157743 A1 | 8/2004 | Rosenfeldt et al. |
| 2005/0009880 A1 | 1/2005 | Cottrell et al. |
| 2005/0054535 A1 | 3/2005 | Fischer et al. |
| 2005/0096386 A1 | 5/2005 | Cottrell et al. |
| 2005/0164883 A1 | 7/2005 | Maetzke et al. |
| 2005/0221991 A1 | 10/2005 | Wolf et al. |
| 2006/0160847 A1 | 7/2006 | Fischer et al. |
| 2006/0166829 A1 | 7/2006 | Fischer et al. |
| 2006/0166898 A1 | 7/2006 | Chen |
| 2007/0015664 A1 | 1/2007 | Fischer et al. |
| 2007/0032539 A1 | 2/2007 | Himmler |
| 2007/0066488 A1 | 3/2007 | Fischer et al. |
| 2007/0129252 A1 | 6/2007 | Fischer et al. |
| 2007/0225167 A1 | 9/2007 | Fischer et al. |
| 2007/0225170 A1 | 9/2007 | Fischer et al. |
| 2007/0244007 A1 | 10/2007 | Fischer et al. |
| 2007/0275858 A1 | 11/2007 | Fischer et al. |
| 2007/0281860 A1 | 12/2007 | Baur et al. |
| 2007/0298968 A1 | 12/2007 | Bretschneider et al. |
| 2007/0298969 A1 | 12/2007 | Fischer et al. |
| 2008/0081807 A1 | 4/2008 | Lieb et al. |
| 2008/0188371 A1 | 8/2008 | Fischer et al. |
| 2008/0305955 A1 | 12/2008 | Bretschneider et al. |
| 2009/0029858 A1 | 1/2009 | Fischer et al. |
| 2010/0009850 A1 | 1/2010 | Fischer et al. |
| 2010/0174084 A1 | 7/2010 | Fischer et al. |
| 2010/0261934 A1 | 10/2010 | Fischer et al. |

FOREIGN PATENT DOCUMENTS

| | | |
|---|---|---|
| CN | 1 162 071 | 2/1984 |
| DE | 2 361 084 | 12/1972 |
| DE | 28 13 341 A1 | 10/1978 |
| DE | 40 14 420 A1 | 9/1989 |
| EP | 0 036 106 A2 | 9/1981 |
| EP | 0 262 399 A2 | 4/1988 |
| EP | 0 355 599 A1 | 2/1990 |
| EP | 0 377 893 A2 | 7/1990 |
| EP | 0 415 211 A2 | 3/1991 |
| EP | 0 442 073 A2 | 8/1991 |
| EP | 0 442 077 B1 | 8/1991 |
| EP | 0 453 086 A2 | 10/1991 |
| EP | 0 456 063 A2 | 11/1991 |
| EP | 0 508 126 A1 | 10/1992 |
| EP | 0 521 334 A1 | 1/1993 |
| EP | 0 528 156 A1 | 2/1993 |
| EP | 0 588 137 A1 | 3/1994 |
| EP | 0 596 298 A2 | 5/1994 |
| EP | 0 613 884 A2 | 9/1994 |
| EP | 0 613 885 A2 | 9/1994 |
| EP | 0 647 637 A1 | 4/1995 |
| EP | 0 664 081 A2 | 7/1995 |
| EP | 0 668 267 A1 | 8/1995 |
| EP | 0 681 865 A2 | 11/1995 |
| FR | 2 600 494 A1 | 12/1987 |
| GB | 2 266 888 A | 5/1992 |
| JP | 11152273 A | 6/1999 |
| JP | 2000-053670 | 2/2000 |
| WO | 92/16108 A1 | 10/1992 |
| WO | 92/16510 A1 | 10/1992 |
| WO | 94/14785 A1 | 7/1994 |
| WO | 95/01997 A1 | 1/1995 |
| WO | 95/14012 A1 | 5/1995 |
| WO | 95/17817 A1 | 7/1995 |
| WO | 95/20572 A1 | 8/1995 |
| WO | 95/26345 A1 | 10/1995 |
| WO | 95/26954 A1 | 10/1995 |
| WO | 96/01798 A1 | 1/1996 |
| WO | 96/02539 A1 | 2/1996 |
| WO | 96/03366 A1 | 2/1996 |
| WO | 96/11574 A1 | 4/1996 |
| WO | 96/20196 A1 | 7/1996 |
| WO | 96/21652 A1 | 7/1996 |
| WO | 96/25395 A1 | 8/1996 |
| WO | 96/35664 A1 | 11/1996 |
| WO | 97/01535 A1 | 1/1997 |
| WO | 97/02243 A1 | 1/1997 |
| WO | 97/14667 A1 | 4/1997 |
| WO | 97/16436 A1 | 5/1997 |
| WO | 97/19941 A1 | 6/1997 |
| WO | 97/36868 A1 | 10/1997 |
| WO | 97/43275 A2 | 11/1997 |
| WO | 98/05638 A2 | 2/1998 |
| WO | 98/06721 A1 | 2/1998 |
| WO | 98/25928 A1 | 6/1998 |
| WO | 98/35553 A1 | 8/1998 |
| WO | 98/39281 A1 | 9/1998 |
| WO | 99/05638 A1 | 2/1999 |
| WO | 99/16748 A1 | 4/1999 |
| WO | 99/24437 A1 | 5/1999 |
| WO | 99/43649 A1 | 9/1999 |
| WO | 99/47525 A1 | 9/1999 |
| WO | 99/48869 A1 | 9/1999 |
| WO | 99/55673 A1 | 11/1999 |
| WO | 00/35278 A1 | 6/2000 |
| WO | 01/17351 A1 | 3/2001 |
| WO | 01/17352 A1 | 3/2001 |
| WO | 01/17353 A1 | 3/2001 |
| WO | 01/17972 A2 | 3/2001 |
| WO | 01/17973 A2 | 3/2001 |
| WO | 01/23354 A2 | 4/2001 |
| WO | 01/74770 A1 | 10/2001 |
| WO | 01/79204 A1 | 10/2001 |
| WO | 01/98288 A1 | 12/2001 |

| | | |
|---|---|---|
| WO | 02/098230 A2 | 12/2002 |
| WO | 03/013249 A1 | 2/2003 |
| WO | 03/028466 A2 | 4/2003 |
| WO | 03/062244 A1 | 7/2003 |
| WO | 03/099005 A1 | 12/2003 |
| WO | 2004/007448 A1 | 1/2004 |
| WO | 2004/024688 A1 | 3/2004 |
| WO | 2004/065366 A1 | 8/2004 |
| WO | 2004/080962 A1 | 9/2004 |
| WO | 2004/111042 A1 | 12/2004 |
| WO | 2005/005428 A1 | 1/2005 |
| WO | 2005/016873 A2 | 2/2005 |
| WO | 2005/044791 A1 | 5/2005 |
| WO | 2005/044796 A1 | 5/2005 |
| WO | 2005/048710 A1 | 6/2005 |
| WO | 2005/049569 A1 | 6/2005 |
| WO | 2005/066125 A1 | 7/2005 |
| WO | 2005/084435 A2 | 9/2005 |
| WO | 2005/092897 A2 | 10/2005 |
| WO | 2006/000355 A1 | 1/2006 |
| WO | 2006/029799 A1 | 3/2006 |
| WO | 2006/056281 A1 | 6/2006 |
| WO | 2006/056282 A1 | 6/2006 |
| WO | 2006/079079 A1 | 7/2006 |
| WO | 2006/089633 A2 | 8/2006 |

OTHER PUBLICATIONS

Baur et al., "Polydisperse Ethoxylated Fatty Alcohol Surfactants as Accelerators of Cuticular Penetration. 1. Effects of Ethoxy Chain Length and the Size of the Penetrants," Pestic. Sci. vol. 51 (1997) pp. 131-152.

International Search Report, PCT/EP2006/011912, Apr. 18, 2008 (7 pages).

Suzuki et al., "Studies on Antiviral Agents. IV Biological Activity of Tenuazonic Acid Derivatives," Chem. Pharm. Bull. vol. 15 (1987) pp. 1120-1122.

Schmierer et al., "Cyclisierung von N-Acylalanin- and N-Acylglycinestern," Liebigs Ann. Chem. (1985) pp. 1095-1098.

Campbell et al., "Synthesis of (E)- and (Z)-Pulvinones," J. Chem. Soc. Perkin Trans. (1985) pp. 1567-1576.

Chirazi et al., "Syntheses of Heterocycles, 184. The Synthesis of Kawalactone Derivatives," Arch. Pharm, (1975) pp. 558-564.

Boltze et al., "Zur Synthese 3-substituierter 4-Hydroxy-pyrone-(2), I," Chem. Ber. vol. 91 (1958) pp. 2849-2853.

* cited by examiner

INSECTICIDAL COMPOSITIONS HAVING IMPROVED EFFECT

CROSS REFERENCE TO RELATED APPLICATIONS

This is a §371 National Stage Application of International Application No. PCT/EP2006/011912, filed Dec. 11, 2006, which claims priority to German Application No. 10 2005 059 469.7, filed Dec. 13, 2005.

BACKGROUND OF THE INVENTION

1. Field of the Invention

The present invention concerns boosting the activity of crop protection materials comprising inhibitors of fatty acid biosynthesis, especially phenyl-substituted cyclic ketoenols, through the addition of ammonium salts or phosphonium salts and, if desired, penetrants, the corresponding materials, processes for preparing them, and their use in crop protection, in particular, as insecticides and/or acaricides.

2. Description of Related Art

For 3-acylpyrrolidine-2,4-diones pharmaceutical properties have already been described (S. Suzuki et al. Chem. Pharm. Bull. 15 1120 (1967)). Additionally N-phenylpyrrolidine-2,4-diones have been synthesized, by R. Schmierer and H. Mildenberger (Liebigs Ann. Chem. 1985, 1095). No biological activity has been described for these compounds.

EP-A-0 262 399 and GB-A-2 266 888 disclose similarly structured compounds (3-arylpyrrolidine-2,4-diones) for which, however, no herbicidal, insecticidal or acaricidal activity has been made known. Compounds known with a herbicidal, insecticidal or acaricidal activity include unsubstituted, bicyclic 3-arylpyrrolidine-2,4-dione derivatives (EP-A-355 599, EP-A-415 211 and JP-A-12-053 670) and also substituted monocyclic 3-arylpyrrolidine-2,4-dione derivatives (EP-A-377 893 and EP-A-442 077).

Additionally known are polycyclic 3-arylpyrrolidine-2,4-dione derivatives (EP-A-442 073) and also 1H-arylpyrrolidinedione derivatives (EP-A-456 063, EP-A-521 334, EP-A-596 298, EP-A-613 884, EP-A-613 885, WO 95/01 997, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/16748, WO 99/24437, WO 99/43649, WO 99/48869 and WO 99/55673, WO 01/17972, WO 01/23354, WO 01/74770, WO 03/013249, WO 04/007448, WO 04/024688, WO 04/065366, WO 04/080962, WO 04/111042, WO 05/044791, WO 05/044796, WO 05/048710, WO 05/049569, WO 05/066125, WO 05/092897, WO 06/000355, WO 06/029799, WO 06/056281, WO 06/056282, WO 06/089633).

It is known that certain substituted $\Delta^3$-dihydrofuran-2-one derivatives possess herbicidal properties (cf. DE-A-4 014 420). The synthesis of the tetronic acid derivatives used as starting compounds (such as 3-(2-methylphenyl)-4-hydroxy-5-(4-fluorophenyl)-$\Delta^3$-dihydrofuran-2-one) is likewise described in DE-A-4 014 420. Similarly structured compounds, without a report of an insecticidal and/or acaricidal activity, are known from the publication by Campbell et al., J. Chem. Soc., Perkin Trans. 1, 1985, (8) 1567-76. Moreover, 3-aryl-$\Delta^3$-dihydrofuranone derivatives having herbicidal, acaricidal and insecticidal properties are known from EP-A-528 156, EP-A-0 647 637, WO 95/26 345, WO 96/20 196, WO 96/25 395, WO 96/35 664, WO 97/01 535, WO 97/02 243, WO 97/36 868, WO 98/05638, WO 98/25928, WO 99/16748, WO 99/43649, WO 99/48869, WO 99/55673, WO 01/17972, WO 01/23354 and WO 01/74770, WO 03/013 249, WO 04/024 688, WO 04/080 962, WO 04/111 042, WO 05/092897, WO 06/000355, WO 06/029799 and WO 06/089633. As well 3-aryl-$\Delta^3$-dihydrothiophene-one derivatives are known (WO 95/26 345, 96/25 395, WO 97/01 535, WO 97/02 243, WO 97/36 868, WO 98/05638, WO 98/25928, WO 99/16748, WO 99/43649, WO 99/48869, WO 99/55673, WO 01/17972, WO 01/23354, WO 01/74770, WO 03/013249, WO 04/080 962, WO 04/111 042, WO 05/092897, WO 06/029799).

Certain phenylpyrone derivatives unsubstituted in the phenyl ring have already been disclosed (cf. A. M. Chirazi, T. Kappe and E. Ziegler, Arch. Pharm. 309, 558 (1976) and K.-H. Boltze and K. Heidenbluth, Chem. Ber. 91, 2849), no possible usefulness as pesticides being reported for these compounds. Phenylpyrone derivatives substituted in the phenyl ring and having herbicidal, acaricidal and insecticidal properties are described in EP-A-588 137, WO 96/25 395, WO 96/35 664, WO 97/01 535, WO 97/02 243, WO 97/16 436, WO 97/19 941, WO 97/36 868, WO 98/05638, WO 99/43649, WO 99/48869, WO 99/55673, WO 01/17972, WO 01/74770, WO 03/013249, WO 04/080 962, WO 04/111 042, WO 05/092897 and WO 06/029799.

Certain 5-phenyl-1,3-thiazine derivatives unsubstituted in the phenyl ring have already been disclosed (cf. E. Ziegler and E. Steiner, Monatsh. 95, 147 (1964), R. Ketcham, T. Kappe and E. Ziegler, J. Heterocycl. Chem. 10, 223 (1973)), no possible application as pesticides being reported for these compounds. 5-Phenyl-1,3-thiazine derivatives substituted in the phenyl ring and having a herbicidal, acaricidal and insecticidal activity are described in WO 94/14 785, WO 96/02 539, WO 96/35 664, WO 97/01 535, WO 97/02 243, WO 97/02 243, WO 97/36 868, WO 99/05638, WO 99/43649, WO 99/48869, WO 99/55673, WO 01/17972, WO 01/74770, WO 03/013249, WO 04/080 962, WO 04/111 042, WO 05/092897 and WO 06/029799.

It is known that certain substituted 2-arylcyclopentanediones have herbicidal, insecticidal and acaricidal properties (cf. e.g. U.S. Pat. Nos. 4,283,348; 4,338,122; 4,436,666; 4,526,723; 4,551,547; 4,632,698; WO 96/01 798; WO 96/03 366, WO 97/14 667 and also WO 98/39281, WO 99/43649, WO 99/48869, WO 99/55673, WO 01/17972, WO 01/74770, WO 03/013249, WO 04/080 962, WO 04/111 042, WO 05/092897 and WO 06/029799). Moreover, similarly substituted compounds are known: 3-hydroxy-5,5-dimethyl-2-phenylcyclopent-2-en-1-one, from the publication by Micklefield et al., Tetrahedron, (1992), 7519-26, and the natural substance Involutin, (−)-cis-5-(3,4-dihydroxyphenyl)-3,4-dihydroxy-2-(4-hydroxyphenyl)cyclopent-2-en-one, from the publication by Edwards et al., J. Chem. Soc. S, (1967), 405-9. No insecticidal or acaricidal activity is described. Furthermore, 2-(2,4,6-trimethylphenyl)-1,3-indanedione is known from the publication J. Economic Entomology, 66, (1973), 584 and from the laid-open specification DE-A 2 361 084, with reports of herbicidal and acaricidal activities.

It is known that certain substituted 2-arylcyclohexanediones possess herbicidal, insecticidal and acaricidal properties (U.S. Pat. Nos. 4,175,135, 4,209,432, 4,256,657, 4,256,658, 4,256,659, 4,257,858, 4,283,348, 4,303,669, 4,351,666, 4,409,153, 4,436,666, 4,526,723, 4,613,617, 4,659,372, DE-A 2 813 341, and also Wheeler, T. N., J. Org. Chem. 44, 4906 (1979)), WO 99/43649, WO 99/48869, WO 99/55673, WO 01/17972, WO 01/74770, WO 03/013249, WO 04/080 962, WO 04/111 042, WO 05/092897 and WO 06/029799).

It is known that certain substituted 4-arylpyrazolidine-3,5-diones possess acaricidal, insecticidal and herbicidal properties (cf. e.g. WO 92/16 510, EP-A-508 126, WO 96/11 574, WO 96/21 652, WO 99/47525, WO 01/17351, WO 01/17352, WO 01/17353, WO 01/17972, WO 01/17973, WO 03/028 466, WO 03/062 244, WO 04/080 962, WO 04/111 042, WO 05/005428, WO 05/016873, WO 05/092897 and WO 06/029799).

It is known that certain tetrahydropyridones possess herbicidal properties (JP 0832530). Moreover, specific 4-hydroxytetrahydropyridones with acaricidal, insecticidal and herbicidal properties are known (JP 11152273). Furthermore, 4-hydroxytetrahydropyridones have become known as pesticides and herbicides, in WO 01/79204.

It is known that certain 5,6-dihydropyrone derivatives have antiviral properties as protease inhibitors (WO 95/14012). Moreover, 4-phenyl-6-(2-phenethyl)-5,6-dihydropyrone is known from the synthesis of kavalactone derivatives (Kappe et al., Arch. Pharm. 309, 558-564 (1976)). Moreover, 5,6-dihydropyrone derivatives are known as intermediates (White, J. D., Brenner, J. B., Deinsdale, M. J., J. Amer. Chem. Soc. 93, 281-282 (1971)). 3-Phenyl-5,6-dihydropyrone derivatives with applications in crop protection are described in WO 01/98288.

All of the active ingredients present in the materials of the invention are already known and can be prepared by methods described in the prior art (see references cited above). Their activity is good, but not always entirely satisfactory, particularly at low application rates and concentrations. Moreover, the plant tolerance of these compounds is not always sufficient. There is therefore a need for a boost in activity of the crop protection materials comprising the compounds.

Descriptions have already been given in the literature to the effect that the activity of various active ingredients can be boosted through addition of ammonium salts. The salts in question, however, are salts with a detergent effect (e.g. WO 95/017817) and/or salts having relatively long alkyl and/or aryl substituents, which have a permeabilizing effect or which increase the solubility of the active ingredient (e.g. EP-A 0 453 086, EP-A 0 664 081, FR-A 2 600 494, U.S. Pat. No. 4,844,734, U.S. Pat. No. 5,462,912, U.S. Pat. No. 5,538,937, US-A 03/0224939, US-A 05/0009880, US-A 05/0096386). Furthermore, the prior art describes the activity only for certain active ingredients and/or certain applications of the materials in question. In still more cases, the salts in question are sulphonic acid salts in whch the acids themselves have a paralysing effect on insects (US 2,842,476). A boost in activity through ammonium sulphate, for example, is described for the herbicides glyphosate and phosphinothricin, for example (U.S. Pat. No. 6,645,914, EP-A2 0 036 106). A corresponding activity in insecticides is neither disclosed nor suggested by this prior art.

As well, the use of ammonium sulphate as a formulating assistant has been described for certain active ingredients and applications (WO 92/16108), but it is used there for the purpose of stabilizing the formulation, not for boosting activity.

SUMMARY OF THE INVENTION

It has now been found, entirely surprisingly, that the activity of insecticides and/or acaricides from the class of the phenyl-substituted cyclic ketoenols can be boosted significantly through the addition of ammonium salts or phosphonium salts to the as-used solution or through the incorporation of these salts into a formulation comprising phenyl-substituted cyclic ketoenols. The present invention provides, therefore, for the use of ammonium salts or phosphonium salts to boost the activity of crop protection materials which comprise insecticidally and/or acaricidally active phenyl-substituted cyclic ketoenols as active ingredient. The invention likewise provides materials which comprise insecticidally and/or acaricidally active phenyl-substituted cyclic ketoenols and activity-boosting ammonium salts or phosphonium salts, specifically including not only formulated active ingredients but also application-ready materials (spray liquors). The invention further provides, finally, for the use of these materials for controlling parasitic insects and/or spider mites.

Active ingredients of the invention from the class of the phenyl-substituted cyclic ketoenols whose activity can be boosted through the addition of ammonium salts or phosphonium salts to the formulated or application-ready active-ingredient preparations are defined by formula (I)

in which

W is hydrogen, alkyl, alkenyl, alkynyl, halogen, alkoxy, haloalkyl, haloalkoxy or cyano, X is halogen, alkyl, alkenyl, alkynyl, alkoxy, alkoxy-alkoxy, haloalkyl, haloalkoxy or cyano, Y is hydrogen, halogen, alkyl, alkenyl, alkynyl, alkoxy, cyano, haloalkyl, haloalkoxy or in each case optionally substituted phenyl or hetaryl, Z is hydrogen, halogen, alkyl, haloalkyl, cyano, alkoxy or haloalkoxy, CKE is one of the groups

-continued

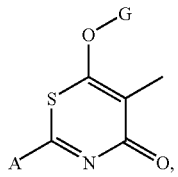
(5)

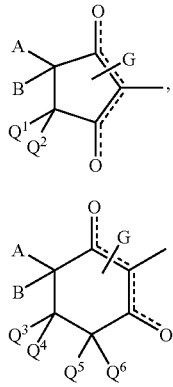
(6)

(7)

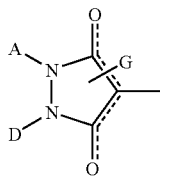
(8)

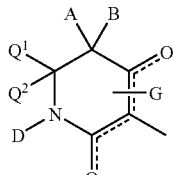
(9)
or

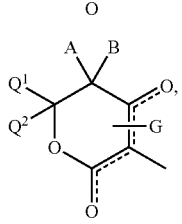
(10)

in which
A is hydrogen, in each case optionally halogen-substituted alkyl, alkenyl, alkoxyalkyl, alkylthioalkyl, saturated or unsaturated, optionally substituted cycloalkyl in which optionally at least one ring atom is replaced by a heteroatom, or in each case optionally halogen-, alkyl-, haloalkyl-, alkoxy-, haloalkoxy-, cyano- or nitro-substituted aryl, arylalkyl or hetaryl,
B is hydrogen, alkyl or alkoxyalkyl, or
A and B, together with the carbon atom to which they are attached, are a saturated or unsaturated, unsubstituted or substituted ring optionally containing at least one heteroatom,
D is hydrogen or an optionally substituted radical from the series alkyl, alkenyl, alkynyl, alkoxyalkyl, saturated or unsaturated cycloalkyl in which optionally one or more ring members are replaced by heteroatoms, or is arylalkyl, aryl, hetarylalkyl or hetaryl, or
A and D, together with the atoms to which they are attached, are a saturated or unsaturated ring which optionally contains at least one (in the case of CKE=8 one further) heteroatom and is substituted or unsubstituted in the A,D moiety, or
A and $Q^1$ together are alkenediyl or alkanediyl optionally substituted by hydroxyl or by in each case optionally substituted alkyl, alkoxy, alkylthio, cycloalkyl, benzyloxy or aryl, or
D and $Q^1$, together with the atoms to which they are attached, are a saturated or unsaturated ring which optionally contains at least one heteroatom and is substituted or unsubstituted in the D, $Q^1$ moiety,
$Q^1$ is hydrogen, alkyl, alkoxyalkyl, optionally substituted cycloalkyl (in which optionally one methylene group is replaced by oxygen or sulphur) or optionally substituted phenyl,
$Q^2$, $Q^4$, $Q^5$ and $Q^6$ independently of one another are hydrogen or alkyl,
$Q^3$ is hydrogen, is optionally substituted alkyl, alkoxyalkyl, alkylthioalkyl, optionally substituted cycloalkyl (in which optionally one methylene group is replaced by oxygen or sulphur) or optionally substituted phenyl, or
$Q^1$ and $Q^2$, together with the carbon atom to which they are attached, are a substituted or unsubstituted ring optionally containing a heteroatom, or
$Q^3$ and $Q^4$, together with the carbon atom to which they are attached, are a saturated or unsaturated, unsubstituted or substituted ring optionally containing a heteroatom,
G is hydrogen (a) or is one of the groups

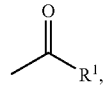
(b)

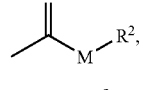
(c)

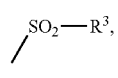
(d)

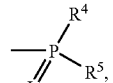
(e)

E or
(f)

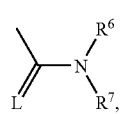
(g)

in which
E is one metal ion equivalent or an ammonium ion,
L is oxygen or sulphur,
M is oxygen or sulphur,
$R^1$ is in each case optionally halogen-substituted alkyl, alkenyl, alkoxyalkyl, alkylthioalkyl, polyalkoxyalkyl or optionally halogen-, alkyl- or alkoxy-substituted cycloalkyl, which may be interrupted by at least one heteroatom, or is in each case optionally substituted phenyl, phenylalkyl, hetaryl, phenoxyalkyl or hetaryloxyalkyl,
$R^2$ is in each case optionally halogen-substituted alkyl, alkenyl, alkoxyalkyl, polyalkoxyalkyl or is in each case optionally substituted cycloalkyl, phenyl or benzyl, $R^3$, $R^4$ and $R^5$ independently of one another are in each case optionally halogen-substituted alkyl, alkoxy, alkylamino, dialkylamino, alkylthio, alkenylthio, cycloalkylthio or are in each case optionally substituted phenyl, benzyl, phenoxy or phenylthio, $R^6$ and $R^7$ independently of one another are hydrogen, in each case optionally halogen-substituted alkyl, cycloalkyl, alkenyl, alkoxy, alkoxyalkyl, are optionally substituted phenyl, are optionally substituted benzyl, or, together with the N atom to which they are attached, are a ring which is optionally interrupted by oxygen or sulphur.

DETAILED DESCRIPTION OF A PREFERRED EMBODIMENT

Depending on factors including the nature of the substituents, the compounds of formula (I) may be present in the form of geometrical and/or optical isomers or isomer mixtures, in different compositions, which can optionally be separated in a customary way. Not only the pure isomers but also the isomer mixtures can be used in materials of the invention and can be boosted in their activity through ammonium salts or phosphonium salts of the invention. Reference below is always, for the sake of simplicity to compounds of the formula (I), although what are meant are not only the pure compounds but also, where appropriate, mixtures containing different fractions of isomeric compounds.

Including the definitions (1) to (10) of the group CKE produces the following principal structures (I-1) to (I-10):

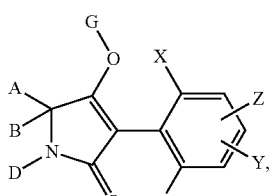
(I-1)

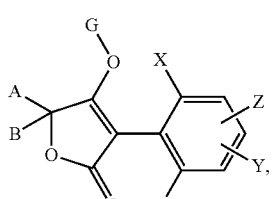
(I-2)

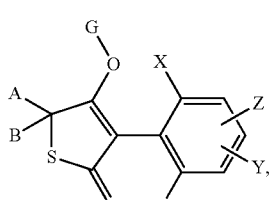
(I-3)

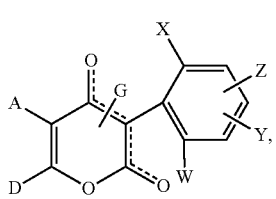
(I-4)

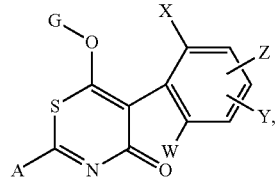
(I-5)

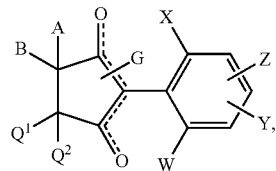
(I-6)

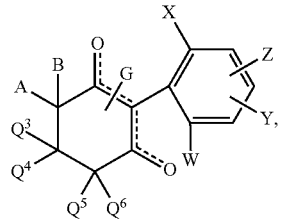
(I-7)

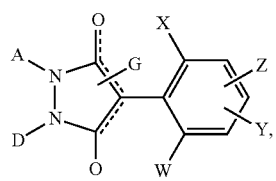
(I-8)

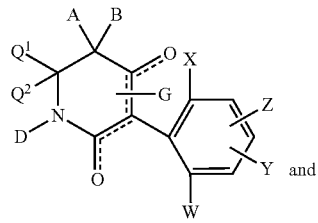
(I-9) and

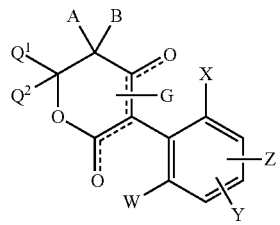
(I-10)

in which
A, B, D, G, $Q^1$, $Q^2$, $Q^3$, $Q^4$, $Q^5$, $Q^6$, W, X, Y and Z are as defined above.

Including the various definitions (a), (b), (c), (d), (e), (f) and (g) of the group G produces the following principal structures (I-1-a) to (I-1-g) if CKE is the group (1):

(I-1-a):
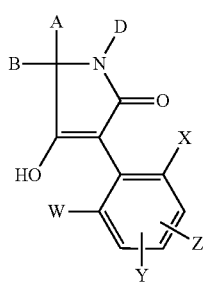
(I-1-b):
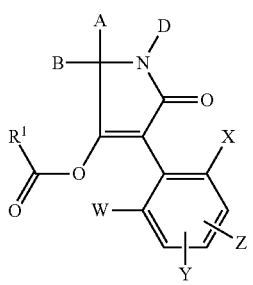
(I-1-c):
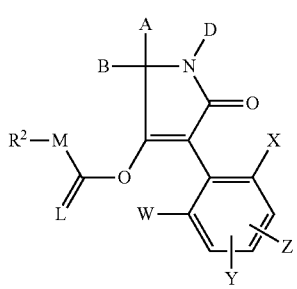
(I-1-d):
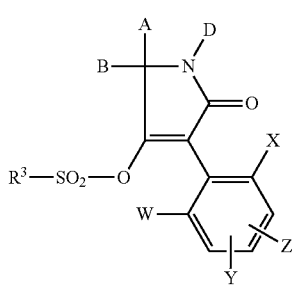
(I-1-e):
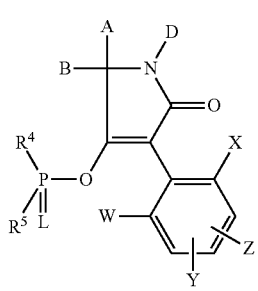
(I-1-f):
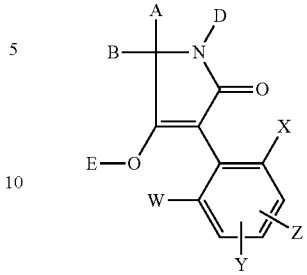
(I-1-g):
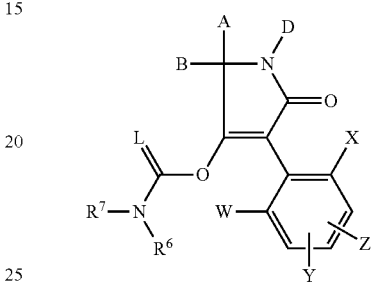
in which
A, B, D, E, L, M, W, X, Y, Z, $R^1$, $R^2$, $R^3$, $R^4$, $R^5$, $R^6$ and $R^7$ are as defined above.
Including the various definitions (a), (b), (c), (d), (e), (f) and (g) of the group G produces the following principal structures (I-2-a) to (I-2-g) if CKE is the group (2):
(I-2-a):
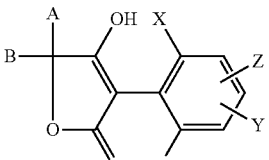
(I-2-b):
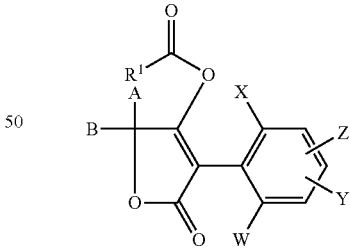
(I-2-c):
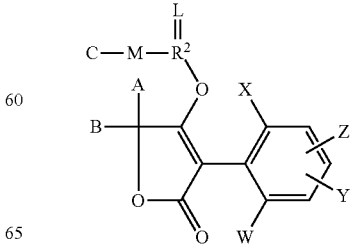

(I-2-d):
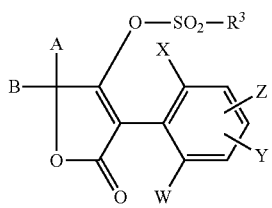
(I-2-e):
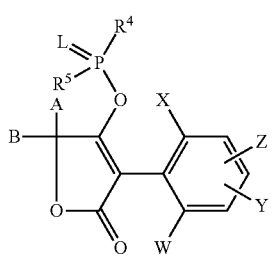
(I-2-f):
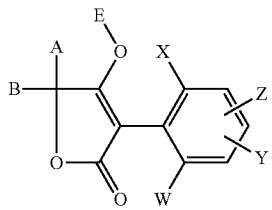
(I-2-g):
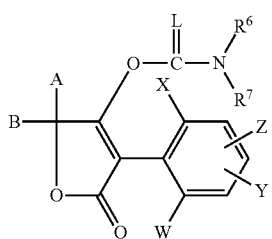
in which
A, B, E, L, M, W, X, Y, Z, $R^1$, $R^2$, $R^3$, $R^4$, $R^5$, $R^6$ and $R^7$ are as defined above.
Including the various definitions (a), (b), (c), (d), (e), (f) and (g) of the group G produces the following principal structures (I-3-a) to (I-3-g) if CKE is the group (3):
(I-3-a):
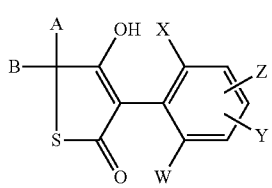
(I-3-b):
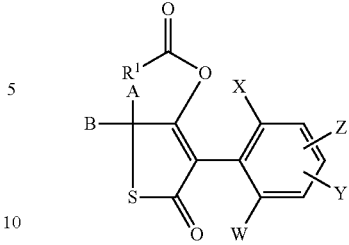
(I-3-c):
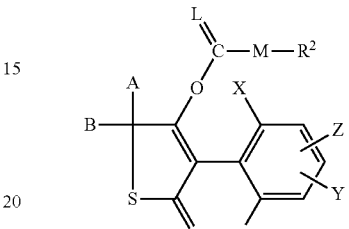
(I-3-d):
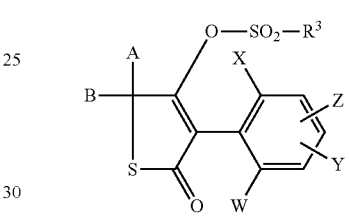
(I-3-e):
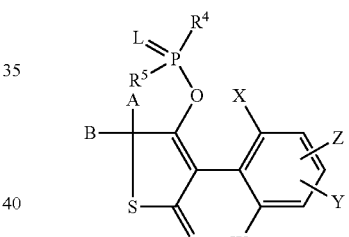
(I-3-f):
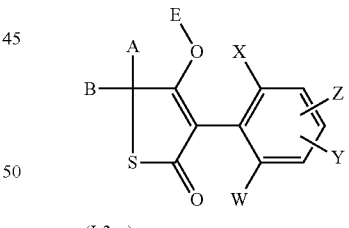
(I-3-g):
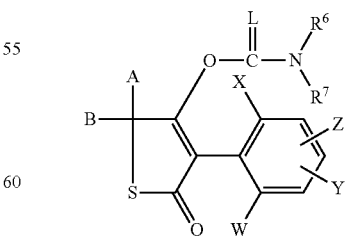
in which
A, B, E, L, M, W, X, Y, Z, $R^1$, $R^2$, $R^3$, $R^4$, $R^5$, $R^6$ and $R^7$ are as defined above.

Depending on the position of the substituent G the compounds of the formula (I-4) may be present in the two isomeric forms of the formulae (I-4-A) and (I-4-B)

(I-4-A)

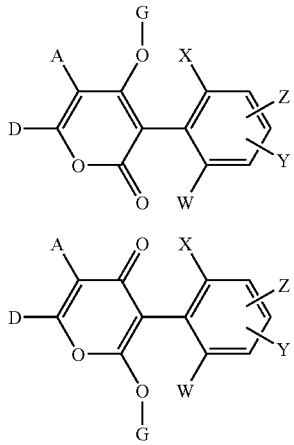

(I-4-B)

which the dashed line in the formula (I-4) is intended to express.

The compounds of the formula (I-4-A) and (I-4-B) may be present both as mixtures and in the form of their pure isomers. Mixtures of the compounds of the formulae (I-4-A) and (I-4-B) can be separated where appropriate in conventional manner by means of physical methods, such as by chromatographic methods, for example.

For reasons of greater clarity in each case only one of the possible isomers is set out below. This does not rule out the possibility of the compounds being present where appropriate in the form of the isomer mixtures or in the respective other isomeric form.

Including the various definitions (a), (b), (c), (d), (e), (f) and (g) of the group G produces the following principal structures (I-4-a) to (I-4-g) if CKE is the group (4):

(I-4-a):

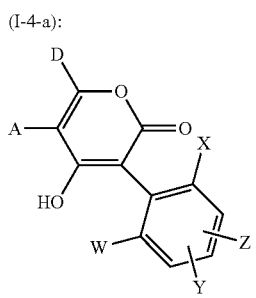

(I-4-b):

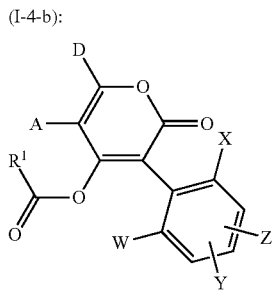

-continued (I-4-c):

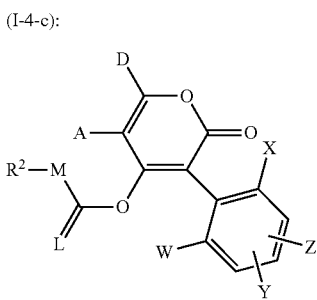

(I-4-d):

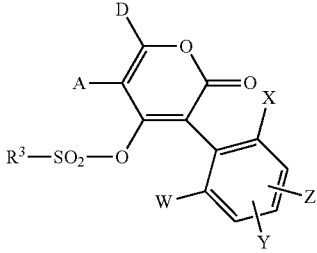

(I-4-e):

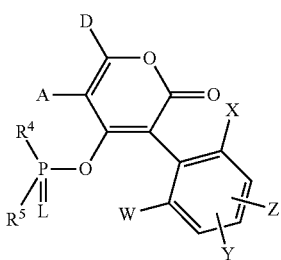

(I-4-f):

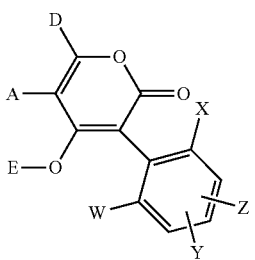

(I-4-g):

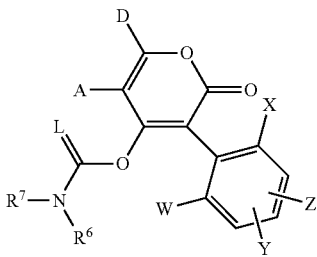

in which

A, D, E, L, M, W, X, Y, Z, $R^1$, $R^2$, $R^3$, $R^4$, $R^5$, $R^6$ and $R^7$ are as defined above.

Including the various definitions (a), (b), (c), (d), (e), (f) and (g) of the group G produces the following principal structures (I-5-a) to (I-5-g) if CKE is the group (5):

(I-5-a):
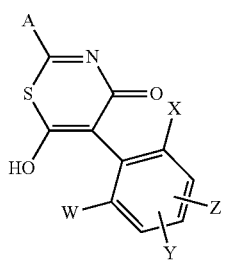

(I-5-b):
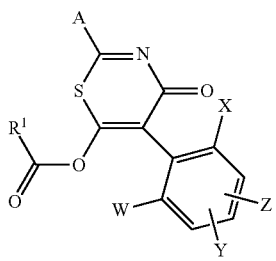

(I-5-c):
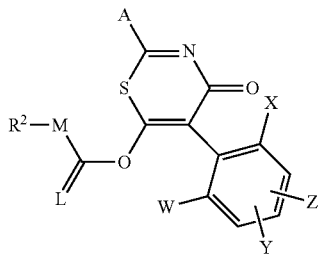

(I-5-d):
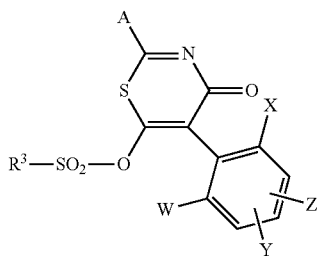

(I-5-e):
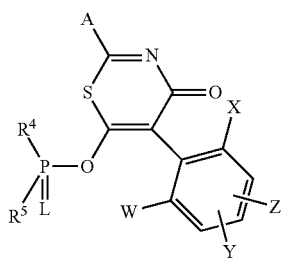

(I-5-f):
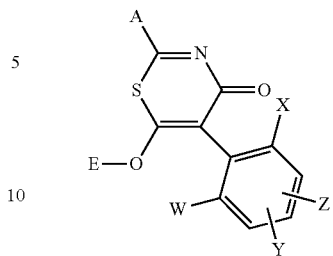

(I-5-g):
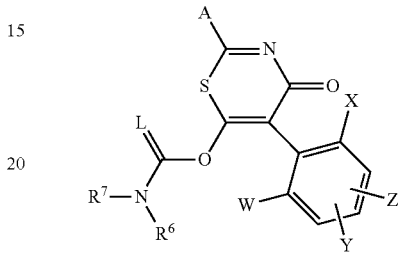

in which
A, E, L, M, W, X, Y, Z, $R^1$, $R^2$, $R^3$, $R^4$, $R^5$, $R^6$ and $R^7$ are as defined above.

Depending on the position of the substituent G the compounds of the formula (I-6) may be present in the two isomeric forms of the formulae (I-6-A) and (I-6-B)

(I-6-A)
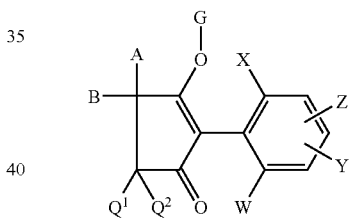

(I-6-B)
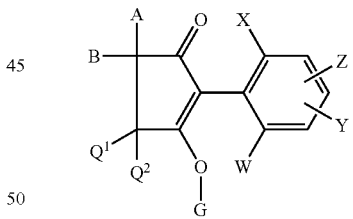

which the dashed line in the formula (I) is intended to express.

The compounds of the formulae (I-6-A) and (I-6-B) may be present both as mixtures and in the form of their pure isomers. Mixtures of the compounds of the formulae (I-6-A) and (I-6-B) can be separated where appropriate by means of physical methods, such as by chromatographic methods, for example.

For reasons of greater clarity in each case only one of the possible isomers is set out below. This does not rule out the possibility of the compounds being present where appropriate in the form of the isomer mixtures or in the respective other isomeric form.

Including the various definitions (a), (b), (c), (d), (e), (f) and (g) of the group G produces the following principal structures (I-6-a) to (I-6-g):

(I-6-a):
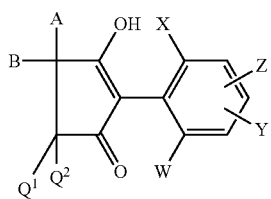

(I-6-b):
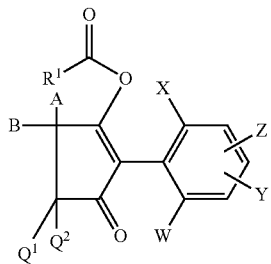

(I-6-c):
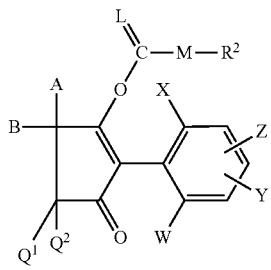

(I-6-d):
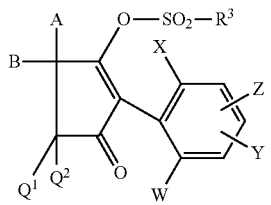

(I-6-e):
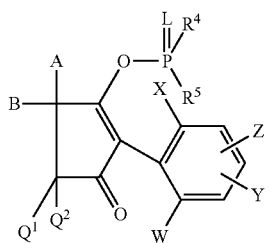

(I-6-f):
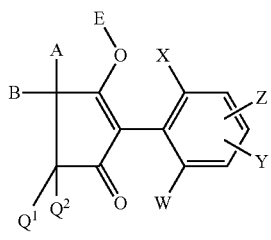

(I-6-g):
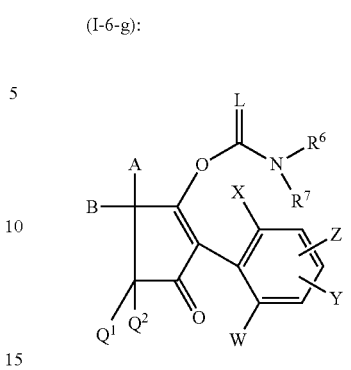

in which

A, B, $Q^1$, $Q^2$, E, L, M, W, X, Y, Z, $R^1$, $R^2$, $R^3$, $R^4$, $R^5$, $R^6$ and $R^7$ are as defined above.

Depending on the position of the substituent G the compounds of the formula (I-7) may be present in the two isomeric forms of the formulae (I-7-A) and (I-7-B) which the dashed line in the formula (I-7) is intended to express:

(I-7-A)
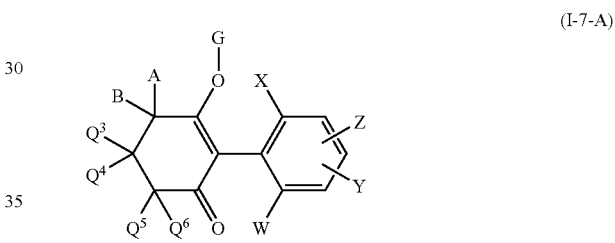

(I-7-B)
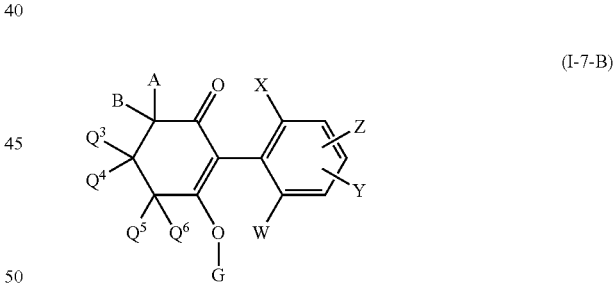

The compounds of the formulae (I-7-A) and (I-7-B) may be present both as mixtures and in the form of their pure isomers. Mixtures of the compounds of the formulae (I-7-A) and (I-7-B) can be separated where appropriate by means of physical methods, such as by chromatographic methods, for example.

For reasons of greater clarity in each case only one of the possible isomers is set out below. This does not rule out the possibility of the relevant compound being present where appropriate as isomer mixtures or in the respective other isomeric form.

Including the various definitions (a), (b), (c), (d), (e), (f) and (g) of the group G produces the following principal structures (I-7-a) to (I-7-g):

(I-7-a):

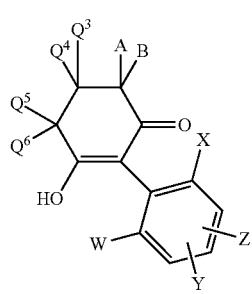

(I-7-b):

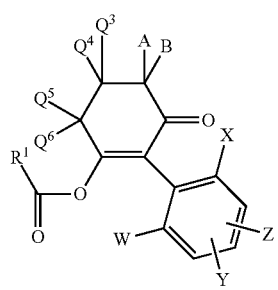

(I-7-c):

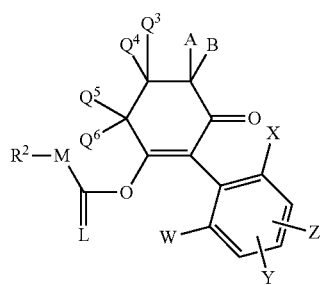

(I-7-d):

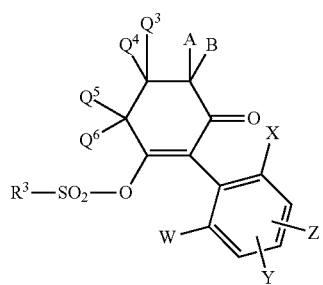

(I-7-e):

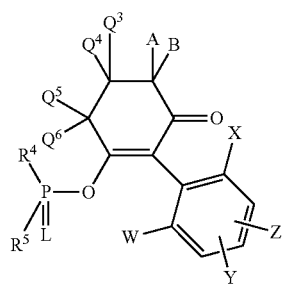

(I-7-f):

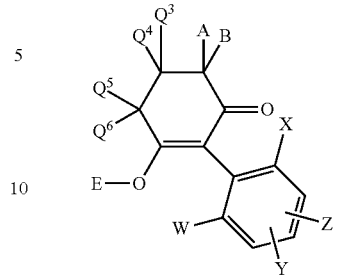

(I-7-g):

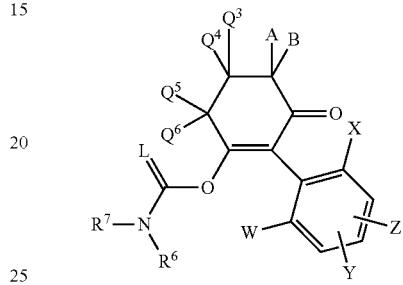

in which
A, B, E, L, M, $Q^3$, $Q^4$, $Q^5$, $Q^6$, W, X, Y, Z, $R^1$, $R^2$, $R^3$, $R^4$, $R^5$, $R^6$ and $R^7$ are as defined above.

Depending on the position of the substituent G the compounds of the formula (I-8) can be present in the two isomeric formulae (I-8-A) and (I-8-B)

(I-8-A)

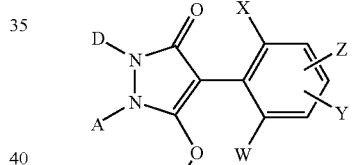

(I-8-B)

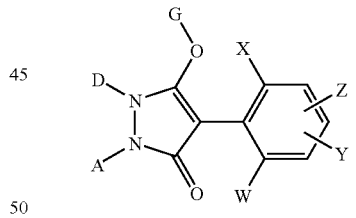

which the dashed line in the formulae (I-8) is intended to express.

The compounds of the formulae (I-8-A) and (I-8-B) may be present both as mixtures and in the form of their pure isomers. Mixtures of the compounds of the formulae (I-8-A) and (I-8-B) can be separated where appropriate in conventional manner by means of physical methods, such as by chromatographic methods, for example.

For reasons of greater clarity in each case only one of the possible isomers is set out below. This does not rule out the possibility of the compounds being present where appropriate in the form of the isomer mixtures or in the respective other isomeric form.

Including the various definitions (a), (b), (c), (d), (e), (f) and (g) of the group G produces the following principal structures (I-8-a) to (I-8-g) if Het is the group (8):

(I-8-a): 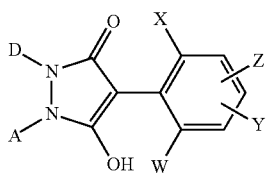

(I-8-b): 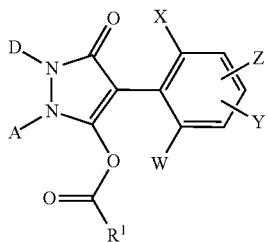

(I-8-c): 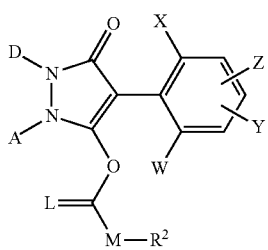

(I-8-d): 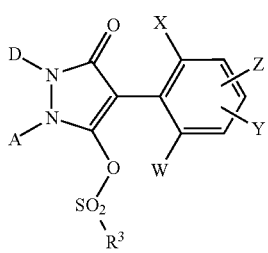

(I-8-e): 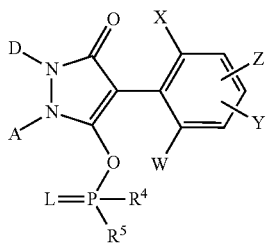

(I-8-f): 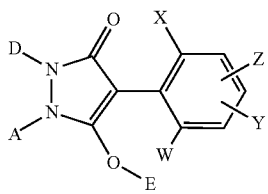

(I-8-g): 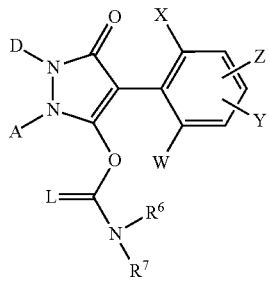

in which
A, D, E, L, M, W, X, Y, Z, $R^1$, $R^2$, $R^3$, $R^4$, $R^5$, $R^6$ and $R^7$ are as defined above.

Depending on the position of the substituent G the compounds of the formulae (I-9) may be present in the two isomeric forms of the formulae (I-9-A) and (I-9-B) which the dashed line in the formula (I-9) is intended to express.

(I-9-A)
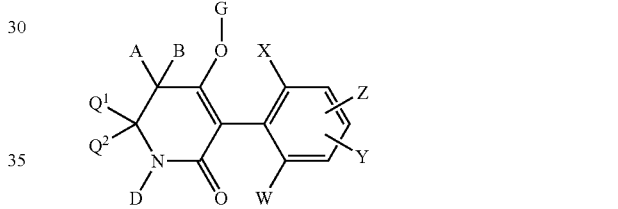

(I-9-B)
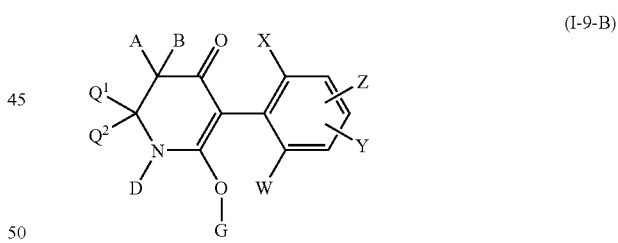

The compounds of the formula (I-9-A) and (I-9-B) may be present both as mixtures and in the form of their pure isomers. Mixtures of the compounds of the formulae (I-9-A) and (I-9-B) can be separated where appropriate in conventional manner by means of physical methods, such as by chromatographic methods, for example.

For reasons of greater clarity in each case only one of the possible isomers is set out below. This does not rule out the possibility of the compounds being present where appropriate in the form of the isomer mixtures or in the respective other isomeric form.

Including the various definitions (a), (b), (c), (d), (e), (f) and (g) of the group G produces the following principal structures (I-9-a) to (I-9-g) if CKE is the group (9):

(I-9-a): 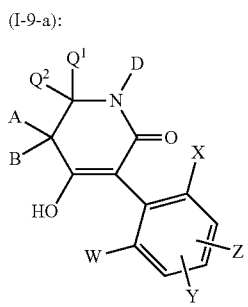

(I-9-b): 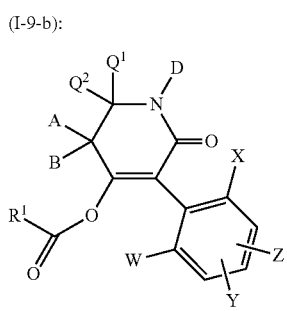

(I-9-c): 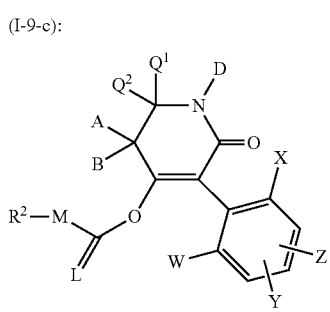

(I-9-d): 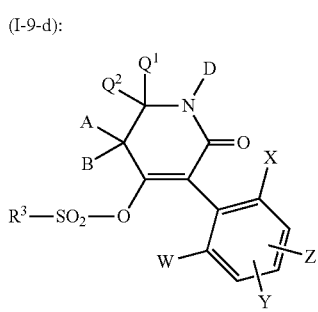

(I-9-e): 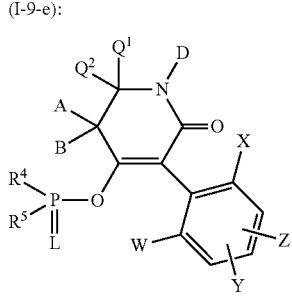

(I-9-f):
(I-9-d):
(I-9-g):

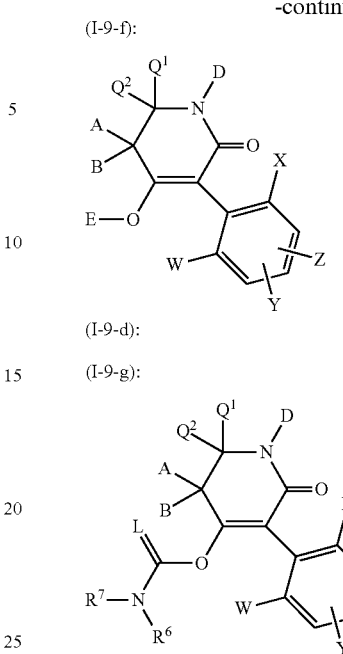

in which
A, B, D, E, L, M, $Q^1$, $Q^2$, W, X, Y, Z, $R^1$, $R^2$, $R^3$, $R^4$, $R^5$, $R^6$ and $R^7$ are as defined above.

Depending on the position of the substituent G the compounds of the formula (I-10) may be present in the two isomeric forms of the formulae (I-10-A) and (I-10-B)

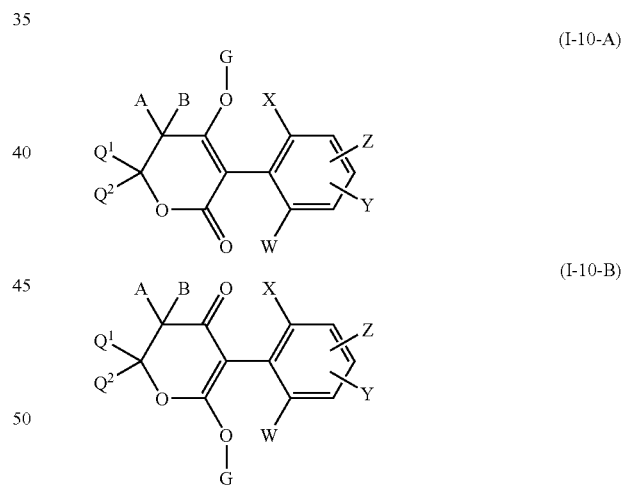

which the dashed line in the formula (I-10) is intended to express.

The compounds of the formulae (I-10-A) and (I-10-B) may be present both as mixtures and in the form of their pure isomers. Mixtures of the compounds of the formulae (I-10-A) and (I-10-B) can be separated where appropriate in conventional manner by means of physical methods, such as by chromatographic methods, for example.

For reasons of greater clarity in each case only one of the possible isomers is set out below. This does not rule out the possibility of the compounds being present where appropriate in the form of the isomer mixtures or in the respective other isomeric form.

Including the various definitions (a), (b), (c), (d), (e), (f) and (g) of the group G produces the following principal structures (I-10-a) to (I-10-g) if CKE is the group (10):

(I-10-a):

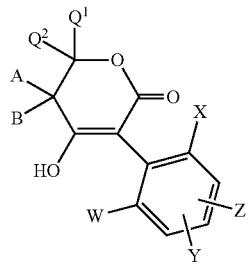

(I-10-b):

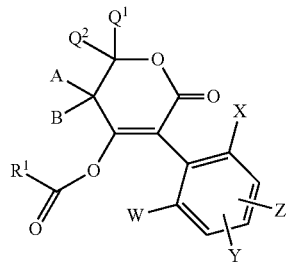

(I-10-c):

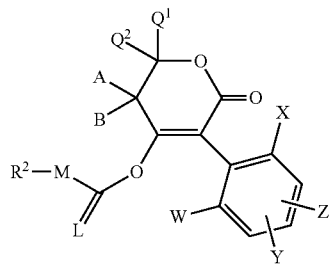

(I-10-d):

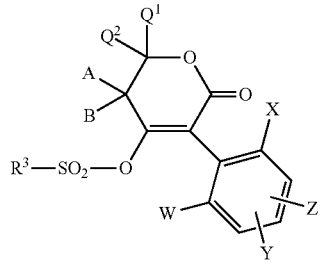

(I-10-e):

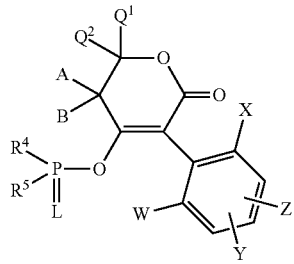

(I-10-f):

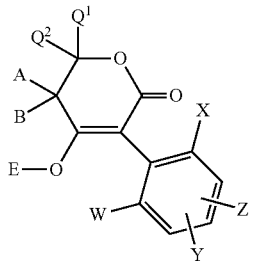

(I-10-g):

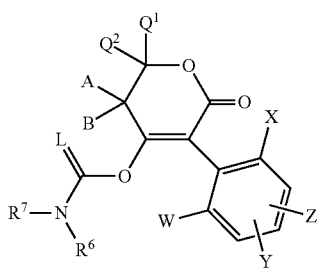

in which
A, B, D, E, L, M, $Q^1$, $Q^2$, W, X, Y, Z, $R^1$, $R^2$, $R^3$, $R^4$, $R^5$, $R^6$ and $R^7$ are as defined above.

A general definition of the compounds of the invention is given by the formula (I). Preferred substituents and/or ranges of the radicals listed in the formulae mentioned above and below are elucidated in the following text:

W is preferably hydrogen, $C_1$-$C_6$-alkyl, $C_2$-$C_6$-alkenyl, $C_2$-$C_6$-alkynyl, halogen, $C_1$-$C_6$-alkoxy, $C_1$-$C_4$-haloalkyl, $C_1$-$C_4$-haloalkoxy or cyano, X is preferably halogen, $C_1$-$C_6$-alkyl, $C_2$-$C_6$-alkenyl, $C_2$-$C_6$-alkynyl, $C_1$-$C_6$-alkoxy, $C_1$-$C_6$-alkoxy-$C_1$-$C_4$-alkoxy, $C_1$-$C_4$-haloalkyl, $C_1$-$C_4$-haloalkoxy or cyano, Y is preferably hydrogen, halogen, $C_1$-$C_6$-alkyl, $C_2$-$C_6$-alkenyl, $C_2$-$C_6$-alkynyl, $C_1$-$C_6$-alkoxy, cyano, $C_1$-$C_4$-haloalkyl, haloalkoxy, or is $V^1$- and $V^2$-substituted phenyl or pyridyl, $V^1$ is preferably halogen, $C_1$-$C_{12}$-alkyl, $C_1$-$C_6$-alkoxy, $C_1$-$C_4$-haloalkyl, $C_1$-$C_4$-haloalkoxy, cyano or nitro.

$V^2$ is preferably hydrogen, halogen, $C_1$-$C_6$-alkyl, $C_1$-$C_6$-alkoxy or $C_1$-$C_4$-haloalkyl, $V^1$ and $V^2$ are preferably together $C_3$-$C_4$-alkanediyl which optionally can be substituted by halogen and/or $C_1$-$C_2$-alkyl and which optionally can be interrupted by one or two oxygen atoms.

Z is preferably hydrogen, halogen, $C_1$-$C_6$-alkyl, $C_1$-$C_4$-haloalkyl, cyano, $C_1$-$C_6$-alkoxy or $C_1$-$C_4$-haloalkoxy.

CKE is preferably one of the groups (1)

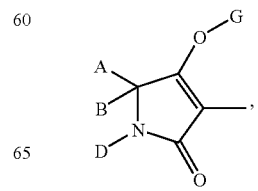

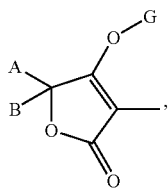

(2)

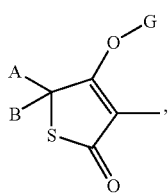

(3)

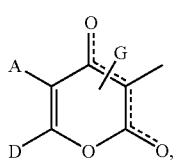

(4)

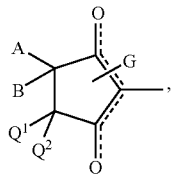

(5)

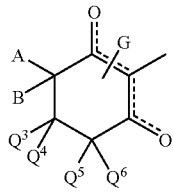

(6)

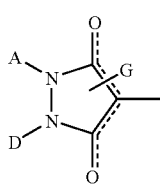

(7)

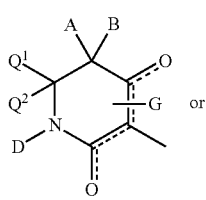 or (9)

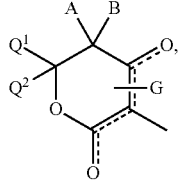

(10)

A is preferably hydrogen or in each case optionally halogen-substituted $C_1$-$C_{12}$-alkyl, $C_3$-$C_8$-alkenyl, $C_1$-$C_{10}$-alkoxy-$C_1$-$C_8$-alkyl, $C_1$-$C_{10}$-alkylthio-$C_1$-$C_6$-alkyl, optionally halogen-, $C_1$-$C_6$-alkyl- or $C_1$-$C_6$-alkoxy-substituted $C_3$-$C_8$-cycloalkyl in which optionally one or two ring members not directly adjacent are replaced by oxygen and/or sulphur, or is in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, naphthyl, hetaryl having 5 to 6 ring atoms (for example furanyl, pyridyl, imidazolyl, triazolyl, pyrazolyl, pyrimidyl, thiazolyl or thienyl), phenyl-$C_1$-$C_6$-alkyl or naphthyl-$C_1$-$C_6$-alkyl, B is preferably hydrogen, $C_1$-$C_{12}$-alkyl or $C_1$-$C_8$-alkoxy-$C_1$-$C_6$-alkyl or A, B and the carbon atom to which they are attached are preferably saturated $C_3$-$C_{10}$-cycloalkyl or unsaturated $C_5$-$C_{10}$-cycloalkyl, in which optionally one ring member is replaced by oxygen or sulphur and which optionally are singly or doubly substituted by $C_1$-$C_8$-alkyl, $C_1$-$C_6$-alkoxy-$C_1$-$C_6$-alkyl, $C_3$-$C_6$-cycloalkyl-$C_1$-$C_2$-alkoxy, $C_3$-$C_{10}$-cycloalkyl, $C_1$-$C_8$-haloalkyl, $C_1$-$C_8$-alkoxy, $C_1$-$C_6$-alkoxy-$C_1$-$C_4$-alkoxy, $C_1$-$C_8$-alkylthio, halogen or phenyl, or A, B and the carbon atom to which they are attached are preferably $C_3$-$C_6$-cycloalkyl which is substituted by an alkylenediyl group which is optionally substituted by $C_1$-$C_4$-alkyl and optionally contains one or two oxygen and/or sulphur atoms not directly adjacent, or by an alkylenedioxyl group or by an alkylenedithioyl group, which with the carbon atom to which it is attached forms a further five- to eight-membered ring, or A, B and the carbon atom to which they are attached are preferably $C_3$-$C_8$-cycloalkyl or $C_5$-$C_8$-cycloalkenyl in which two substituents, together with the carbon atoms to which they are attached, are in each case optionally $C_1$-$C_6$-alkyl-, $C_1$-$C_6$-alkoxy- or halogen-substituted $C_2$-$C_6$-alkanediyl, $C_2$-$C_6$-alkenediyl or $C_4$-$C_6$-alkanedienediyl, in which optionally one methylene group is replaced by oxygen or sulphur, D is preferably hydrogen, in each case optionally halogen-substituted $C_1$-$C_{12}$-alkyl, $C_3$-$C_8$-alkenyl, $C_3$-$C_8$-alkynyl, $C_1$-$C_{10}$-alkoxy-$C_2$-$C_8$-alkyl, optionally halogen-, $C_1$-$C_4$-alkyl-, $C_1$-$C_4$-alkoxy- or $C_1$-$C_4$-haloalkyl-substituted $C_3$-$C_8$-cycloalkyl in which optionally one ring member is replaced by oxygen or sulphur, or is in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, hetaryl having 5 or 6 ring atoms (for example furanyl, imidazolyl, pyridyl, thiazolyl, pyrazolyl, pyrimidyl, pyrrolyl, thienyl or triazolyl), phenyl-$C_1$-$C_6$-alkyl or hetaryl-$C_1$-$C_6$-alkyl having 5 or 6 ring atoms (for example furanyl, imidazolyl, pyridyl, thiazolyl, pyrazolyl, pyrimidyl, pyrrolyl, thienyl or triazolyl) or A and D are preferably together in each case optionally substituted $C_3$-$C_6$-alkanediyl or $C_3$-$C_6$-alkenediyl, in which optionally one methylene group is replaced by a carbonyl group, oxygen or sulphur, and suitable substituents are in each case as follows:

halogen, hydroxyl, mercapto or in each case optionally halogen-substituted $C_1$-$C_{10}$-alkyl, $C_1$-$C_6$-alkoxy, $C_1$-$C_6$-alkylthio, $C_3$-$C_7$-cycloalkyl, phenyl or benzyloxy, or a further $C_3$-$C_6$-alkanediyl moiety, $C_3$-$C_6$-alkenediyl moiety or a butadienyl moiety, which is optionally substituted by $C_1$-$C_6$-alkyl or in which optionally two adjacent substituents, with the carbon atoms to which they are attached, form a further saturated or unsaturated ring having 5 or 6 ring atoms (in the case of the compound of the formula (I-1) A and D, together with the atoms to which they are attached, then are, for example, the groups AD-1 to AD-10 specified later on below), which can contain oxygen or sulphur, or in which optionally one of the following groups

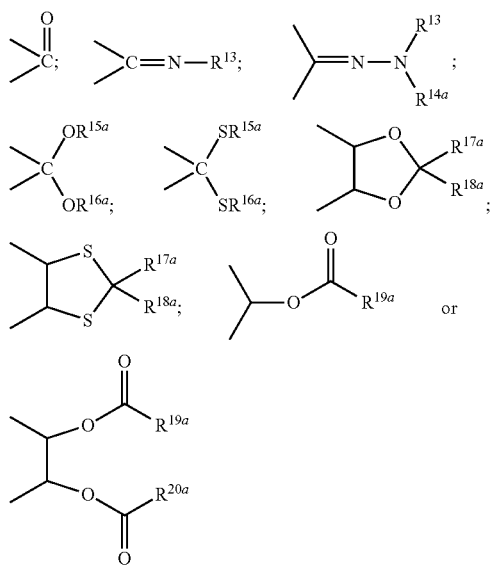

is present, or

A and $Q^1$ are together preferably $C_4$-$C_6$-alkenediyl or $C_3$-$C_6$-alkanediyl which are in each case optionally substituted one or two times by identical or different substituents selected from halogen, hydroxyl, $C_3$-$C_7$-cycloalkyl, $C_1$-$C_6$-alkylthio, $C_1$-$C_6$-alkoxy or $C_1$-$C_{10}$-alkyl in each case optionally substituted one to three times by identical or different halogen substituents, and phenyl or benzyloxy in each case optionally substituted one to three times by identical or different halogen, $C_1$-$C_6$-alkyl or $C_1$-$C_6$-alkoxy substituents, and which, moreover, optionally contains one of the following groups

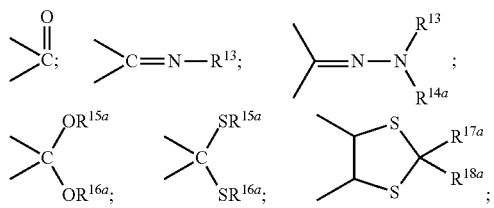

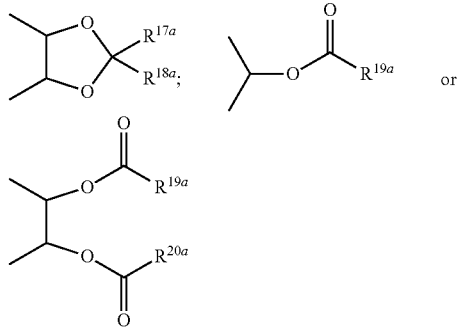

or is bridged by a $C_1$-$C_2$-alkanediyl group or by an oxygen atom, or

D and $Q^1$ are preferably together $C_3$-$C_6$-alkanediyl which is in each case optionally substituted one or two times by identical or different substituents selected from $C_1$-$C_4$-alkyl and $C_1$-$C_4$-alkoxy.

$Q^1$ is preferably hydrogen, $C_1$-$C_6$-alkyl, $C_1$-$C_6$-alkoxy-$C_1$-$C_2$-alkyl, optionally fluorine-, chlorine-, $C_1$-$C_4$-alkyl-, $C_1$-$C_2$-haloalkyl- or $C_1$-$C_4$-alkoxy-substituted $C_3$-$C_8$-cycloalkyl, in which optionally one methylene group is replaced by oxygen or sulphur, or is optionally halogen-, $C_1$-$C_4$-alkyl-, $C_1$-$C_4$-alkoxy-, $C_1$-$C_2$-haloalkyl-, $C_1$-$C_2$-haloalkoxy-, cyano- or nitro-substituted phenyl, or $Q^2$, $Q^4$, $Q^5$ and $Q^6$ independently of one another are preferably hydrogen or $C_1$-$C_4$-alkyl, $Q^3$ is preferably hydrogen, $C_1$-$C_6$-alkyl, $C_1$-$C_6$-alkoxy-$C_1$-$C_2$-alkyl, $C_1$-$C_6$-alkylthio-$C_1$-$C_2$-alkyl, optionally $C_1$-$C_4$-alkyl- or $C_1$-$C_4$-alkoxy-substituted $C_3$-$C_8$-cycloalkyl, in which optionally one methylene group is replaced by oxygen or sulphur, or is optionally halogen-, $C_1$-$C_4$-alkyl-, $C_1$-$C_4$-alkoxy-, $C_1$-$C_2$-haloalkyl-, $C_1$-$C_2$-haloalkoxy-, cyano- or nitro-substituted phenyl.

Q1 and Q2, with the carbon atom to which they are attached, are preferably optionally $C_1$-$C_6$-alkyl-, $C_1$-$C_6$-alkoxy- or $C_1$-$C_2$-haloalkyl-substituted $C_3$-$C_7$ ring in which optionally one ring member is replaced by oxygen or sulphur, $Q^3$ and $Q^4$, together with the carbon atom to which they are attached, are preferably an optionally $C_1$-$C_4$-alkyl-, $C_1$-$C_4$-alkoxy- or $C_1$-$C_2$-haloalkyl-substituted $C_3$-$C_7$ ring in which optionally one ring member is replaced by oxygen or sulphur, G is preferably hydrogen (a) or is one of the groups

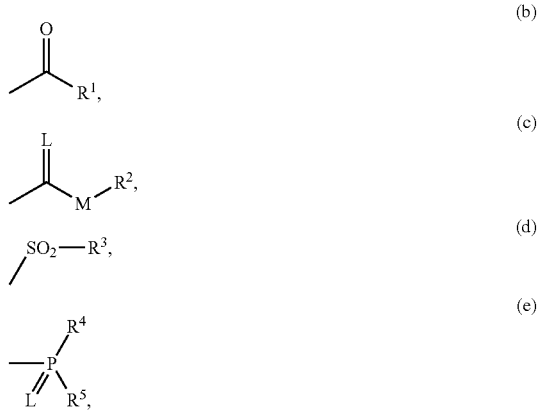

-continued

E or (f)

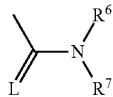
(g)

in particular is (a), (b), (c) or (g)
in which
E is one metal ion equivalent or ammonium ion,
L is oxygen or sulphur and
M is oxygen or sulphur.

$R^1$ is preferably in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl or optionally halogen-, $C_1$-$C_6$-alkyl- or $C_1$-$C_6$-alkoxy-substituted $C_3$-$C_8$-cycloalkyl in which optionally one or more (preferably not more than two) ring members not directly adjacent are replaced by oxygen and/or sulphur,
  is optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl,
  is optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl,
  is optionally halogen- or $C_1$-$C_6$-alkyl-substituted 5- or 6-membered hetaryl (for example pyrazolyl, thiazolyl, pyridyl, pyrimidyl, furanyl or thienyl),
  is optionally halogen- or $C_1$-$C_6$-alkyl-substituted phenoxy-$C_1$-$C_6$-alkyl or
  is optionally halogen-, amino- or $C_1$-$C_6$-alkyl-substituted 5- or 6-membered hetaryloxy-$C_1$-$C_6$-alkyl (for example pyridyloxy-$C_1$-$C_6$-alkyl, pyrimidyloxy-$C_1$-$C_6$-alkyl or thiazolyloxy-$C_1$-$C_6$-alkyl), $R^2$ is preferably in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl,
  is optionally halogen-, $C_1$-$C_6$-alkyl- or $C_1$-$C_6$-alkoxy-substituted $C_3$-$C_8$-cycloalkyl or
  is in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ is preferably optionally halogen-substituted $C_1$-$C_8$-alkyl or is in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another are preferably in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio, $C_2$-$C_8$-alkenylthio, $C_3$-$C_7$-cycloalkylthio or are in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ are preferably independently of one another hydrogen, are in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, are optionally halogen-, $C_1$-$C_8$-haloalkyl-, $C_1$-$C_8$-alkyl- or $C_1$-$C_8$-alkoxy-substituted phenyl, optionally halogen-, $C_1$-$C_8$-alkyl-, $C_1$-$C_8$-haloalkyl- or $C_1$-$C_8$-alkoxy-substituted benzyl or together are an optionally $C_1$-$C_4$-alkyl-substituted $C_3$-$C_6$-alkylene radical in which optionally one carbon atom is replaced by oxygen or sulphur, $R^{13}$ is preferably hydrogen, is in each case optionally halogen-substituted $C_1$-$C_8$-alkyl or $C_1$-$C_8$-alkoxy, is optionally halogen-, $C_1$-$C_4$-alkyl- or $C_1$-$C_4$-alkoxy-substituted $C_3$-$C_8$-cycloalkyl in which optionally one methylene group is replaced by oxygen or sulphur, or is in each case optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl, phenyl-$C_1$-$C_4$-alkyl or phenyl-$C_1$-$C_4$-alkoxy, $R^{14a}$ is preferably hydrogen or $C_1$-$C_8$-alkyl or $R^{13}$ and $R^{14a}$ are preferably together $C_4$-$C_6$-alkanediyl, $R^{15a}$ and $R^{16a}$ are alike or different and are preferably $C_1$-$C_6$-alkyl or $R^{15a}$ and $R^{16a}$ are preferably together a $C_2$-$C_4$-alkanediyl radical which is optionally substituted by $C_1$-$C_6$-alkyl, $C_1$-$C_6$-haloalkyl or by optionally halogen-, $C_1$-$C_6$-alkyl-, $C_1$-$C_4$-haloalkyl-, $C_1$-$C_6$-alkoxy-, $C_1$-$C_4$-haloalkoxy-, nitro- or cyano-substituted phenyl, $R^{17a}$ and $R^{18a}$ are preferably independently of one another hydrogen, are optionally halogen-substituted $C_1$-$C_8$-alkyl or are optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl or $R^{17a}$ and $R^{18a}$, together with the carbon atom to which they are attached, are preferably a carbonyl group or are optionally halogen-, $C_1$-$C_4$-alkyl- or $C_1$-$C_4$-alkoxy-substituted $C_5$-$C_7$-cycloalkyl in which optionally one methylene group is replaced by oxygen or sulphur, $R^{19a}$ and $R^{20a}$ are preferably independently of one another $C_1$-$C_{10}$-alkyl, $C_2$-$C_{10}$-alkenyl, $C_1$-$C_{10}$-alkoxy, $C_1$-$C_{10}$-alkylamino, $C_3$-$C_{10}$-alkenylamino, di-($C_1$-$C_{10}$-alkyl)amino or di-($C_3$-$C_{10}$-alkenyl)amino.

In the radical definitions qualified by "preferably" halogen or halo is fluorine, chlorine, bromine and iodine, in particular fluorine, chlorine and bromine.

W is with particular preference hydrogen, fluorine, chlorine, bromine, $C_1$-$C_4$-alkyl, $C_2$-$C_4$-alkenyl, $C_2$-$C_4$-alkynyl, $C_1$-$C_4$-alkoxy, $C_1$-$C_2$-haloalkyl or $C_1$-$C_2$-haloalkoxy, X is with particular preference chlorine, bromine, iodine, $C_1$-$C_4$-alkyl, $C_2$-$C_4$-alkenyl, $C_2$-$C_4$-alkynyl, $C_1$-$C_4$-alkoxy, $C_1$-$C_4$-alkoxy-$C_1$-$C_3$-alkoxy, $C_1$-$C_2$-haloalkyl, $C_1$-$C_2$-haloalkoxy or cyano, Y is with particular preference in position 4 hydrogen, $C_2$-$C_4$-alkenyl, $C_2$-$C_4$-alkynyl, fluorine, chlorine, bromine, iodine, methoxy, ethoxy, cyano, trifluoromethyl, difluoromethoxy or trifluoromethoxy, Z is with particular preference hydrogen.

W is with particular preference also hydrogen, fluorine, chlorine, bromine or $C_1$-$C_4$-alkyl, X is with particular preference also chlorine, bromine, $C_1$-$C_4$-alkyl, $C_1$-$C_4$-alkoxy, $C_1$-$C_2$-haloalkyl, $C_1$-$C_2$-haloalkoxy or cyano, Y is with particular preference also in position 4 the radical

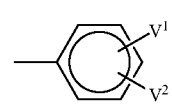

Z is with particular preference also hydrogen, $V^1$ is with particular preference also fluorine, chlorine, $C_1$-$C_4$-alkyl, $C_1$-$C_4$-alkoxy, $C_1$-$C_2$-haloalkyl or $C_1$-$C_2$-haloalkoxy, cyano or nitro, $V^2$ is with particular preference also hydrogen, fluorine, chlorine, $C_1$-$C_4$-alkyl, $C_1$-$C_4$-alkoxy or $C_1$-$C_2$-haloalkyl, $V^1$ and $V^2$ together are with particular preference also —O—$CH_2$—O— and —O—$CF_2$—O—.

W is with particular preference likewise hydrogen, fluorine, chlorine, bromine or $C_1$-$C_4$-alkyl, X is with particular preference likewise chlorine, bromine, $C_1$-$C_4$-alkyl, $C_1$-$C_4$-alkoxy, $C_1$-$C_2$-haloalkyl, $C_1$-$C_2$-haloalkoxy or cyano, Y is with particular preference likewise in position 5 $C_2$-$C_4$-alkenyl, $C_2$-$C_4$-alkynyl or the radical

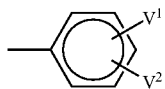

Z is with particular preference likewise in position 4 hydrogen, $C_1$-$C_4$-alkyl or chlorine, $V^1$ is with particular preference likewise fluorine, chlorine, $C_1$-$C_4$-alkyl, $C_1$-$C_4$-alkoxy, $C_1$-$C_2$-haloalkyl or $C_1$-$C_2$-haloalkoxy, cyano or nitro, $V^2$ is with particular preference likewise hydrogen, fluorine, chlorine, $C_1$-$C_4$-alkyl, $C_1$-$C_4$-alkoxy or $C_1$-$C_2$-haloalkyl, $V^1$ and $V^2$ together are with particular preference likewise —O—CH$_2$—O— and —O—CF$_2$—O—.

W moreover is with particular preference hydrogen, $C_1$-$C_4$-alkyl, $C_2$-$C_4$-alkenyl, $C_2$-$C_4$-alkynyl, $C_1$-$C_4$-alkoxy, fluorine, chlorine, bromine or trifluoromethyl, X moreover is with particular preference fluorine, chlorine, bromine, iodine, $C_1$-$C_4$-alkyl, $C_2$-$C_4$-alkenyl, $C_2$-$C_4$-alkynyl, $C_1$-$C_4$-alkoxy, $C_1$-$C_4$-alkoxy-$C_1$-$C_3$-alkoxy, $C_1$-$C_2$-haloalkyl, $C_1$-$C_2$-haloalkoxy or cyano, Y moreover in position 4 is with particular preference $C_1$-$C_4$-alkyl, Z moreover is with particular preference hydrogen.

W additionally is with particular preference hydrogen, fluorine, chlorine, bromine, $C_1$-$C_4$-alkyl or $C_1$-$C_4$-alkoxy, X additionally is with particular preference chlorine, bromine, iodine, $C_1$-$C_4$-alkyl, $C_1$-$C_4$-alkoxy, $C_1$-$C_2$-haloalkyl, $C_1$-$C_2$-haloalkoxy or cyano, Y additionally in position 4 is with particular preference hydrogen, chlorine, bromine, iodine, $C_1$-$C_4$-alkyl, $C_1$-$C_2$-haloalkyl or $C_1$-$C_2$-haloalkoxy, Z additionally in position 3 or 5 is with particular preference fluorine, chlorine, bromine, iodine, $C_1$-$C_4$-alkyl, $C_1$-$C_2$-haloalkyl, $C_1$-$C_4$-alkoxy or $C_1$-$C_2$-haloalkoxy.

CKE stands with particular preference for one of the groups (1)
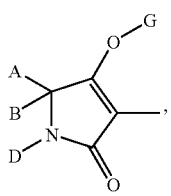

(2)
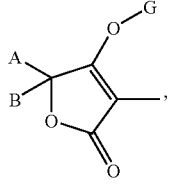

(3)
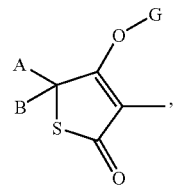

(4)
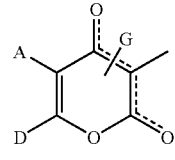

(5)
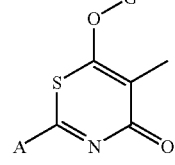

(6)
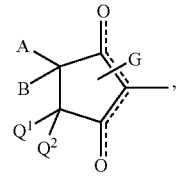

(7)
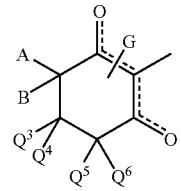

(8)
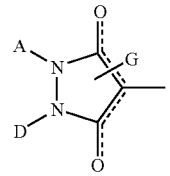

(9)
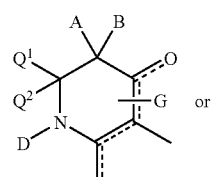

or

(10)
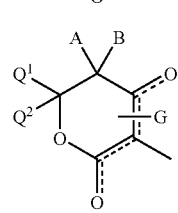

A is with particular preference hydrogen, in each case optionally mono- to tri-fluorine- or -chlorine-substituted $C_1$-$C_6$-alkyl, $C_1$-$C_4$-alkoxy-$C_1$-$C_2$-alkyl, optionally singly to doubly $C_1$-$C_2$-alkyl- or $C_1$-$C_2$-alkoxy-substituted $C_3$-$C_6$-cycloalkyl or (but not in the case of the compounds of the formulae (I-3), (I-4), (I-6) and (I-7)) in each case optionally singly to doubly fluorine-, chlorine-, bromine-, $C_1$-$C_4$-alkyl-, $C_1$-$C_2$-haloalkyl-, $C_1$-$C_4$-alkoxy-, $C_1$-$C_2$-haloalkoxy-, cyano- or nitro-substituted phenyl or benzyl, B is with particular preference hydrogen, $C_1$-$C_4$-alkyl or $C_1$-$C_2$-alkoxy-$C_1$-$C_2$-alkyl, or A, B and the carbon atoms to which they are attached are with particular preference saturated or unsaturated $C_3$-$C_7$-cycloalkyl in which optionally one ring member is replaced by oxygen or sulphur and which is optionally singly to doubly substituted by $C_1$-$C_6$-alkyl, $C_1$-$C_4$-alkoxy-$C_1$-$C_2$-alkyl, trifluoromethyl, $C_1$-$C_6$-alkoxy, $C_1$-$C_3$-alkoxy-$C_1$-$C_3$-alkoxy or $C_3$-$C_6$-cycloalkylmethoxy, with the proviso that in that case $Q^3$ is with particular preference hydrogen or methyl, or A, B and the carbon atom to which they are attached are with particular preference $C_5$-$C_6$-cycloalkyl which is substituted by an alkylenedithiol group or by an alkylenedioxyl group or by an alkylenediyl group which is optionally substituted by methyl or ethyl and optionally contains one or two oxygen or sulphur atoms not directly adjacent, and which, with the carbon atom to which it is attached, forms a further five- or six-membered ring, with the proviso that in that case $Q^3$ is with particular preference hydrogen or methyl, or A, B and the carbon atoms to which they are attached are with particular preference $C_3$-$C_6$-cycloalkyl or $C_5$-$C_6$-cycloalkenyl in which two substituents, together with the carbon atoms to which they are attached, are in each case optionally $C_1$-$C_2$-alkyl- or $C_1$-$C_2$-alkoxy-substituted $C_2$-$C_4$-alkanediyl, $C_2$-$C_4$-alkenediyl or butadienediyl, with the proviso that in that case $Q^3$ is with particular preference hydrogen or methyl, D is with particular preference hydrogen, is in each case optionally mono- to tri-fluoro-substituted $C_1$-$C_6$-alkyl, $C_3$-$C_6$-alkenyl, $C_1$-$C_4$-alkoxy-$C_2$-$C_3$-alkyl, is optionally $C_3$-$C_6$-cycloalkyl which is singly to doubly substituted by $C_1$-$C_4$-alkyl, $C_1$-$C_4$-alkoxy or $C_1$-$C_2$-haloalkyl and in which optionally one methylene group is replaced by oxygen, or (but not in the case of the compounds of the formulae (I-1)) is pyridyl or phenyl in each case optionally substituted singly to doubly by fluorine, chlorine, bromine, $C_1$-$C_4$-alkyl, $C_1$-$C_4$-haloalkyl, $C_1$-$C_4$-alkoxy or $C_1$-$C_4$-haloalkoxy, or A and D together are with particular preference optionally singly to doubly substituted $C_3$-$C_5$-alkanediyl in which one methylene group can be replaced by a carbonyl group (but not in the case of the compounds of the formula (I-1)), oxygen or sulphur, suitable substituents being $C_1$-$C_2$-alkyl or $C_1$-$C_2$-alkoxy, or A and D (in the case of the compounds of the formula (I-1)), together with the atoms to which they are attached, are one of the groups AD-1 to AD-10:

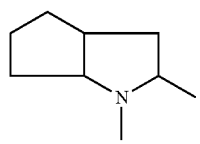
AD-1

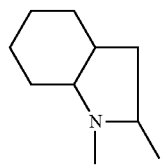
AD-2

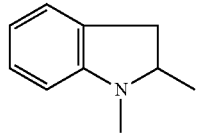
AD-3

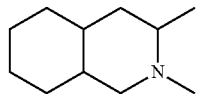
AD-4

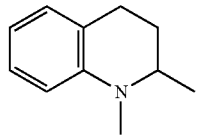
AD-5

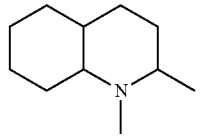
AD-6

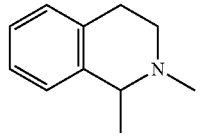
AD-7

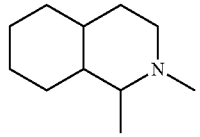
AD-8

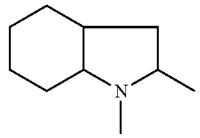
AD-9

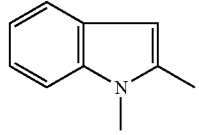
AD-10 or

A and $Q^1$ together are with particular preference $C_3$-$C_4$-alkanediyl in each case optionally substituted singly or doubly by identical or different substituents selected from $C_1$-$C_2$-alkyl or $C_1$-$C_2$-alkoxy, or D and $Q^1$ together are with particular preference $C_3$-$C_4$-alkanediyl, or $Q^1$ is with particular preference hydrogen, $C_1$-$C_4$-alkyl, $C_1$-$C_4$-alkoxy-$C_1$-$C_2$-alkyl, or optionally methyl- or methoxy-substituted $C_3$-$C_6$-cycloalkyl in which optionally one methylene group is replaced by oxygen, $Q^2$ is with particular preference hydrogen, methyl or ethyl, $Q^4$, $Q^5$ and $Q^6$ independently of one another are with particular preference hydrogen or $C_1$-$C_3$-alkyl, $Q^3$ is with particular preference hydrogen, $C_1$-$C_4$-alkyl, or optionally singly to doubly methyl- or methoxy-substituted $C_3$-$C_6$-cycloalkyl, or $Q^1$ and $Q^2$ are with particular preference hydrogen, $C_1$-$C_4$-alkyl, $C_1$-$C_4$-alkoxy-$C_1$-$C_2$-alkyl, or optionally methyl- or methoxy-substituted $C_3$-$C_6$-cycloalkyl in which optionally one methylene group is replaced by oxygen, or $Q^3$ and $Q^4$, together with the carbon to which they are attached, are with particular preference an optionally $C_1$-$C_2$-alkyl- or $C_1$-$C_2$-alkoxy-substituted saturated $C_5$-$C_6$ ring in which optionally one ring member is replaced by oxygen or sulphur, with the proviso that in that case A is with particular preference is hydrogen or methyl, G is with particular preference hydrogen (a) or is one of the groups

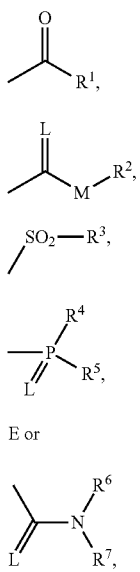

in particular is (a), (b) or (c),
in which
E is one metal ion equivalent or an ammonium ion,
L is oxygen or sulphur and
M is oxygen or sulphur, $R^1$ is with particular preference in each case optionally mono- to tri-fluorine- or -chlorine-substituted $C_1$-$C_8$-alkyl, $C_2$-$C_{18}$-alkenyl, $C_1$-$C_4$-alkoxy-$C_1$-$C_2$-alkyl, $C_1$-$C_4$-alkylthio-$C_1$-$C_2$-alkyl or optionally singly- to doubly fluorine-, chlorine-, $C_1$-$C_2$-alkyl- or $C_1$-$C_2$-alkoxy-substituted $C_3$-$C_6$-cycloalkyl in which optionally one or two ring members not directly adjacent are replaced by oxygen, is phenyl optionally substituted by fluorine, chlorine, bromine, cyano, nitro, $C_1$-$C_4$-alkyl, $C_1$-$C_4$-alkoxy, $C_1$-$C_2$-haloalkyl or $C_1$-$C_2$-haloalkoxy, $R^2$ is in each case optionally mono- to tri-fluorine-substituted $C_1$-$C_8$-alkyl, $C_2$-$C_8$-alkenyl or $C_1$-$C_4$-alkoxy-$C_2$-$C_4$-alkyl, is optionally mono-$C_1$-$C_2$-alkyl- or —$C_1$-$C_2$-alkoxy-substituted $C_3$-$C_6$-cycloalkyl or is benzyl or phenyl in each case optionally substituted singly to doubly by fluorine, chlorine, bromine, cyano, nitro, $C_1$-$C_4$-alkyl, $C_1$-$C_3$-alkoxy, trifluoromethyl or trifluoromethoxy, $R^3$ is with particular preference $C_1$-$C_6$-alkyl optionally substituted one to three times by fluorine or is phenyl optionally substituted once by fluorine, chlorine, bromine, $C_1$-$C_4$-alkyl, $C_1$-$C_4$-alkoxy, trifluoromethyl, trifluoromethoxy, cyano or nitro, $R^4$ is with particular preference $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio, $C_3$-$C_4$-alkenylthio, $C_3$-$C_6$-cycloalkylthio or is phenylthio, phenoxy or phenyl in each case optionally substituted once by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or trifluoromethyl, $R^5$ is with particular preference $C_1$-$C_6$-alkoxy or $C_1$-$C_6$-alkylthio, $R^6$ is with particular preference hydrogen, $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_4$-alkyl, is phenyl optionally substituted once by fluorine, chlorine, bromine, trifluoromethyl, $C_1$-$C_4$-alkyl or $C_1$-$C_4$-alkoxy, or is benzyl optionally substituted once by fluorine, chlorine, bromine, $C_1$-$C_4$-alkyl, trifluoromethyl or $C_1$-$C_4$-alkoxy, $R^7$ is with particular preference $C_1$-$C_6$-alkyl, $C_3$-$C_6$-alkenyl or $C_1$-$C_6$-alkoxy-$C_1$-$C_4$-alkyl, $R^6$ and $R^7$ together are with particular preference an optionally methyl- or ethyl-substituted $C_4$-$C_5$-alkylene radical in which optionally one methylene group is replaced by oxygen or sulphur.

In the radical definitions qualified by "with particular preference" halogen or halo is fluorine, chlorine and bromine, especially fluorine and chlorine.

W is with very particular preference hydrogen, methyl, chlorine, bromine, ethyl, methoxy, ethoxy or trifluoromethyl, X is with very particular preference chlorine, bromine, iodine, methyl, ethyl, propyl, methoxy, ethoxy, propoxy, methoxy-ethoxy, ethoxy-ethoxy, trifluoromethyl, difluoromethoxy, trifluoromethoxy or cyano, Y is with very particular preference in position 4 hydrogen, chlorine, bromine, iodine, trifluoromethyl or trifluoromethoxy, Z is with very particular preference hydrogen.

W is with very particular preference also hydrogen, chlorine, bromine, methyl or ethyl, X is with very particular preference also chlorine, bromine, methyl, ethyl, propyl, methoxy, trifluoromethyl, difluoromethoxy, trifluoromethoxy or cyano, Y is with very particular preference also in position 4 the radical

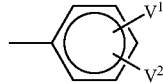

Z is with very particular preference also hydrogen, $V^1$ is with very particular preference also fluorine, chlorine, methyl, methoxy, trifluoromethyl, trifluoromethoxy or cyano, $V^2$ is with very particular preference also hydrogen, fluorine, chlorine, methyl, methoxy or trifluoromethyl.

W is with very particular preference likewise hydrogen, chlorine or methyl,

X is with very particular preference likewise chlorine, methyl, trifluoromethyl, methoxy, difluoromethoxy, trifluoromethoxy or cyano, Y is with very particular preference likewise in position 5 the radical

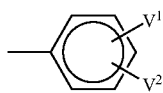

Z is with very particular preference likewise in position 4 hydrogen or methyl, $V^1$ is with very particular preference likewise fluorine, chlorine, methyl, methoxy, trifluoromethyl, trifluoromethoxy or cyano, $V^2$ is with very particular preference likewise hydrogen, fluorine, chlorine, methyl, methoxy or trifluoromethyl.

W is moreover with very particular preference hydrogen, methyl, ethyl, methoxy, ethoxy, chlorine or bromine, X is moreover with very particular preference chlorine, bromine, iodine, methyl, ethyl, propyl, methoxy, ethoxy, propoxy, methoxy-ethoxy, ethoxy-ethoxy, trifluoromethyl, difluoromethoxy, trifluoromethoxy or cyano, Y is moreover with very particular preference in position 4 methyl or ethyl, Z is moreover with very particular preference hydrogen.

W is with very particular preference additionally hydrogen, chlorine, bromine, methyl or ethyl, X is with very particular preference additionally chlorine, bromine, iodine, methyl, ethyl, methoxy, trifluoromethyl, difluoromethoxy or trifluoromethoxy, Y is with very particular preference additionally in position 4 hydrogen, chlorine, bromine, methyl or ethyl, Z is with very particular preference additionally in position 3 or 5 fluorine, chlorine, bromine, iodine, methyl, ethyl, trifluoromethyl or trifluoromethoxy.

CKE stands with very particular preference for one of the groups

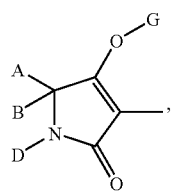
(1)

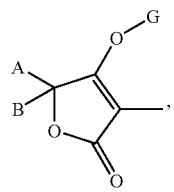
(2)

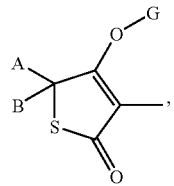
(3)

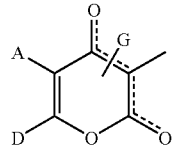
(4)

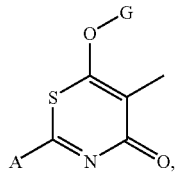
(5)

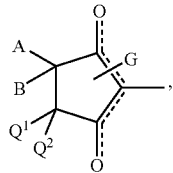
(6)

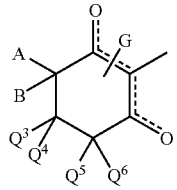
(7)

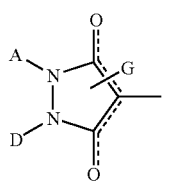
(8)

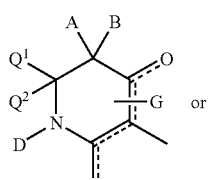 or
(9)

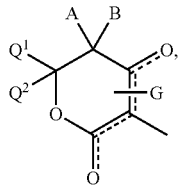
(10)

A is with very particular preference hydrogen, in each case optionally mono- to tri-fluorine-substituted $C_1$-$C_4$-alkyl, $C_1$-$C_2$-alkoxy-$C_1$-$C_2$-alkyl, is cyclopropyl, cyclopentyl or cyclohexyl and only in the case of the compounds of the formula (I-5) is phenyl optionally substituted singly to doubly by fluorine, chlorine, bromine, methyl, ethyl, n-propyl, isopropyl, methoxy, ethoxy, trifluoromethyl, trifluoromethoxy, cyano or nitro, B is with very particular preference hydrogen, methyl or ethyl, or A, B and the carbon atom to which they are attached are with very particular preference saturated $C_5$-$C_6$-cycloalkyl in which optionally one ring member is replaced by oxygen or sulphur and which is optionally substituted once by methyl, ethyl, propyl, isopropyl, methoxymethyl, ethoxymethyl, propoxymethyl, methoxyethyl, ethoxyethyl, trifluoromethyl, methoxy, ethoxy, propoxy, methoxyethoxy, butoxy, ethoxyethoxy or cyclopropylmethoxy, with the proviso that in that case $Q^3$ is with very particular preference hydrogen, or A, B and the carbon atom to which they are attached are with very particular preference $C_6$-cycloalkyl which is optionally substituted by an alkylenedioxyl group which contains two oxygen atoms not directly adjacent, with the proviso that in that case $Q^3$ is with very particular preference hydrogen, or A, B and the carbon atom to which they are attached are with very particular preference $C_5$-$C_6$-cycloalkyl or $C_5$-$C_6$-cycloalkenyl, in which two substituents, together with the carbon atoms to which they are attached, are $C_2$-$C_4$-alkanediyl or $C_2$-$C_4$-alkenediyl or butadienediyl, with the proviso that in that case $Q^3$ is with very particular preference hydrogen, D is with very particular preference hydrogen, is in each case optionally mono- to tri-fluoro-substituted $C_1$-$C_4$-alkyl, $C_3$-$C_4$-alkenyl, $C_1$-$C_4$-alkoxy-$C_2$-$C_3$-alkyl, is cyclopropyl, cyclopentyl or cyclohexyl or (but not in the case of the compounds of the formulae (I-1)) is pyridyl or phenyl in each case optionally substituted once by fluorine, chlorine, methyl, ethyl, n-propyl, isopropyl, methoxy, ethoxy or trifluoromethyl, or A and D together are with very particular preference $C_3$-$C_5$-alkanediyl which is optionally substituted once by methyl or methoxy and in which optionally one carbon atom is replaced by oxygen or sulphur, or is the group AD-1, or A and $Q^1$ are together with very particular preference $C_3$-$C_4$-alkanediyl optionally substituted singly to doubly by methyl or methoxy, or D and $Q^1$ are together with very particular preference $C_3$-$C_4$-alkanediyl, or $Q^1$ is with very particular preference hydrogen, methyl, ethyl, propyl, isopropyl, cyclopropyl, cyclopentyl or cyclohexyl, $Q^2$ is with very particular preference hydrogen, methyl or ethyl, $Q^4$, $Q^5$ and $Q^6$ are with very particular preference independently of one another hydrogen or methyl, $Q^3$ is with very particular preference hydrogen, methyl, ethyl or propyl, or $Q^3$ and $Q^4$, are with very particular preference, together with the carbon to which they are attached, an optionally monomethyl- or -methoxy-substituted saturated $C_5$-$C_6$ ring, with the proviso that in that case A is with very particular preference hydrogen, G is with very particular preference hydrogen (a) or is one of the groups

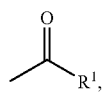 (b)

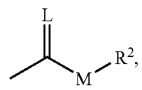 (c)

—$SO_2$—$R^3$ (d) or E (f), in which
L is oxygen or sulphur,
M is oxygen or sulphur and
E is an ammonium ion,
$R^1$ is with very particular preference in each case optionally mono-chloro-substituted $C_1$-$C_6$-alkyl, $C_2$-$C_{17}$-alkenyl, $C_1$-$C_2$-alkoxy-$C_1$-alkyl, $C_1$-$C_2$-alkylthio-$C_1$-alkyl or in each case optionally mono-fluorine-, -chlorine-, -methyl- or -methoxy-substituted cyclopropyl or cyclohexyl,
is phenyl optionally substituted once by fluorine, chlorine, bromine, cyano, nitro, methyl, methoxy, trifluoromethyl or trifluoromethoxy,
$R^2$ is with very particular preference in each case optionally mono-fluoro-substituted $C_1$-$C_8$-alkyl, $C_2$-$C_6$-alkenyl or $C_1$-$C_4$-alkoxy-$C_2$-$C_3$-alkyl, phenyl or benzyl,
$R^3$ is with very particular preference $C_1$-$C_8$-alkyl.

Specifically mention may be made, apart from the compounds specified in the examples, of the following compounds:

TABLE 1

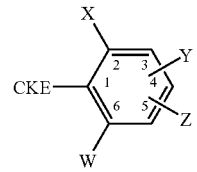

| X | W | Y | Z |
|---|---|---|---|
| $CH_3$ | H | H | H |
| Br | H | H | H |
| Cl | H | H | H |
| $CF_3$ | H | H | H |
| $OCH_3$ | H | H | H |
| Br | H | 4-Cl | H |
| Cl | H | 4-Br | H |
| Cl | H | 4-Cl | H |
| Cl | H | 4-$CH_3$ | H |
| $CH_3$ | H | 4-Cl | H |
| $CH_3$ | H | 4-$CH_3$ | H |
| Cl | Cl | H | H |
| Cl | $OCH_3$ | H | H |
| Cl | $CH_3$ | H | H |
| Cl | $OC_2H_5$ | H | H |
| $OCH_3$ | $OCH_3$ | H | H |
| $CH_3$ | $CH_3$ | H | H |
| Br | $CH_3$ | 4-Br | H |
| Cl | Cl | 4-$CH_3$ | H |
| $CH_3$ | Br | 4-$CH_3$ | H |
| $CH_3$ | Cl | 4-$CH_3$ | H |
| $OCH_3$ | $CH_3$ | 4-$CH_3$ | H |
| $OC_2H_5$ | $CH_3$ | 4-$CH_3$ | H |
| $OC_3H_7$ | $CH_3$ | 4-$CH_3$ | H |
| $CH_3$ | $CH_3$ | 4-$CH_3$ | H |
| Br | Br | 4-$CH_3$ | H |
| $CH_3$ | $CH_3$ | 4-Br | H |
| $C_2H_5$ | $CH_3$ | H | H |
| $C_2H_5$ | $C_2H_5$ | H | H |
| $OCH_3$ | $C_2H_5$ | 4-$CH_3$ | H |
| $CH_3$ | $CH_3$ | 4-$OCH_3$ | H |
| Br | Cl | 4-$CH_3$ | H |
| Br | $CH_3$ | 4-Cl | H |
| Cl | $CH_3$ | 4-Br | H |
| $CH_3$ | $CH_3$ | 4-Cl | H |
| $C_2H_5$ | $CH_3$ | 4-$CH_3$ | H |
| $C_2H_5$ | $CH_3$ | 4-$C_2H_5$ | H |
| $C_2H_5$ | $C_2H_5$ | 4-$CH_3$ | H |
| $C_2H_5$ | $C_2H_5$ | 4-$C_2H_5$ | H |
| $C_2H_5$ | $CH_3$ | 4-Cl | H |
| $C_2H_5$ | $C_2H_5$ | 4-Cl | H |
| $C_2H_5$ | $CH_3$ | 4-Br | H |
| $C_2H_5$ | $C_2H_5$ | 4-Br | H |
| $C_2H_5$ | Cl | 4-$CH_3$ | H |
| $C_2H_5$ | Br | 4-$CH_3$ | H |
| $C_2H_5$ | Cl | 4-Cl | H |
| $C_2H_5$ | Br | 4-Br | H |
| $C_2H_5$ | Cl | 4-Br | H |
| $C_2H_5$ | Br | 4-Cl | H |
| $OCH_3$ | $CH_3$ | 4-Cl | H |
| $OCH_3$ | $C_2H_5$ | 4-Cl | H |
| $OC_2H_5$ | $CH_3$ | 4-Cl | H |
| $OC_2H_5$ | $C_2H_5$ | 4-Cl | H |

TABLE 1-continued

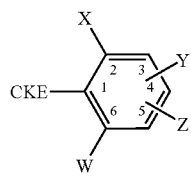

| X | W | Y | Z |
|---|---|---|---|
| Cl | OCH$_3$ | 4-CH$_3$ | H |
| Cl | OC$_2$H$_5$ | 4-CH$_3$ | H |
| Cl | Cl | 4-Cl | H |
| Cl | H | 4-Cl | 5-Cl |
| CH$_3$ | H | 4-CH$_3$ | 5-CH$_3$ |
| CH$_3$ | H | 4-Cl | 5-CH$_3$ |
| Br | H | 4-Cl | 5-CH$_3$ |
| Br | H | 4-CH$_3$ | 5-CH$_3$ |
| Cl | H | 4-Br | 5-CH$_3$ |
| Cl | H | 4-Cl | 5-CH$_3$ |
| CH$_3$ | H | 4-Br | 5-CH$_3$ |
| Cl | H | 4-CH$_3$ | 5-Cl |
| CH$_3$ | H | H | 5-CH$_3$ |
| Cl | H | H | 5-CH$_3$ |
| Br | H | H | 5-CH$_3$ |
| CH$_3$ | H | H | 5-Cl |
| CH$_3$ | H | H | 5-Br |
| CH$_3$ | CH$_3$ | 4-CH$_3$ | 5-CH$_3$ |
| CH$_3$ | CH$_3$ | 4-CH$_3$ | 5-Cl |
| CH$_3$ | CH$_3$ | 4-CH$_3$ | 5-Br |
| CH$_3$ | CH$_3$ | H | 3-Cl |
| CH$_3$ | CH$_3$ | H | 3-Br |
| Cl | Cl | H | 3-Br |
| CH$_3$ | CH$_3$ | 4-(4-Cl—C$_6$H$_4$) | H |
| C$_2$H$_5$ | CH$_3$ | 4-(4-Cl—C$_6$H$_4$) | H |
| C$_2$H$_5$ | C$_2$H$_5$ | 4-(4-Cl—C$_6$H$_4$) | H |
| Cl | CH$_3$ | 4-(4-Cl—C$_6$H$_4$) | H |
| Cl | C$_2$H$_5$ | 4-(4-Cl—C$_6$H$_4$) | H |
| CH$_3$ | H | 5-(4-Cl—C$_6$H$_4$) | H |
| CH$_3$ | CH$_3$ | 5-(4-Cl—C$_6$H$_4$) | H |
| CH$_3$ | H | 5-(4-Cl—C$_6$H$_4$) | 4-CH$_3$ |
| CH$_3$ | CH$_3$ | 5-(4-Cl—C$_6$H$_4$) | 4-CH$_3$ |
| Cl | H | 5-(4-Cl—C$_6$H$_4$) | H |
| I | H | H | H |
| I | H | 4-CH$_3$ | H |
| I | CH$_3$ | H | H |
| I | C$_2$H$_5$ | H | H |
| CH$_3$ | H | H | 5-I |
| CH$_3$ | H | 4-CH$_3$ | 5-I |
| I | CH$_3$ | 4-CH$_3$ | H |
| I | C$_2$H$_5$ | 4-CH$_3$ | H |
| I | CH$_3$ | 4-Cl | H |
| I | C$_2$H$_5$ | 4-Cl | H |
| I | Cl | 4-CH$_3$ | H |
| I | H | 4-CH$_3$ | 5-CH$_3$ |
| CH$_3$ | H | 4-I | H |
| C$_2$H$_5$ | H | 4-I | H |
| CH$_3$ | CH$_3$ | 4-I | H |
| C$_2$H$_5$ | CH$_3$ | 4-I | H |
| C$_2$H$_5$ | C$_2$H$_5$ | 4-I | H |
| Cl | CH$_3$ | 4-I | H |
| Cl | C$_2$H$_5$ | 4-I | H |
| CH$_3$ | H | 4-I | 5-CH$_3$ |
| CH$_3$ | CH$_3$ | H | 3-I |
| I | H | H | 5-CH$_3$ |

Compounds suitable with particular preference as active ingredients of the invention are compounds having the radical combinations specified in Table 1 for W, X, Y and Z and the radical combinations specified in Tables 2a and 2b for A, B and D.

TABLE 2a

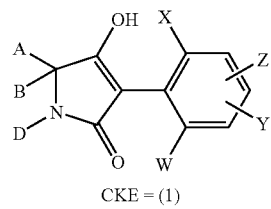

CKE = (1)

| A | B | D |
|---|---|---|
| CH$_3$ | H | H |
| C$_2$H$_5$ | H | H |
| C$_3$H$_7$ | H | H |
| i-C$_3$H$_7$ | H | H |
| C$_4$H$_9$ | H | H |
| i-C$_4$H$_9$ | H | H |
| s-C$_4$H$_9$ | H | H |
| t-C$_4$H$_9$ | H | H |
| CH$_3$ | CH$_3$ | H |
| C$_2$H$_5$ | CH$_3$ | H |
| C$_3$H$_7$ | CH$_3$ | H |
| i-C$_3$H$_7$ | CH$_3$ | H |
| C$_4$H$_9$ | CH$_3$ | H |
| i-C$_4$H$_9$ | CH$_3$ | H |
| s-C$_4$H$_9$ | CH$_3$ | H |
| t-C$_4$H$_9$ | CH$_3$ | H |
| C$_2$H$_5$ | C$_2$H$_5$ | H |
| C$_3$H$_7$ | C$_3$H$_7$ | H |
| cyclopropyl | CH$_3$ | H |
| cyclopentyl | CH$_3$ | H |
| cyclohexyl | CH$_3$ | H |
| —(CH$_2$)$_2$— | | H |
| —(CH$_2$)$_4$— | | H |
| —(CH$_2$)$_5$— | | H |
| —(CH$_2$)$_6$— | | H |
| —(CH$_2$)$_7$— | | H |
| —(CH$_2$)$_2$—O—(CH$_2$)$_2$— | | H |
| —CH$_2$—O—(CH$_2$)$_3$— | | H |
| —(CH$_2$)$_2$—S—(CH$_2$)$_2$— | | H |
| —CH$_2$—CHCH$_3$—(CH$_2$)$_3$— | | H |
| —CH$_2$—CHOCH$_3$—(CH$_2$)$_2$— | | H |
| —CH$_2$—CHOC$_2$H$_5$—(CH$_2$)$_2$— | | H |
| —CH$_2$—CHOC$_3$H$_7$—(CH$_2$)$_2$— | | H |
| —CH$_2$—CHOC$_4$H$_9$—(CH$_2$)$_2$— | | H |
| —CH$_2$—CHO(CH$_2$)$_2$OCH$_3$—(CH$_2$)$_2$— | | H |
| —CH$_2$—CH(OCH$_2$-cyclopropyl)—(CH$_2$)$_2$— | | H |
| —CH$_2$—CHOCH$_3$—(CH$_2$)$_3$— | | H |
| —CH$_2$—CHOC$_2$H$_5$—(CH$_2$)$_3$— | | H |
| —CH$_2$—CHOC$_3$H$_7$—(CH$_2$)$_3$— | | H |
| —CH$_2$—CHOC$_4$H$_9$—(CH$_2$)$_3$— | | H |
| —CH$_2$—CHO(CH$_2$)$_2$OCH$_3$—(CH$_2$)$_3$— | | H |
| —CH$_2$—CH(OCH$_2$-cyclopropyl)—(CH$_2$)$_3$— | | H |
| —(CH$_2$)$_2$—CHCH$_3$—(CH$_2$)$_2$— | | H |
| —(CH$_2$)$_2$—CHC$_2$H$_5$—(CH$_2$)$_2$— | | H |
| —(CH$_2$)$_2$—CHC$_3$H$_7$—(CH$_2$)$_2$— | | H |

TABLE 2a-continued

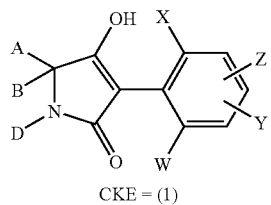

CKE = (1)

| A | B | D |
|---|---|---|
| —(CH$_2$)$_2$—CHi-C$_3$H$_7$—(CH$_2$)$_2$— | | H |
| —(CH$_2$)$_2$—CHOCH$_3$—(CH$_2$)$_2$— | | H |
| —(CH$_2$)$_2$—CHOC$_2$H$_5$—(CH$_2$)$_2$— | | H |
| —(CH$_2$)$_2$—CHOC$_3$H$_7$—(CH$_2$)$_2$— | | H |
| —(CH$_2$)$_2$—CHO-i-C$_3$H$_7$—(CH$_2$)$_2$— | | H |
| —(CH$_2$)$_2$—C(CH$_3$)$_2$—(CH$_2$)$_2$— | | H |
| —CH$_2$—(CHCH$_3$)$_2$—(CH$_2$)$_2$— | | H |
| —CH$_2$—CH—(CH$_2$)$_2$—CH— bridged by CH$_2$ | | H |
| —CH$_2$—CH—CH—CH$_2$— bridged by (CH$_2$)$_4$ | | H |
| —CH$_2$—CH—CH—(CH$_2$)$_2$— bridged by (CH$_2$)$_3$ | | H |
| indane ring | | H |
| tetrahydronaphthalene ring | | H |
| —(CH$_2$)$_2$—(CH$_2$)$_2$— with 1,3-dioxolane | | H |
| —(CH$_2$)$_2$—(CH$_2$)$_2$— with 4-methyl-1,3-dioxolane | | H |
| —(CH$_2$)$_2$—(CH$_2$)$_2$— with 4,5-dimethyl-1,3-dioxolane | | H |
| —(CH$_2$)$_2$—(CH$_2$)$_2$— with 1,3-dioxane | | H |

TABLE 2a-continued

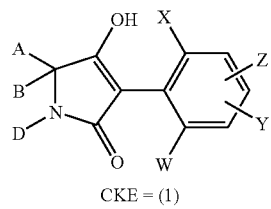

CKE = (1)

| A | B | D |
|---|---|---|
| —(CH$_2$)$_2$—(CH$_2$)$_2$— with 4-methyl-1,3-dioxane | | H |
| —(CH$_2$)$_2$—(CH$_2$)$_2$— with 5-methyl-1,3-dioxane | | H |
| —(CH$_2$)$_2$—(CH$_2$)$_2$— with 4,6-dimethyl-1,3-dioxane | | H |
| —(CH$_2$)$_2$—(CH$_2$)$_2$— with 5,5-dimethyl-1,3-dioxane | | H |
| —CH$_2$—CH(CH$_2$OCH$_3$)—(CH$_2$)$_3$— | | H |
| —CH$_2$—CH((CH$_2$)$_2$OCH$_3$)—(CH$_2$)$_3$— | | H |
| —(CH$_2$)$_2$—CH(CH$_2$OCH$_3$)—(CH$_2$)$_2$— | | H |
| —(CH$_2$)$_2$—CH((CH$_2$)$_2$OCH$_3$)—(CH$_2$)$_2$— | | H |
| —CH$_2$—CH(CH$_2$OCH$_2$CH$_3$)—(CH$_2$)$_3$— | | H |
| —CH$_2$—CH((CH$_2$)$_2$OCH$_2$CH$_3$)—(CH$_2$)$_3$— | | H |

TABLE 2a-continued

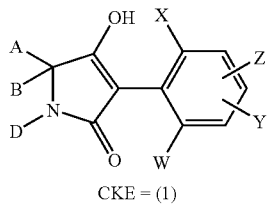

CKE = (1)

| A | B | D |
|---|---|---|
| —(CH₂)₂—CH(CH₂OCH₂CH₃)—(CH₂)₂— | | H |
| —(CH₂)₂—C((CH₂)₂OCH₂CH₃)—(CH₂)₂— | | H |

TABLE 2b

| A | D | B |
|---|---|---|
| | —(CH₂)₃— | H |
| | —(CH₂)₄— | H |
| | —CH₂—CHCH₃—CH₂— | H |
| | —CH₂—CH₂—CHCH₃— | H |
| | —CH₂—CHCH₃—CHCH₃— | H |
| | —CH₂—CH(OCH₃)—CH₂— | H |
| | —CH₂—CH=CH—CH₂— | H |
| | —CH₂—CH(-O-)CH—CH₂— (epoxide) | H |
| | —CH₂—S—CH₂— | H |
| | —CH₂—S—(CH₂)₂— | H |
| | —(CH₂)₂—S—CH₂— | H |
| | —CH₂—CH—CH— with (CH₂)₃ bridge | H |
| H | CH₃ | H |
| H | C₂H₅ | H |
| H | C₃H₇ | H |
| H | i-C₃H₇ | H |
| H | cyclopropyl | H |
| H | methylcyclopentyl | H |
| H | methylcyclohexyl | H |
| CH₃ | CH₃ | H |
| CH₃ | C₂H₅ | H |
| CH₃ | C₃H₇ | H |
| CH₃ | i-C₃H₇ | H |
| CH₃ | cyclopropyl | H |
| CH₃ | methylcyclopentyl | H |

TABLE 2b-continued

| A | D | B |
|---|---|---|
| CH₃ | methylcyclohexyl | H |
| C₂H₅ | CH₃ | H |
| C₂H₅ | C₂H₅ | H |

Compounds suitable as active ingredients of the invention are, with particular preference, compounds having the radical combinations specified in Table 1 for W, X, Y and Z and the radical combinations specified in Table 3 for A and B.

TABLE 3

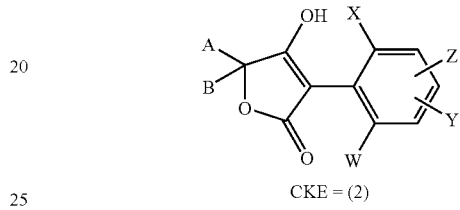

CKE = (2)

| A | B |
|---|---|
| CH₃ | H |
| C₂H₅ | H |
| C₃H₇ | H |
| i-C₃H₇ | H |
| C₄H₉ | H |
| i-C₄H₉ | H |
| s-C₄H₉ | H |
| t-C₄H₉ | H |
| CH₃ | CH₃ |
| C₂H₅ | CH₃ |
| C₃H₇ | CH₃ |
| i-C₃H₇ | CH₃ |
| C₄H₉ | CH₃ |
| i-C₄H₉ | CH₃ |
| s-C₄H₉ | CH₃ |
| t-C₄H₉ | CH₃ |
| C₂H₅ | C₂H₅ |
| C₃H₇ | C₃H₇ |
| cyclopropyl | CH₃ |
| methylcyclopentyl | CH₃ |
| methylcyclohexyl | CH₃ |
| —(CH₂)₂— | |
| —(CH₂)₄— | |
| —(CH₂)₅— | |
| —(CH₂)₆— | |
| —(CH₂)₇— | |
| —(CH₂)₂—O—(CH₂)₂— | |
| —CH₂—O—(CH₂)₃— | |
| —(CH₂)₂—S—(CH₂)₂— | |
| —CH₂—CHCH₃—(CH₂)₃— | |
| —CH₂—CHOCH₃—(CH₂)₃— | |
| —CH₂—CHOC₂H₅—(CH₂)₃— | |
| —CH₂—CHOC₃H₇—(CH₂)₃— | |
| —CH₂—CHOC₄H₉—(CH₂)₃— | |
| —CH₂—CHO(CH₂)₂OCH₃—(CH₂)₃— | |
| —(CH₂)₂—CHCH₃—(CH₂)₂— | |
| —(CH₂)₂—CHC₂H₅—(CH₂)₂— | |
| —(CH₂)₂—CHC₃H₇—(CH₂)₂— | |

TABLE 3-continued
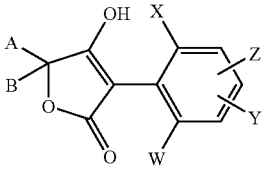
CKE = (2)
| A | B |
|---|---|
| —(CH$_2$)$_2$—CHi-C$_3$H$_7$—(CH$_2$)$_2$— | |
| —(CH$_2$)$_2$—CHOCH$_3$—(CH$_2$)$_2$— | |
| —(CH$_2$)$_2$—CHOC$_2$H$_5$—(CH$_2$)$_2$— | |
| —(CH$_2$)$_2$—CHOC$_3$H$_7$—(CH$_2$)$_2$— | |
| —(CH$_2$)$_2$—CHO-i-C$_3$H$_7$—(CH$_2$)$_2$— | |
| —(CH$_2$)$_2$—C(CH$_3$)$_2$—(CH$_2$)$_2$— | |
| —CH$_2$—(CHCH$_3$)$_2$—(CH$_2$)$_2$— | |
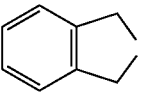
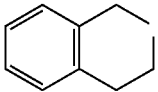
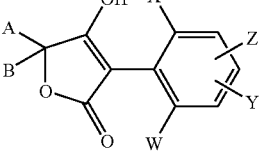
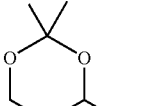
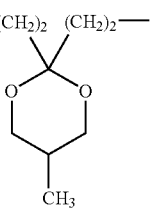
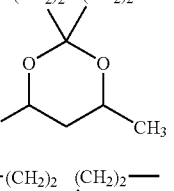
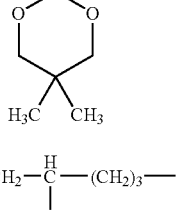
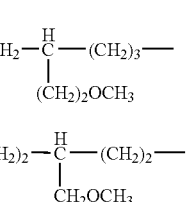
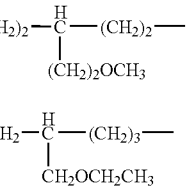
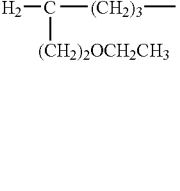

TABLE 3-continued

CKE = (2)

[Structure: furanone with OH, A, B substituents and aryl group with W, X, Y, Z]

| A | B |
|---|---|
| —(CH₂)₂—CH(CH₂OCH₂CH₃)—(CH₂)₂— | |
| —(CH₂)₂—CH((CH₂)₂OCH₂CH₃)—(CH₂)₂— | |

Compounds suitable as active ingredients of the invention are, with particular preference, compounds having the radical combinations specified in Table 1 for W, X, Y and Z and the radical combinations specified in Table 4 for A and D.

CKE = (8)

[Structure: pyrazolone with OH, A, D, and aryl group with W, X, Y, Z]

TABLE 4

| A | D |
|---|---|
| CH₃ | CH₃ |
| C₂H₅ | CH₃ |
| C₃H₇ | CH₃ |
| C₂H₅ | C₂H₅ |
| —(CH₂)₃— | |
| —(CH₂)₄— | |
| —(CH₂)₅— | |
| —(CH₂)₂—O—(CH₂)₂— | |
| —CH₂—CHCH₃—(CH₂)₂— | |
| —CH₂—CHOCH₃—(CH₂)₂— | |
| —CH₂—CHOC₂H₅—(CH₂)₂— | |
| —CH₂—CHOC₃H₇—(CH₂)₂— | |

Emphasis should be given to the following compounds:

(I-1-a-1)

(I-1-a-2)

(I-1-a-3)

(I-1-a-4)

(I-1-a-5)

(I-1-a-6)

(I-1-a-7) 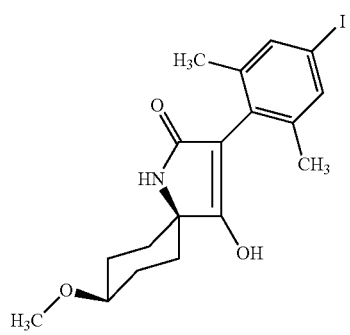
(I-1-a-8) 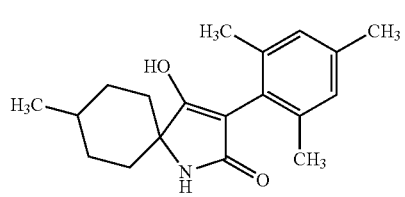
(I-1-a-9) 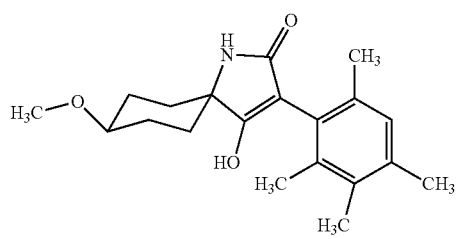
(I-1-a-10) 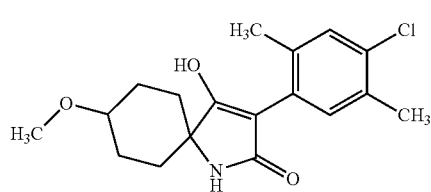
(I-1-a-11) 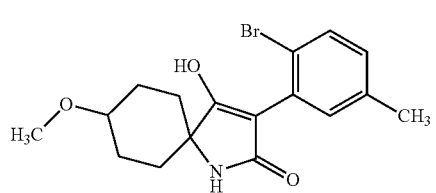
(I-1-a-12) 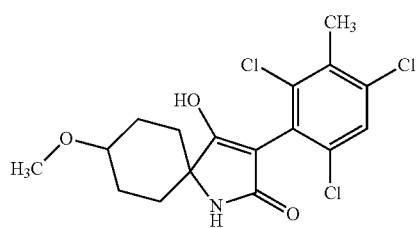
(I-1-a-13) 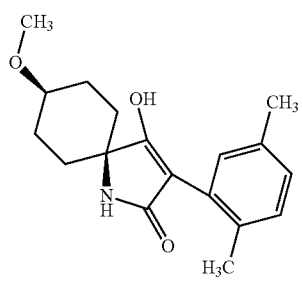
(I-1-a-14) 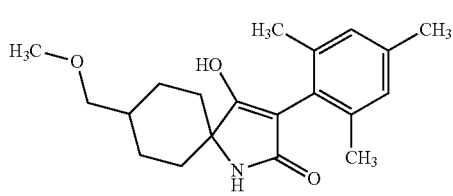
(I-1-a-15) 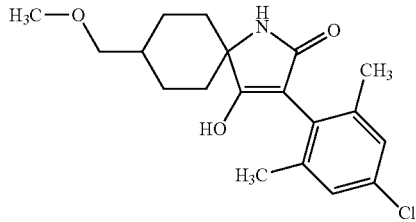
(I-1-a-16) 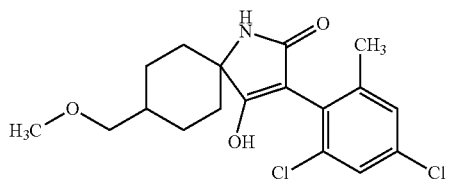
(I-1-a-17) 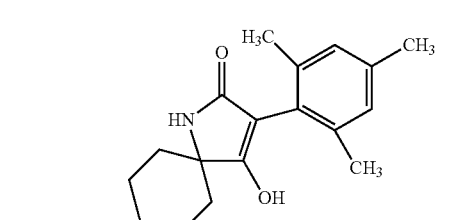
(I-1-a-18) 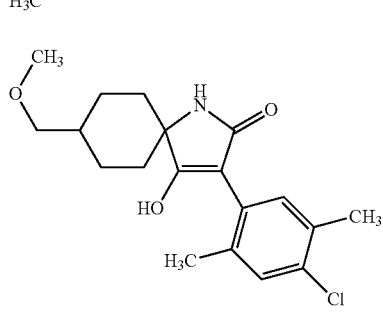

(I-1-c-1)
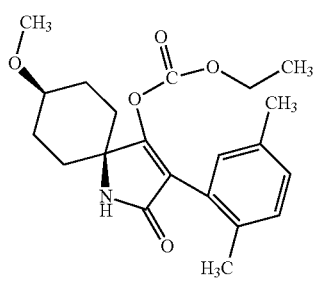
spirotetramat
(I-1-c-2)
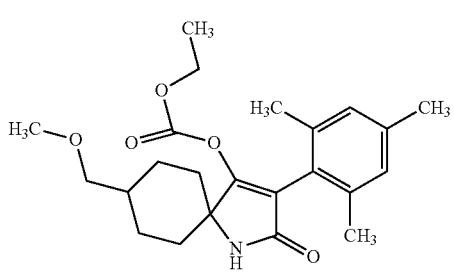
(I-2-a-1)
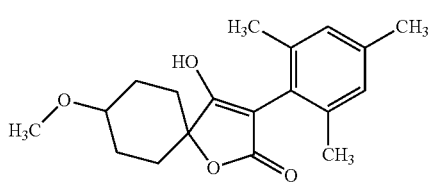
(I-2-a-2)
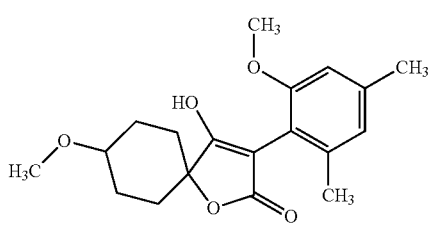
(I-2-a-3)
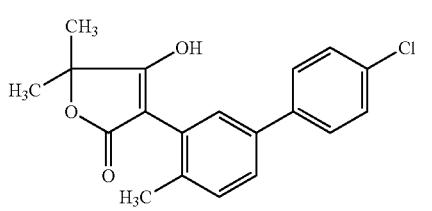
(I-2-a-4)
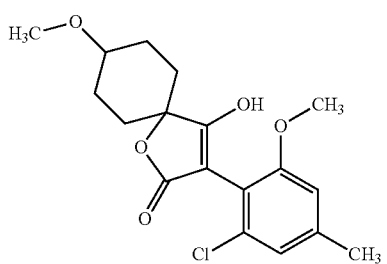
(I-2-b-1)
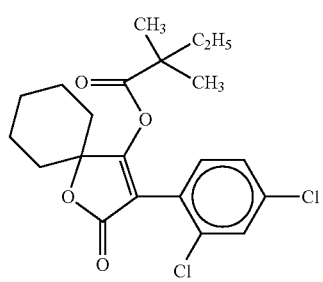
spirodiclofen
(I-2-b-2)
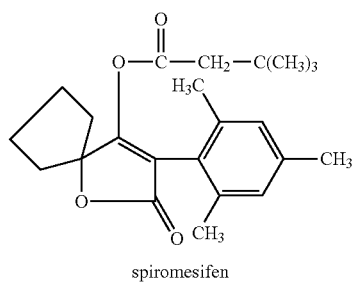
spiromesifen
(I-4-a-1)
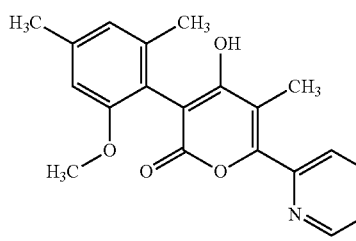
(I-4-a-2)
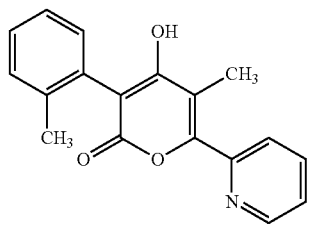
(I-4-a-3)
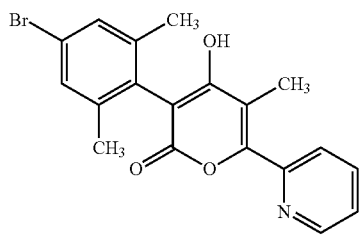
(I-5-a-1)
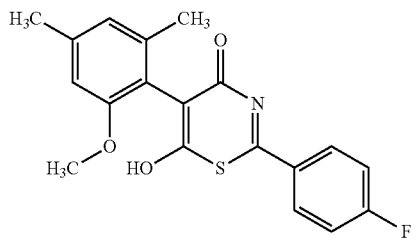

(I-6-a-1) 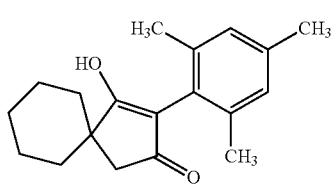

(I-6-a-2) 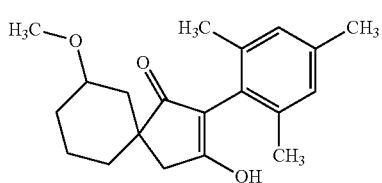

(I-8-a-1) 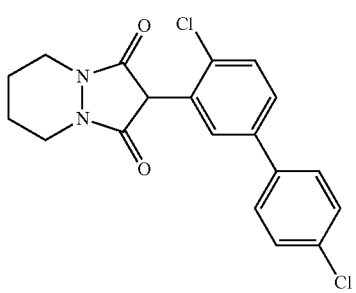

(I-8-a-2) 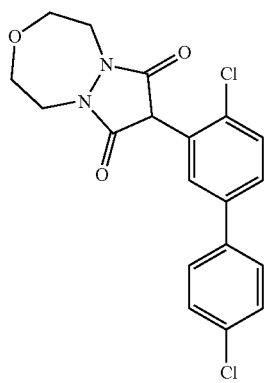

(I-8-a-3) 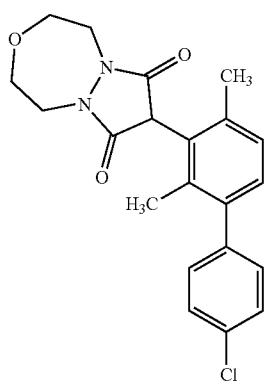

(I-8-a-4) 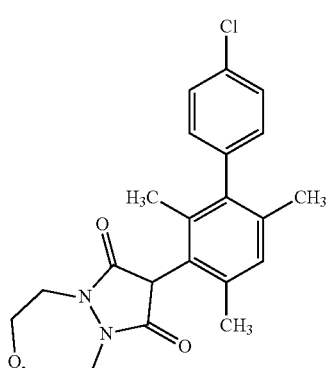

(I-9-a-1) 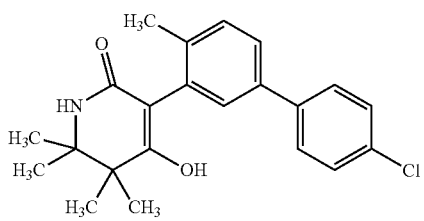

(I-10-a-1) 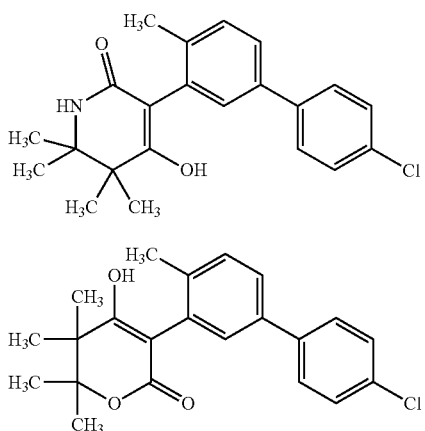

(I-10-a-2) 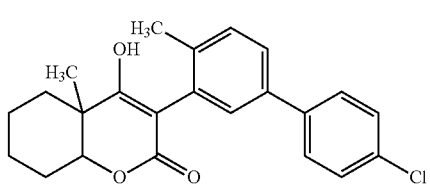

The compounds of the formula (I) possess a broad insecticidal and/or acaricidal activity, but individually the activity and/or plant tolerance leaves something to be desired.

The active ingredients can be used in the compositions of the invention in a broad concentration range. The concentration of the active ingredients in the formulation is typically 0.1%-50% by weight.

Ammonium salts and phosphonium salts which inventively boost the activity of crop protection materials comprising fatty acid biosynthesis inhibitors are defined by formula (II)

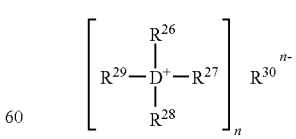

(II)

in which
D is nitrogen or phosphorus,
D is preferably nitrogen,
$R^{26}$, $R^{27}$, $R^{28}$ and $R^{29}$ independently of one another are hydrogen or in each case optionally substituted $C_1$-$C_8$-alkyl or singly or multiply unsaturated, optionally substituted $C_1$-$C_8$-alkylene, the substituents being selectable from halogen, nitro and cyano, $R^{26}$, $R^{27}$, $R^{28}$ and $R^{29}$ are preferably independently of one another hydrogen or in each case optionally substituted $C_1$-$C_4$-alkyl, the substituents being selectable from halogen, nitro and cyano, $R^{26}$, $R^{27}$, $R^{28}$ and $R^{29}$ are with particular preference independently of one another hydrogen, methyl, ethyl, n-propyl, isopropyl, n-butyl, isobutyl, sec-butyl or tert-butyl, $R^{26}$, $R^{27}$, $R^{21}$ and $R^{29}$ with very particular preference are hydrogen, $R^{26}$, $R^{27}$, $R^{28}$ and $R^{29}$, additionally, with very particular preference simultaneously are methyl or simultaneously are ethyl, n is 1, 2, 3 or 4, n preferably is 1 or 2, $R^{30}$ is an organic or inorganic anion, $R^{30}$ preferably is hydrogencarbonate, tetraborate, fluoride, bromide, iodide, chloride, monohydrogenphosphate, dihydrogenphosphate, hydrogensulphate, tartrate, sulphate, nitrate, thiosulphate, thiocyanate, formate, lactate, acetate, propionate, butyrate, pentanoate, citrate or oxalate, $R^{30}$ additionally preferably is carbonate, pentaborate, sulphite, benzoate, hydrogenoxalate, hydrogencitrate, methylsulphate or tetrafluoroborate, $R^{30}$ with particular preference is lactate, sulphate, nitrate, thiosulphate, thiocyanate, citrate, oxalate or formate, $R^{30}$ moreover with particular preference is monohydrogenphosphate or dihydrogenphosphate, and $R^{30}$ with very particular preference is thiocyanate, dihydrogenphosphate, monohydrogenphosphate, or sulphate.

The ammonium salts and phosphonium salts of the formula (II) can be used in a broad concentration range to boost the activity of crop protection materials comprising ketoenols. In general the ammonium salts or phosphonium salts are used in the application-ready crop protection material in a concentration of 0.5 to 80 mmol/l, preferably 0.75 to 37.5 mmol/l, more preferably 1.5 to 25 mmol/l. In the case of the formulated product the ammonium salt and/or phosphonium salt concentration in the formulation is chosen such that it is within these stated general, preferred or particularly preferred ranges after the formulation has been diluted to the desired active-ingredient concentration. The concentration of the salt in the formulation is typically 1%-50% by weight.

In one preferred embodiment of the invention the activity is boosted by adding to the crop protection materials not only an ammonium salt and/or phosphonium salt but also, additionally, a penetrant. It is considered entirely surprising that even in these cases an even greater boost to activity is observed. The present invention therefore likewise provides for the use of a combination of penetrant and ammonium salts and/or phosphonium salts to boost the activity crop protection materials which comprise insecticidally active phenyl-substituted cyclic ketoenols as active ingredient. The invention likewise provides materials which comprise insecticidally active phenyl-substituted cyclic ketoenols, penetrants and ammonium salts and/or phosphonium salts, including specifically not only formulated active ingredients but also application-ready materials (spray liquors). The invention additionally provides, finally, for the use of these materials for controlling parasitic insects.

Suitable penetrants in the present context include all those substances which are typically used to enhance the penetration of active agrochemical ingredients into plants. Penetrants are defined in this context by their ability to penetrate from the aqueous spray liquor and/or from the spray coating into the cuticle of the plant and thereby to increase the mobility of active ingredients in the cuticle. The method described in the literature (Baur et al., 1997, *Pesticide Science* 51, 131-152) can be used in order to determine this property.

Examples of suitable penetrants include alkanol alkoxylates. Penetrants of the invention are alkanol alkoxylates of the formula

(III)

in which

R is linear or branched alkyl having 4 to 20 carbon atoms,

R' is hydrogen, methyl, ethyl, n-propyl, isopropyl, n-butyl, isobutyl, tert-butyl, n-pentyl or n-hexyl, AO is an ethylene oxide radical, a propylene oxide radical, a butylene oxide radical or is mixtures of ethylene oxide and propylene oxide radicals or butylene oxide radicals, and v is a number from 2 to 30.

One preferred group of penetrants are alkanol alkoxylates of the formula

(III-a)

in which

R is as defined above,

R' is as defined above,

EO is —$CH_2$—$CH_2$—O—, and n is a number from 2 to 20.

A further preferred group of penetrants are alkanol alkoxylates of the formula

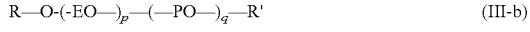

(III-b)

in which

R is as defined above,

R' is as defined above,

EO is —$CH_2$—$CH_2$—O—,

PO is

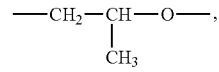

p is a number from 1 to 10, and q is a number from 1 to 10.

A further preferred group of penetrants are alkanol alkoxylates of the formula

(III-c)

in which

R is as defined above,

R' is as defined above,

EO is —$CH_2$—$CH_2$—O—,

PO is

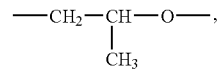

r is a number from 1 to 10, and s is a number from 1 to 10.

A further preferred group of penetrants are alkanol alkoxylates of the formula

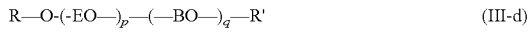

(III-d)

in which
R and R' are as defined above,
EO is $CH_2-CH_2-O-$,
BO is

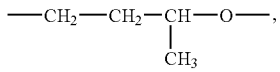

p is a number from 1 to 10 and
q is a number from 1 to 10.

A further preferred group of penetrants are alkanol alkoxylates of the formula $$R-O-(-BO-)_r-(-EO-)_s-R' \qquad \text{(III-e)}$$

in which
R and R' are as defined above,
BO is

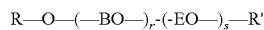

EO is $CH_2-CH_2-O-$,
r is a number from 1 to 10 and
s is a number from 1 to 10.

A further preferred group of penetrants are alkanol alkoxylates of the formula $$CH_3-(CH_2)_t-CH_2-O-(-CH_2-CH_2-O-)_u-R' \qquad \text{(III-f)}$$

in which
R' is as defined above,
t is a number from 8 to 13,
u is a number from 6 to 17.

In the formulae indicated above,
R is preferably butyl, isobutyl, n-pentyl, isopentyl, neopentyl, n-hexyl, isohexyl, n-octyl, isooctyl, 2-ethylhexyl, nonyl, isononyl, decyl, n-dodecyl, isododecyl, lauryl, myristyl, isotridecyl, trimethylnonyl, palmityl, stearyl or eicosyl.

As an example of an alkanol alkoxylate of the formula (III-c) mention may be made of 2-ethylhexyl alkoxylate of the formula

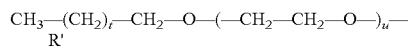

in which
EO is $-CH_2-CH_2-O-$,
PO is

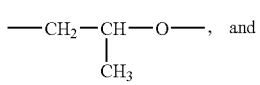

the numbers 8 and 6 represent average values.

As an example of an alkanol alkoxylate of the formula (III-d) mention may be made of the formula

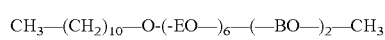

in which
EO is $CH_2-CH_2-O-$,
BO is

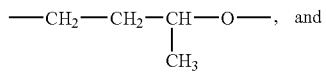

the numbers 10, 6 and 2 represent average values.

Particularly preferred alkanol alkoxylates of the formula (III-f) are compounds of this formula in which
t is a number from 9 to 12 and
u is a number from 7 to 9.

Mention may be made with very particular preference of alkanol alkoxylate of the formula (III-f-1)

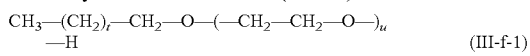

in which
t stands for the average value 10.5 and
u stands for the average value 8.4.

A general definition of the alkanol alkoxylates is given by the formulae above. These substances are mixtures of substances of the stated type with different chain lengths. The indices therefore have average values which may also deviate from whole numbers.

The alkanol alkoxylates of the formulae stated are known and in some cases are available commercially or can be prepared by known methods (cf. WO 98-35 553, WO 00-35 278 and EP-A 0 681 865).

Suitable penetrants also include, for example, substances which promote the availability of the compounds of the formula (I) in the spray coating. These include, for example, mineral or vegetable oils. Suitable oils are all mineral or vegetable oils—modified or otherwise—which can typically be used in agrochemical compositions. Mention may be made by way of example of sunflower oil, rapeseed oil, olive oil, castor oil, colza oil, maize seed oil, cotton seed oil and soybean oil, or the esters of said oils. Preference is given to rapeseed oil, sunflower oil and their methyl or ethyl esters.

The concentration of penetrant in the materials of the invention can be varied within a wide range. In the case of a formulated crop protection material it is in general 1% to 95%, preferably 1% to 55%, more preferably 15%-40% by weight. In the application-ready materials (spray liquors) the concentrations are generally between 0.1 and 10 g/l, preferably between 0.5 and 5 g/l.

Inventively emphasized combinations of active ingredient, salt and penetrant are listed in the table below. "as per test" means here that any compound that acts as a penetrant in the cuticle penetration test (Baur et al., 1997, *Pesticide Science* 51, 131-152) is suitable.

| # | Active ingredient | Salt | Penetrant |
|---|---|---|---|
| 1 | (I-1-a-1) | ammonium sulphate | as per test |
| 2 | (I-1-a-1) | ammonium lactate | as per test |
| 3 | (I-1-a-1) | ammonium nitrate | as per test |
| 4 | (I-1-a-1) | ammonium thiosulphate | as per test |
| 5 | (I-1-a-1) | ammonium thiocyanate | as per test |
| 6 | (I-1-a-1) | ammonium citrate | as per test |
| 7 | (I-1-a-1) | ammonium oxalate | as per test |
| 8 | (I-1-a-1) | ammonium formate | as per test |
| 9 | (I-1-a-1) | ammonium hydrogenphosphate | as per test |
| 10 | (I-1-a-1) | ammonium dihydrogenphosphate | as per test |
| 11 | (I-1-a-1) | ammonium carbonate | as per test |

| # | Active ingredient | Salt | Penetrant |
|---|---|---|---|
| 12 | (I-1-a-1) | ammonium benzoate | as per test |
| 13 | (I-1-a-1) | ammonium sulphite | as per test |
| 14 | (I-1-a-1) | ammonium benzoate | as per test |
| 15 | (I-1-a-1) | ammonium hydrogenoxalate | as per test |
| 16 | (I-1-a-1) | ammonium hydrogencitrate | as per test |
| 17 | (I-1-a-1) | ammonium acetate | as per test |
| 18 | (I-1-a-1) | tetramethylammonium sulphate | as per test |
| 19 | (I-1-a-1) | tetramethylammonium lactate | as per test |
| 20 | (I-1-a-1) | tetramethylammonium nitrate | as per test |
| 21 | (I-1-a-1) | tetramethylammonium thiosulphate | as per test |
| 22 | (I-1-a-1) | tetramethylammonium thiocyanate | as per test |
| 23 | (I-1-a-1) | tetramethylammonium citrate | as per test |
| 24 | (I-1-a-1) | tetramethylammonium oxalate | as per test |
| 25 | (I-1-a-1) | tetramethylammonium formate | as per test |
| 26 | (I-1-a-1) | tetramethylammonium hydrogenphosphate | as per test |
| 27 | (I-1-a-1) | tetramethylammonium dihydrogenphosphate | as per test |
| 28 | (I-1-a-1) | tetraethylammonium sulphate | as per test |
| 29 | (I-1-a-1) | tetraethylammonium lactate | as per test |
| 30 | (I-1-a-1) | tetraethylammonium nitrate | as per test |
| 31 | (I-1-a-1) | tetraethylammonium thiosulphate | as per test |
| 32 | (I-1-a-1) | tetraethylammonium thiocyanate | as per test |
| 33 | (I-1-a-1) | tetraethylammonium citrate | as per test |
| 34 | (I-1-a-1) | tetraethylammonium oxalate | as per test |
| 35 | (I-1-a-1) | tetraethylammonium formate | as per test |
| 36 | (I-1-a-1) | tetraethylammonium hydrogenphosphate | as per test |
| 37 | (I-1-a-1) | tetraethylammonium dihydrogenphosphate | as per test |
| 38 | (I-1-a-2) | ammonium sulphate | as per test |
| 39 | (I-1-a-2) | ammonium lactate | as per test |
| 40 | (I-1-a-2) | ammonium nitrate | as per test |
| 41 | (I-1-a-2) | ammonium thiosulphate | as per test |
| 42 | (I-1-a-2) | ammonium thiocyanate | as per test |
| 43 | (I-1-a-2) | ammonium citrate | as per test |
| 44 | (I-1-a-2) | ammonium oxalate | as per test |
| 45 | (I-1-a-2) | ammonium formate | as per test |
| 46 | (I-1-a-2) | ammonium hydrogenphosphate | as per test |
| 47 | (I-1-a-2) | ammonium dihydrogenphosphate | as per test |
| 48 | (I-1-a-2) | ammonium carbonate | as per test |
| 49 | (I-1-a-2) | ammonium benzoate | as per test |
| 50 | (I-1-a-2) | ammonium sulphite | as per test |
| 51 | (I-1-a-2) | ammonium benzoate | as per test |
| 52 | (I-1-a-2) | ammonium hydrogenoxalate | as per test |
| 53 | (I-1-a-2) | ammonium hydrogencitrate | as per test |
| 54 | (I-1-a-2) | ammonium acetate | as per test |
| 55 | (I-1-a-2) | tetramethylammonium sulphate | as per test |
| 56 | (I-1-a-2) | tetramethylammonium lactate | as per test |
| 57 | (I-1-a-2) | tetramethylammonium nitrate | as per test |
| 58 | (I-1-a-2) | tetramethylammonium thiosulphate | as per test |
| 59 | (I-1-a-2) | tetramethylammonium thiocyanate | as per test |
| 60 | (I-1-a-2) | tetramethylammonium citrate | as per test |
| 61 | (I-1-a-2) | tetramethylammonium oxalate | as per test |
| 62 | (I-1-a-2) | tetramethylammonium formate | as per test |
| 63 | (I-1-a-2) | tetramethylammonium hydrogenphosphate | as per test |
| 64 | (I-1-a-2) | tetramethylammonium dihydrogenphosphate | as per test |
| 65 | (I-1-a-2) | tetraethylammonium sulphate | as per test |
| 66 | (I-1-a-2) | tetraethylammonium lactate | as per test |
| 67 | (I-1-a-2) | tetraethylammonium nitrate | as per test |
| 68 | (I-1-a-2) | tetraethylammonium thiosulphate | as per test |
| 69 | (I-1-a-2) | tetraethylammonium thiocyanate | as per test |
| 70 | (I-1-a-2) | tetraethylammonium citrate | as per test |
| 71 | (I-1-a-2) | tetraethylammonium oxalate | as per test |
| 72 | (I-1-a-2) | tetraethylammonium formate | as per test |
| 73 | (I-1-a-2) | tetraethylammonium hydrogenphosphate | as per test |
| 74 | (I-1-a-2) | tetraethylammonium dihydrogenphosphate | as per test |
| 75 | (I-1-a-3) | ammonium sulphate | as per test |
| 76 | (I-1-a-3) | ammonium lactate | as per test |
| 77 | (I-1-a-3) | ammonium nitrate | as per test |
| 78 | (I-1-a-3) | ammonium thiosulphate | as per test |
| 79 | (I-1-a-3) | ammonium thiocyanate | as per test |
| 80 | (I-1-a-3) | ammonium citrate | as per test |
| 81 | (I-1-a-3) | ammonium oxalate | as per test |
| 82 | (I-1-a-3) | ammonium formate | as per test |
| 83 | (I-1-a-3) | ammonium hydrogenphosphate | as per test |
| 84 | (I-1-a-3) | ammonium dihydrogenphosphate | as per test |
| 85 | (I-1-a-3) | ammonium carbonate | as per test |
| 86 | (I-1-a-3) | ammonium benzoate | as per test |
| 87 | (I-1-a-3) | ammonium sulphite | as per test |
| 88 | (I-1-a-3) | ammonium benzoate | as per test |
| 89 | (I-1-a-3) | ammonium hydrogenoxalate | as per test |
| 90 | (I-1-a-3) | ammonium hydrogencitrate | as per test |
| 91 | (I-1-a-3) | ammonium acetate | as per test |
| 92 | (I-1-a-3) | tetramethylammonium sulphate | as per test |
| 93 | (I-1-a-3) | tetramethylammonium lactate | as per test |
| 94 | (I-1-a-3) | tetramethylammonium nitrate | as per test |
| 95 | (I-1-a-3) | tetramethylammonium thiosulphate | as per test |
| 96 | (I-1-a-3) | tetramethylammonium thiocyanate | as per test |
| 97 | (I-1-a-3) | tetramethylammonium citrate | as per test |
| 98 | (I-1-a-3) | tetramethylammonium oxalate | as per test |
| 99 | (I-1-a-3) | tetramethylammonium formate | as per test |
| 100 | (I-1-a-3) | tetramethylammonium hydrogenphosphate | as per test |
| 101 | (I-1-a-3) | tetramethylammonium dihydrogenphosphate | as per test |
| 102 | (I-1-a-3) | tetraethylammonium sulphate | as per test |
| 103 | (I-1-a-3) | tetraethylammonium lactate | as per test |
| 104 | (I-1-a-3) | tetraethylammonium nitrate | as per test |
| 105 | (I-1-a-3) | tetraethylammonium thiosulphate | as per test |
| 106 | (I-1-a-3) | tetraethylammonium thiocyanate | as per test |
| 107 | (I-1-a-3) | tetraethylammonium citrate | as per test |
| 108 | (I-1-a-3) | tetraethylammonium oxalate | as per test |
| 109 | (I-1-a-3) | tetraethylammonium formate | as per test |
| 110 | (I-1-a-3) | tetraethylammonium hydrogenphosphate | as per test |
| 111 | (I-1-a-3) | tetraethylammonium dihydrogenphosphate | as per test |
| 112 | (I-1-a-4) | ammonium sulphate | as per test |
| 113 | (I-1-a-4) | ammonium lactate | as per test |
| 114 | (I-1-a-4) | ammonium nitrate | as per test |
| 115 | (I-1-a-4) | ammonium thiosulphate | as per test |
| 116 | (I-1-a-4) | ammonium thiocyanate | as per test |
| 117 | (I-1-a-4) | ammonium citrate | as per test |
| 118 | (I-1-a-4) | ammonium oxalate | as per test |
| 119 | (I-1-a-4) | ammonium formate | as per test |
| 120 | (I-1-a-4) | ammonium hydrogenphosphate | as per test |
| 121 | (I-1-a-4) | ammonium dihydrogenphosphate | as per test |
| 122 | (I-1-a-4) | ammonium carbonate | as per test |
| 123 | (I-1-a-4) | ammonium benzoate | as per test |
| 124 | (I-1-a-4) | ammonium sulphite | as per test |
| 125 | (I-1-a-4) | ammonium benzoate | as per test |
| 126 | (I-1-a-4) | ammonium hydrogenoxalate | as per test |
| 127 | (I-1-a-4) | ammonium hydrogencitrate | as per test |
| 128 | (I-1-a-4) | ammonium acetate | as per test |
| 129 | (I-1-a-4) | tetramethylammonium sulphate | as per test |
| 130 | (I-1-a-4) | tetramethylammonium lactate | as per test |
| 131 | (I-1-a-4) | tetramethylammonium nitrate | as per test |
| 132 | (I-1-a-4) | tetramethylammonium thiosulphate | as per test |
| 133 | (I-1-a-4) | tetramethylammonium thiocyanate | as per test |
| 134 | (I-1-a-4) | tetramethylammonium citrate | as per test |
| 135 | (I-1-a-4) | tetramethylammonium oxalate | as per test |
| 136 | (I-1-a-4) | tetramethylammonium formate | as per test |
| 137 | (I-1-a-4) | tetramethylammonium hydrogenphosphate | as per test |
| 138 | (I-1-a-4) | tetramethylammonium dihydrogenphosphate | as per test |
| 139 | (I-1-a-4) | tetraethylammonium sulphate | as per test |
| 140 | (I-1-a-4) | tetraethylammonium lactate | as per test |
| 141 | (I-1-a-4) | tetraethylammonium nitrate | as per test |
| 142 | (I-1-a-4) | tetraethylammonium thiosulphate | as per test |
| 143 | (I-1-a-4) | tetraethylammonium thiocyanate | as per test |
| 144 | (I-1-a-4) | tetraethylammonium citrate | as per test |
| 145 | (I-1-a-4) | tetraethylammonium oxalate | as per test |
| 146 | (I-1-a-4) | tetraethylammonium formate | as per test |
| 147 | (I-1-a-4) | tetraethylammonium hydrogenphosphate | as per test |
| 148 | (I-1-a-4) | tetraethylammonium dihydrogenphosphate | as per test |
| 149 | (I-1-a-5) | ammonium sulphate | as per test |
| 150 | (I-1-a-5) | ammonium lactate | as per test |
| 151 | (I-1-a-5) | ammonium nitrate | as per test |
| 152 | (I-1-a-5) | ammonium thiosulphate | as per test |
| 153 | (I-1-a-5) | ammonium thiocyanate | as per test |
| 154 | (I-1-a-5) | ammonium citrate | as per test |
| 155 | (I-1-a-5) | ammonium oxalate | as per test |
| 156 | (I-1-a-5) | ammonium formate | as per test |
| 157 | (I-1-a-5) | ammonium hydrogenphosphate | as per test |
| 158 | (I-1-a-5) | ammonium dihydrogenphosphate | as per test |
| 159 | (I-1-a-5) | ammonium carbonate | as per test |
| 160 | (I-1-a-5) | ammonium benzoate | as per test |
| 161 | (I-1-a-5) | ammonium sulphite | as per test |

| # | Active ingredient | Salt | Penetrant |
|---|---|---|---|
| 162 | (I-1-a-5) | ammonium benzoate | as per test |
| 163 | (I-1-a-5) | ammonium hydrogenoxalate | as per test |
| 164 | (I-1-a-5) | ammonium hydrogencitrate | as per test |
| 165 | (I-1-a-5) | ammonium acetate | as per test |
| 166 | (I-1-a-5) | tetramethylammonium sulphate | as per test |
| 167 | (I-1-a-5) | tetramethylammonium lactate | as per test |
| 168 | (I-1-a-5) | tetramethylammonium nitrate | as per test |
| 169 | (I-1-a-5) | tetramethylammonium thiosulphate | as per test |
| 170 | (I-1-a-5) | tetramethylammonium thiocyanate | as per test |
| 171 | (I-1-a-5) | tetramethylammonium citrate | as per test |
| 172 | (I-1-a-5) | tetramethylammonium oxalate | as per test |
| 173 | (I-1-a-5) | tetramethylammonium formate | as per test |
| 174 | (I-1-a-5) | tetramethylammonium hydrogenphosphate | as per test |
| 175 | (I-1-a-5) | tetramethylammonium dihydrogenphosphate | as per test |
| 176 | (I-1-a-5) | tetraethylammonium sulphate | as per test |
| 177 | (I-1-a-5) | tetraethylammonium lactate | as per test |
| 178 | (I-1-a-5) | tetraethylammonium nitrate | as per test |
| 179 | (I-1-a-5) | tetraethylammonium thiosulphate | as per test |
| 180 | (I-1-a-5) | tetraethylammonium thiocyanate | as per test |
| 181 | (I-1-a-5) | tetraethylammonium citrate | as per test |
| 182 | (I-1-a-5) | tetraethylammonium oxalate | as per test |
| 183 | (I-1-a-5) | tetraethylammonium formate | as per test |
| 184 | (I-1-a-5) | tetraethylammonium hydrogenphosphate | as per test |
| 185 | (I-1-a-5) | tetraethylammonium dihydrogenphosphate | as per test |
| 186 | (I-1-a-6) | ammonium sulphate | as per test |
| 187 | (I-1-a-6) | ammonium lactate | as per test |
| 188 | (I-1-a-6) | ammonium nitrate | as per test |
| 189 | (I-1-a-6) | ammonium thiosulphate | as per test |
| 190 | (I-1-a-6) | ammonium thiocyanate | as per test |
| 191 | (I-1-a-6) | ammonium citrate | as per test |
| 192 | (I-1-a-6) | ammonium oxalate | as per test |
| 193 | (I-1-a-6) | ammonium formate | as per test |
| 194 | (I-1-a-6) | ammonium hydrogenphosphate | as per test |
| 195 | (I-1-a-6) | ammonium dihydrogenphosphate | as per test |
| 196 | (I-1-a-6) | ammonium carbonate | as per test |
| 197 | (I-1-a-6) | ammonium benzoate | as per test |
| 198 | (I-1-a-6) | ammonium sulphite | as per test |
| 199 | (I-1-a-6) | ammonium benzoate | as per test |
| 200 | (I-1-a-6) | ammonium hydrogenoxalate | as per test |
| 201 | (I-1-a-6) | ammonium hydrogencitrate | as per test |
| 202 | (I-1-a-6) | ammonium acetate | as per test |
| 203 | (I-1-a-6) | tetramethylammonium sulphate | as per test |
| 204 | (I-1-a-6) | tetramethylammonium lactate | as per test |
| 205 | (I-1-a-6) | tetramethylammonium nitrate | as per test |
| 206 | (I-1-a-6) | tetramethylammonium thiosulphate | as per test |
| 207 | (I-1-a-6) | tetramethylammonium thiocyanate | as per test |
| 208 | (I-1-a-6) | tetramethylammonium citrate | as per test |
| 209 | (I-1-a-6) | tetramethylammonium oxalate | as per test |
| 210 | (I-1-a-6) | tetramethylammonium formate | as per test |
| 211 | (I-1-a-6) | tetramethylammonium hydrogenphosphate | as per test |
| 212 | (I-1-a-6) | tetramethylammonium dihydrogenphosphate | as per test |
| 213 | (I-1-a-6) | tetraethylammonium sulphate | as per test |
| 214 | (I-1-a-6) | tetraethylammonium lactate | as per test |
| 215 | (I-1-a-6) | tetraethylammonium nitrate | as per test |
| 216 | (I-1-a-6) | tetraethylammonium thiosulphate | as per test |
| 217 | (I-1-a-6) | tetraethylammonium thiocyanate | as per test |
| 218 | (I-1-a-6) | tetraethylammonium citrate | as per test |
| 219 | (I-1-a-6) | tetraethylammonium oxalate | as per test |
| 220 | (I-1-a-6) | tetraethylammonium formate | as per test |
| 221 | (I-1-a-6) | tetraethylammonium hydrogenphosphate | as per test |
| 222 | (I-1-a-6) | tetraethylammonium dihydrogenphosphate | as per test |
| 223 | (I-1-a-7) | ammonium sulphate | as per test |
| 224 | (I-1-a-7) | ammonium lactate | as per test |
| 225 | (I-1-a-7) | ammonium nitrate | as per test |
| 226 | (I-1-a-7) | ammonium thiosulphate | as per test |
| 227 | (I-1-a-7) | ammonium thiocyanate | as per test |
| 228 | (I-1-a-7) | ammonium citrate | as per test |
| 229 | (I-1-a-7) | ammonium oxalate | as per test |
| 230 | (I-1-a-7) | ammonium formate | as per test |
| 231 | (I-1-a-7) | ammonium hydrogenphosphate | as per test |
| 232 | (I-1-a-7) | ammonium dihydrogenphosphate | as per test |
| 233 | (I-1-a-7) | ammonium carbonate | as per test |
| 234 | (I-1-a-7) | ammonium benzoate | as per test |
| 235 | (I-1-a-7) | ammonium sulphite | as per test |
| 236 | (I-1-a-7) | ammonium benzoate | as per test |
| 237 | (I-1-a-7) | ammonium hydrogenoxalate | as per test |
| 238 | (I-1-a-7) | ammonium hydrogencitrate | as per test |
| 239 | (I-1-a-7) | ammonium acetate | as per test |
| 240 | (I-1-a-7) | tetramethylammonium sulphate | as per test |
| 241 | (I-1-a-7) | tetramethylammonium lactate | as per test |
| 242 | (I-1-a-7) | tetramethylammonium nitrate | as per test |
| 243 | (I-1-a-7) | tetramethylammonium thiosulphate | as per test |
| 244 | (I-1-a-7) | tetramethylammonium thiocyanate | as per test |
| 245 | (I-1-a-7) | tetramethylammonium citrate | as per test |
| 246 | (I-1-a-7) | tetramethylammonium oxalate | as per test |
| 247 | (I-1-a-7) | tetramethylammonium formate | as per test |
| 248 | (I-1-a-7) | tetramethylammonium hydrogenphosphate | as per test |
| 249 | (I-1-a-7) | tetramethylammonium dihydrogenphosphate | as per test |
| 250 | (I-1-a-7) | tetraethylammonium sulphate | as per test |
| 251 | (I-1-a-7) | tetraethylammonium lactate | as per test |
| 252 | (I-1-a-7) | tetraethylammonium nitrate | as per test |
| 253 | (I-1-a-7) | tetraethylammonium thiosulphate | as per test |
| 254 | (I-1-a-7) | tetraethylammonium thiocyanate | as per test |
| 255 | (I-1-a-7) | tetraethylammonium citrate | as per test |
| 256 | (I-1-a-7) | tetraethylammonium oxalate | as per test |
| 257 | (I-1-a-7) | tetraethylammonium formate | as per test |
| 258 | (I-1-a-7) | tetraethylammonium hydrogenphosphate | as per test |
| 259 | (I-1-a-7) | tetraethylammonium dihydrogenphosphate | as per test |
| 260 | (I-1-a-8) | ammonium sulphate | as per test |
| 261 | (I-1-a-8) | ammonium lactate | as per test |
| 262 | (I-1-a-8) | ammonium nitrate | as per test |
| 263 | (I-1-a-8) | ammonium thiosulphate | as per test |
| 264 | (I-1-a-8) | ammonium thiocyanate | as per test |
| 265 | (I-1-a-8) | ammonium citrate | as per test |
| 266 | (I-1-a-8) | ammonium oxalate | as per test |
| 267 | (I-1-a-8) | ammonium formate | as per test |
| 268 | (I-1-a-8) | ammonium hydrogenphosphate | as per test |
| 269 | (I-1-a-8) | ammonium dihydrogenphosphate | as per test |
| 270 | (I-1-a-8) | ammonium carbonate | as per test |
| 271 | (I-1-a-8) | ammonium benzoate | as per test |
| 272 | (I-1-a-8) | ammonium sulphite | as per test |
| 273 | (I-1-a-8) | ammonium benzoate | as per test |
| 274 | (I-1-a-8) | ammonium hydrogenoxalate | as per test |
| 275 | (I-1-a-8) | ammonium hydrogencitrate | as per test |
| 276 | (I-1-a-8) | ammonium acetate | as per test |
| 277 | (I-1-a-8) | tetramethylammonium sulphate | as per test |
| 278 | (I-1-a-8) | tetramethylammonium lactate | as per test |
| 279 | (I-1-a-8) | tetramethylammonium nitrate | as per test |
| 280 | (I-1-a-8) | tetramethylammonium thiosulphate | as per test |
| 281 | (I-1-a-8) | tetramethylammonium thiocyanate | as per test |
| 282 | (I-1-a-8) | tetramethylammonium citrate | as per test |
| 283 | (I-1-a-8) | tetramethylammonium oxalate | as per test |
| 284 | (I-1-a-8) | tetramethylammonium formate | as per test |
| 285 | (I-1-a-8) | tetramethylammonium hydrogenphosphate | as per test |
| 286 | (I-1-a-8) | tetramethylammonium dihydrogenphosphate | as per test |
| 287 | (I-1-a-8) | tetraethylammonium sulphate | as per test |
| 288 | (I-1-a-8) | tetraethylammonium lactate | as per test |
| 289 | (I-1-a-8) | tetraethylammonium nitrate | as per test |
| 290 | (I-1-a-8) | tetraethylammonium thiosulphate | as per test |
| 291 | (I-1-a-8) | tetraethylammonium thiocyanate | as per test |
| 292 | (I-1-a-8) | tetraethylammonium citrate | as per test |
| 293 | (I-1-a-8) | tetraethylammonium oxalate | as per test |
| 294 | (I-1-a-8) | tetraethylammonium formate | as per test |
| 295 | (I-1-a-8) | tetraethylammonium hydrogenphosphate | as per test |
| 296 | (I-1-a-8) | tetraethylammonium dihydrogenphosphate | as per test |
| 297 | (I-1-a-9) | ammonium sulphate | as per test |
| 298 | (I-1-a-9) | ammonium lactate | as per test |
| 299 | (I-1-a-9) | ammonium nitrate | as per test |
| 300 | (I-1-a-9) | ammonium thiosulphate | as per test |
| 301 | (I-1-a-9) | ammonium thiocyanate | as per test |
| 302 | (I-1-a-9) | ammonium citrate | as per test |
| 303 | (I-1-a-9) | ammonium oxalate | as per test |
| 304 | (I-1-a-9) | ammonium formate | as per test |
| 305 | (I-1-a-9) | ammonium hydrogenphosphate | as per test |
| 306 | (I-1-a-9) | ammonium dihydrogenphosphate | as per test |
| 307 | (I-1-a-9) | ammonium carbonate | as per test |
| 308 | (I-1-a-9) | ammonium benzoate | as per test |
| 309 | (I-1-a-9) | ammonium sulphite | as per test |
| 310 | (I-1-a-9) | ammonium benzoate | as per test |
| 311 | (I-1-a-9) | ammonium hydrogenoxalate | as per test |

-continued

| # | Active ingredient | Salt | Penetrant |
|---|---|---|---|
| 312 | (I-1-a-9) | ammonium hydrogencitrate | as per test |
| 313 | (I-1-a-9) | ammonium acetate | as per test |
| 314 | (I-1-a-9) | tetramethylammonium sulphate | as per test |
| 315 | (I-1-a-9) | tetramethylammonium lactate | as per test |
| 316 | (I-1-a-9) | tetramethylammonium nitrate | as per test |
| 317 | (I-1-a-9) | tetramethylammonium thiosulphate | as per test |
| 318 | (I-1-a-9) | tetramethylammonium thiocyanate | as per test |
| 319 | (I-1-a-9) | tetramethylammonium citrate | as per test |
| 320 | (I-1-a-9) | tetramethylammonium oxalate | as per test |
| 321 | (I-1-a-9) | tetramethylammonium formate | as per test |
| 322 | (I-1-a-9) | tetramethylammonium hydrogenphosphate | as per test |
| 323 | (I-1-a-9) | tetramethylammonium dihydrogenphosphate | as per test |
| 324 | (I-1-a-9) | tetraethylammonium sulphate | as per test |
| 325 | (I-1-a-9) | tetraethylammonium lactate | as per test |
| 326 | (I-1-a-9) | tetraethylammonium nitrate | as per test |
| 327 | (I-1-a-9) | tetraethylammonium thiosulphate | as per test |
| 328 | (I-1-a-9) | tetraethylammonium thiocyanate | as per test |
| 329 | (I-1-a-9) | tetraethylammonium citrate | as per test |
| 330 | (I-1-a-9) | tetraethylammonium oxalate | as per test |
| 331 | (I-1-a-9) | tetraethylammonium formate | as per test |
| 332 | (I-1-a-9) | tetraethylammonium hydrogenphosphate | as per test |
| 333 | (I-1-a-9) | tetraethylammonium dihydrogenphosphate | as per test |
| 334 | (I-1-a-10) | ammonium sulphate | as per test |
| 335 | (I-1-a-10) | ammonium lactate | as per test |
| 336 | (I-1-a-10) | ammonium nitrate | as per test |
| 337 | (I-1-a-10) | ammonium thiosulphate | as per test |
| 338 | (I-1-a-10) | ammonium thiocyanate | as per test |
| 339 | (I-1-a-10) | ammonium citrate | as per test |
| 340 | (I-1-a-10) | ammonium oxalate | as per test |
| 341 | (I-1-a-10) | ammonium formate | as per test |
| 342 | (I-1-a-10) | ammonium hydrogenphosphate | as per test |
| 343 | (I-1-a-10) | ammonium dihydrogenphosphate | as per test |
| 344 | (I-1-a-10) | ammonium carbonate | as per test |
| 345 | (I-1-a-10) | ammonium benzoate | as per test |
| 346 | (I-1-a-10) | ammonium sulphite | as per test |
| 347 | (I-1-a-10) | ammonium benzoate | as per test |
| 348 | (I-1-a-10) | ammonium hydrogenoxalate | as per test |
| 349 | (I-1-a-10) | ammonium hydrogencitrate | as per test |
| 350 | (I-1-a-10) | ammonium acetate | as per test |
| 351 | (I-1-a-10) | tetramethylammonium sulphate | as per test |
| 352 | (I-1-a-10) | tetramethylammonium lactate | as per test |
| 353 | (I-1-a-10) | tetramethylammonium nitrate | as per test |
| 354 | (I-1-a-10) | tetramethylammonium thiosulphate | as per test |
| 355 | (I-1-a-10) | tetramethylammonium thiocyanate | as per test |
| 356 | (I-1-a-10) | tetramethylammonium citrate | as per test |
| 357 | (I-1-a-10) | tetramethylammonium oxalate | as per test |
| 358 | (I-1-a-10) | tetramethylammonium formate | as per test |
| 359 | (I-1-a-10) | tetramethylammonium hydrogenphosphate | as per test |
| 360 | (I-1-a-10) | tetramethylammonium dihydrogenphosphate | as per test |
| 361 | (I-1-a-10) | tetraethylammonium sulphate | as per test |
| 362 | (I-1-a-10) | tetraethylammonium lactate | as per test |
| 363 | (I-1-a-10) | tetraethylammonium nitrate | as per test |
| 364 | (I-1-a-10) | tetraethylammonium thiosulphate | as per test |
| 365 | (I-1-a-10) | tetraethylammonium thiocyanate | as per test |
| 366 | (I-1-a-10) | tetraethylammonium citrate | as per test |
| 367 | (I-1-a-10) | tetraethylammonium oxalate | as per test |
| 368 | (I-1-a-10) | tetraethylammonium formate | as per test |
| 369 | (I-1-a-10) | tetraethylammonium hydrogenphosphate | as per test |
| 370 | (I-1-a-10) | tetraethylammonium dihydrogenphosphate | as per test |
| 371 | (I-1-a-11) | ammonium sulphate | as per test |
| 372 | (I-1-a-11) | ammonium lactate | as per test |
| 373 | (I-1-a-11) | ammonium nitrate | as per test |
| 374 | (I-1-a-11) | ammonium thiosulphate | as per test |
| 375 | (I-1-a-11) | ammonium thiocyanate | as per test |
| 376 | (I-1-a-11) | ammonium citrate | as per test |
| 377 | (I-1-a-11) | ammonium oxalate | as per test |
| 378 | (I-1-a-11) | ammonium formate | as per test |
| 379 | (I-1-a-11) | ammonium hydrogenphosphate | as per test |
| 380 | (I-1-a-11) | ammonium dihydrogenphosphate | as per test |
| 381 | (I-1-a-11) | ammonium carbonate | as per test |
| 382 | (I-1-a-11) | ammonium benzoate | as per test |
| 383 | (I-1-a-11) | ammonium sulphite | as per test |
| 384 | (I-1-a-11) | ammonium benzoate | as per test |
| 385 | (I-1-a-11) | ammonium hydrogenoxalate | as per test |
| 386 | (I-1-a-11) | ammonium hydrogencitrate | as per test |
| 387 | (I-1-a-11) | ammonium acetate | as per test |
| 388 | (I-1-a-11) | tetramethylammonium sulphate | as per test |
| 389 | (I-1-a-11) | tetramethylammonium lactate | as per test |
| 390 | (I-1-a-11) | tetramethylammonium nitrate | as per test |
| 391 | (I-1-a-11) | tetramethylammonium thiosulphate | as per test |
| 392 | (I-1-a-11) | tetramethylammonium thiocyanate | as per test |
| 393 | (I-1-a-11) | tetramethylammonium citrate | as per test |
| 394 | (I-1-a-11) | tetramethylammonium oxalate | as per test |
| 395 | (I-1-a-11) | tetramethylammonium formate | as per test |
| 396 | (I-1-a-11) | tetramethylammonium hydrogenphosphate | as per test |
| 397 | (I-1-a-11) | tetramethylammonium dihydrogenphosphate | as per test |
| 398 | (I-1-a-11) | tetraethylammonium sulphate | as per test |
| 399 | (I-1-a-11) | tetraethylammonium lactate | as per test |
| 400 | (I-1-a-11) | tetraethylammonium nitrate | as per test |
| 401 | (I-1-a-11) | tetraethylammonium thiosulphate | as per test |
| 402 | (I-1-a-11) | tetraethylammonium thiocyanate | as per test |
| 403 | (I-1-a-11) | tetraethylammonium citrate | as per test |
| 404 | (I-1-a-11) | tetraethylammonium oxalate | as per test |
| 405 | (I-1-a-11) | tetraethylammonium formate | as per test |
| 406 | (I-6-a-1) | tetraethylammonium hydrogenphosphate | as per test |
| 407 | (I-1-a-11) | tetraethylammonium dihydrogenphosphate | as per test |
| 408 | (I-1-a-12) | ammonium sulphate | as per test |
| 409 | (I-1-a-12) | ammonium lactate | as per test |
| 410 | (I-1-a-12) | ammonium nitrate | as per test |
| 411 | (I-1-a-12) | ammonium thiosulphate | as per test |
| 412 | (I-1-a-12) | ammonium thiocyanate | as per test |
| 413 | (I-1-a-12) | ammonium citrate | as per test |
| 414 | (I-1-a-12) | ammonium oxalate | as per test |
| 415 | (I-1-a-12) | ammonium formate | as per test |
| 416 | (I-1-a-12) | ammonium hydrogenphosphate | as per test |
| 417 | (I-1-a-12) | ammonium dihydrogenphosphate | as per test |
| 418 | (I-1-a-12) | ammonium carbonate | as per test |
| 419 | (I-1-a-12) | ammonium benzoate | as per test |
| 420 | (I-1-a-12) | ammonium sulphite | as per test |
| 421 | (I-1-a-12) | ammonium benzoate | as per test |
| 422 | (I-1-a-12) | ammonium hydrogenoxalate | as per test |
| 423 | (I-1-a-12) | ammonium hydrogencitrate | as per test |
| 424 | (I-1-a-12) | ammonium acetate | as per test |
| 425 | (I-1-a-12) | tetramethylammonium sulphate | as per test |
| 426 | (I-1-a-12) | tetramethylammonium lactate | as per test |
| 427 | (I-1-a-12) | tetramethylammonium nitrate | as per test |
| 428 | (I-1-a-12) | tetramethylammonium thiosulphate | as per test |
| 429 | (I-1-a-12) | tetramethylammonium thiocyanate | as per test |
| 430 | (I-1-a-12) | tetramethylammonium citrate | as per test |
| 431 | (I-1-a-12) | tetramethylammonium oxalate | as per test |
| 432 | (I-1-a-12) | tetramethylammonium formate | as per test |
| 433 | (I-1-a-12) | tetramethylammonium hydrogenphosphate | as per test |
| 434 | (I-1-a-12) | tetramethylammonium dihydrogenphosphate | as per test |
| 435 | (I-1-a-12) | tetraethylammonium sulphate | as per test |
| 436 | (I-1-a-12) | tetraethylammonium lactate | as per test |
| 437 | (I-1-a-12) | tetraethylammonium nitrate | as per test |
| 438 | (I-1-a-12) | tetraethylammonium thiosulphate | as per test |
| 439 | (I-1-a-12) | tetraethylammonium thiocyanate | as per test |
| 440 | (I-1-a-12) | tetraethylammonium citrate | as per test |
| 441 | (I-1-a-12) | tetraethylammonium oxalate | as per test |
| 442 | (I-1-a-12) | tetraethylammonium formate | as per test |
| 443 | (I-1-a-12) | tetraethylammonium hydrogenphosphate | as per test |
| 444 | (I-1-a-12) | tetraethylammonium dihydrogenphosphate | as per test |
| 445 | (I-1-a-13) | ammonium sulphate | as per test |
| 446 | (I-1-a-13) | ammonium lactate | as per test |
| 447 | (I-1-a-13) | ammonium nitrate | as per test |
| 448 | (I-1-a-13) | ammonium thiosulphate | as per test |
| 449 | (I-1-a-13) | ammonium thiocyanate | as per test |
| 450 | (I-1-a-13) | ammonium citrate | as per test |
| 451 | (I-1-a-13) | ammonium oxalate | as per test |
| 452 | (I-1-a-13) | ammonium formate | as per test |
| 453 | (I-1-a-13) | ammonium hydrogenphosphate | as per test |
| 454 | (I-1-a-13) | ammonium dihydrogenphosphate | as per test |
| 455 | (I-1-a-13) | ammonium carbonate | as per test |
| 456 | (I-1-a-13) | ammonium benzoate | as per test |
| 457 | (I-1-a-13) | ammonium sulphite | as per test |
| 458 | (I-1-a-13) | ammonium benzoate | as per test |
| 459 | (I-1-a-13) | ammonium hydrogenoxalate | as per test |
| 460 | (I-1-a-13) | ammonium hydrogencitrate | as per test |
| 461 | (I-1-a-13) | ammonium acetate | as per test |

| # | Active ingredient | Salt | Penetrant |
|---|---|---|---|
| 462 | (I-1-a-13) | tetramethylammonium sulphate | as per test |
| 463 | (I-1-a-13) | tetramethylammonium lactate | as per test |
| 464 | (I-1-a-13) | tetramethylammonium nitrate | as per test |
| 465 | (I-1-a-13) | tetramethylammonium thiosulphate | as per test |
| 466 | (I-1-a-13) | tetramethylammonium thiocyanate | as per test |
| 467 | (I-1-a-13) | tetramethylammonium citrate | as per test |
| 468 | (I-1-a-13) | tetramethylammonium oxalate | as per test |
| 469 | (I-1-a-13) | tetramethylammonium formate | as per test |
| 470 | (I-1-a-13) | tetramethylammonium hydrogenphosphate | as per test |
| 471 | (I-1-a-13) | tetramethylammonium dihydrogenphosphate | as per test |
| 472 | (I-1-a-13) | tetraethylammonium sulphate | as per test |
| 473 | (I-1-a-13) | tetraethylammonium lactate | as per test |
| 474 | (I-1-a-13) | tetraethylammonium nitrate | as per test |
| 475 | (I-1-a-13) | tetraethylammonium thiosulphate | as per test |
| 476 | (I-1-a-13) | tetraethylammonium thiocyanate | as per test |
| 477 | (I-1-a-13) | tetraethylammonium citrate | as per test |
| 478 | (I-1-a-13) | tetraethylammonium oxalate | as per test |
| 479 | (I-1-a-13) | tetraethylammonium formate | as per test |
| 480 | (I-1-a-13) | tetraethylammonium hydrogenphosphate | as per test |
| 481 | (I-1-a-13) | tetraethylammonium dihydrogenphosphate | as per test |
| 482 | (I-1-a-14) | ammonium sulphate | as per test |
| 483 | (I-1-a-14) | ammonium lactate | as per test |
| 484 | (I-1-a-14) | ammonium nitrate | as per test |
| 485 | (I-1-a-14) | ammonium thiosulphate | as per test |
| 486 | (I-1-a-14) | ammonium thiocyanate | as per test |
| 487 | (I-1-a-14) | ammonium citrate | as per test |
| 488 | (I-1-a-14) | ammonium oxalate | as per test |
| 489 | (I-1-a-14) | ammonium formate | as per test |
| 490 | (I-1-a-14) | ammonium hydrogenphosphate | as per test |
| 491 | (I-1-a-14) | ammonium dihydrogenphosphate | as per test |
| 492 | (I-1-a-14) | ammonium carbonate | as per test |
| 493 | (I-1-a-14) | ammonium benzoate | as per test |
| 494 | (I-1-a-14) | ammonium sulphite | as per test |
| 495 | (I-1-a-14) | ammonium benzoate | as per test |
| 496 | (I-1-a-14) | ammonium hydrogenoxalate | as per test |
| 497 | (I-1-a-14) | ammonium hydrogencitrate | as per test |
| 498 | (I-1-a-14) | ammonium acetate | as per test |
| 499 | (I-1-a-14) | tetramethylammonium sulphate | as per test |
| 500 | (I-1-a-14) | tetramethylammonium lactate | as per test |
| 501 | (I-1-a-14) | tetramethylammonium nitrate | as per test |
| 502 | (I-1-a-14) | tetramethylammonium thiosulphate | as per test |
| 503 | (I-1-a-14) | tetramethylammonium thiocyanate | as per test |
| 504 | (I-1-a-14) | tetramethylammonium citrate | as per test |
| 505 | (I-1-a-14) | tetramethylammonium oxalate | as per test |
| 506 | (I-1-a-14) | tetramethylammonium formate | as per test |
| 507 | (I-1-a-14) | tetramethylammonium hydrogenphosphate | as per test |
| 508 | (I-1-a-14) | tetramethylammonium dihydrogenphosphate | as per test |
| 509 | (I-1-a-14) | tetraethylammonium sulphate | as per test |
| 510 | (I-1-a-14) | tetraethylammonium lactate | as per test |
| 511 | (I-1-a-14) | tetraethylammonium nitrate | as per test |
| 512 | (I-1-a-14) | tetraethylammonium thiosulphate | as per test |
| 513 | (I-1-a-14) | tetraethylammonium thiocyanate | as per test |
| 514 | (I-1-a-14) | tetraethylammonium citrate | as per test |
| 515 | (I-1-a-14) | tetraethylammonium oxalate | as per test |
| 516 | (I-1-a-14) | tetraethylammonium formate | as per test |
| 517 | (I-1-a-14) | tetraethylammonium hydrogenphosphate | as per test |
| 518 | (I-1-a-14) | tetraethylammonium dihydrogenphosphate | as per test |
| 519 | (I-1-a-15) | ammonium sulphate | as per test |
| 520 | (I-1-a-15) | ammonium lactate | as per test |
| 521 | (I-1-a-15) | ammonium nitrate | as per test |
| 522 | (I-1-a-15) | ammonium thiosulphate | as per test |
| 523 | (I-1-a-15) | ammonium thiocyanate | as per test |
| 524 | (I-1-a-15) | ammonium citrate | as per test |
| 525 | (I-1-a-15) | ammonium oxalate | as per test |
| 526 | (I-1-a-15) | ammonium formate | as per test |
| 527 | (I-1-a-15) | ammonium hydrogenphosphate | as per test |
| 528 | (I-1-a-15) | ammonium dihydrogenphosphate | as per test |
| 529 | (I-1-a-15) | ammonium carbonate | as per test |
| 530 | (I-1-a-15) | ammonium benzoate | as per test |
| 531 | (I-1-a-15) | ammonium sulphite | as per test |
| 532 | (I-1-a-15) | ammonium benzoate | as per test |
| 533 | (I-1-a-15) | ammonium hydrogenoxalate | as per test |
| 534 | (I-1-a-15) | ammonium hydrogencitrate | as per test |
| 535 | (I-1-a-15) | ammonium acetate | as per test |
| 536 | (I-1-a-15) | tetramethylammonium sulphate | as per test |
| 537 | (I-1-a-15) | tetramethylammonium lactate | as per test |
| 538 | (I-1-a-15) | tetramethylammonium nitrate | as per test |
| 539 | (I-1-a-15) | tetramethylammonium thiosulphate | as per test |
| 540 | (I-1-a-15) | tetramethylammonium thiocyanate | as per test |
| 541 | (I-1-a-15) | tetramethylammonium citrate | as per test |
| 542 | (I-1-a-15) | tetramethylammonium oxalate | as per test |
| 543 | (I-1-a-15) | tetramethylammonium formate | as per test |
| 544 | (I-1-a-15) | tetramethylammonium hydrogenphosphate | as per test |
| 545 | (I-1-a-15) | tetramethylammonium dihydrogenphosphate | as per test |
| 546 | (I-1-a-15) | tetraethylammonium sulphate | as per test |
| 547 | (I-1-a-15) | tetraethylammonium lactate | as per test |
| 548 | (I-1-a-15) | tetraethylammonium nitrate | as per test |
| 549 | (I-1-a-15) | tetraethylammonium thiosulphate | as per test |
| 550 | (I-1-a-15) | tetraethylammonium thiocyanate | as per test |
| 551 | (I-1-a-15) | tetraethylammonium citrate | as per test |
| 552 | (I-1-a-15) | tetraethylammonium oxalate | as per test |
| 553 | (I-1-a-15) | tetraethylammonium formate | as per test |
| 554 | (I-1-a-15) | tetraethylammonium hydrogenphosphate | as per test |
| 555 | (I-1-a-15) | tetraethylammonium dihydrogenphosphate | as per test |
| 556 | (I-1-a-16) | ammonium sulphate | as per test |
| 557 | (I-1-a-16) | ammonium lactate | as per test |
| 558 | (I-1-a-16) | ammonium nitrate | as per test |
| 559 | (I-1-a-16) | ammonium thiosulphate | as per test |
| 560 | (I-1-a-16) | ammonium thiocyanate | as per test |
| 561 | (I-1-a-16) | ammonium citrate | as per test |
| 562 | (I-1-a-16) | ammonium oxalate | as per test |
| 563 | (I-1-a-16) | ammonium formate | as per test |
| 564 | (I-1-a-16) | ammonium hydrogenphosphate | as per test |
| 565 | (I-1-a-16) | ammonium dihydrogenphosphate | as per test |
| 566 | (I-1-a-16) | ammonium carbonate | as per test |
| 567 | (I-1-a-16) | ammonium benzoate | as per test |
| 568 | (I-1-a-16) | ammonium sulphite | as per test |
| 569 | (I-1-a-16) | ammonium benzoate | as per test |
| 570 | (I-1-a-16) | ammonium hydrogenoxalate | as per test |
| 571 | (I-1-a-16) | ammonium hydrogencitrate | as per test |
| 572 | (I-1-a-16) | ammonium acetate | as per test |
| 573 | (I-1-a-16) | tetramethylammonium sulphate | as per test |
| 574 | (I-1-a-16) | tetramethylammonium lactate | as per test |
| 575 | (I-1-a-16) | tetramethylammonium nitrate | as per test |
| 576 | (I-1-a-16) | tetramethylammonium thiosulphate | as per test |
| 577 | (I-1-a-16) | tetramethylammonium thiocyanate | as per test |
| 578 | (I-1-a-16) | tetramethylammonium citrate | as per test |
| 579 | (I-1-a-16) | tetramethylammonium oxalate | as per test |
| 580 | (I-1-a-16) | tetramethylammonium formate | as per test |
| 581 | (I-1-a-16) | tetramethylammonium hydrogenphosphate | as per test |
| 582 | (I-1-a-16) | tetramethylammonium dihydrogenphosphate | as per test |
| 583 | (I-1-a-16) | tetraethylammonium sulphate | as per test |
| 584 | (I-1-a-16) | tetraethylammonium lactate | as per test |
| 585 | (I-1-a-16) | tetraethylammonium nitrate | as per test |
| 586 | (I-1-a-16) | tetraethylammonium thiosulphate | as per test |
| 587 | (I-1-a-16) | tetraethylammonium thiocyanate | as per test |
| 588 | (I-1-a-16) | tetraethylammonium citrate | as per test |
| 589 | (I-1-a-16) | tetraethylammonium oxalate | as per test |
| 590 | (I-1-a-16) | tetraethylammonium formate | as per test |
| 591 | (I-1-a-16) | tetraethylammonium hydrogenphosphate | as per test |
| 592 | (I-1-a-16) | tetraethylammonium dihydrogenphosphate | as per test |
| 593 | (I-1-a-17) | ammonium sulphate | as per test |
| 594 | (I-1-a-17) | ammonium lactate | as per test |
| 595 | (I-1-a-17) | ammonium nitrate | as per test |
| 596 | (I-1-a-17) | ammonium thiosulphate | as per test |
| 597 | (I-1-a-17) | ammonium thiocyanate | as per test |
| 598 | (I-1-a-17) | ammonium citrate | as per test |
| 599 | (I-1-a-17) | ammonium oxalate | as per test |
| 600 | (I-1-a-17) | ammonium formate | as per test |
| 601 | (I-1-a-17) | ammonium hydrogenphosphate | as per test |
| 602 | (I-1-a-17) | ammonium dihydrogenphosphate | as per test |
| 603 | (I-1-a-17) | ammonium carbonate | as per test |
| 604 | (I-1-a-17) | ammonium benzoate | as per test |
| 605 | (I-1-a-17) | ammonium sulphite | as per test |
| 606 | (I-1-a-17) | ammonium benzoate | as per test |
| 607 | (I-1-a-17) | ammonium hydrogenoxalate | as per test |
| 608 | (I-1-a-17) | ammonium hydrogencitrate | as per test |
| 609 | (I-1-a-17) | ammonium acetate | as per test |
| 610 | (I-1-a-17) | tetramethylammonium sulphate | as per test |
| 611 | (I-1-a-17) | tetramethylammonium lactate | as per test |

-continued

| # | Active ingredient | Salt | Penetrant |
|---|---|---|---|
| 612 | (I-1-a-17) | tetramethylammonium nitrate | as per test |
| 613 | (I-1-a-17) | tetramethylammonium thiosulphate | as per test |
| 614 | (I-1-a-17) | tetramethylammonium thiocyanate | as per test |
| 615 | (I-1-a-17) | tetramethylammonium citrate | as per test |
| 616 | (I-1-a-17) | tetramethylammonium oxalate | as per test |
| 617 | (I-1-a-17) | tetramethylammonium formate | as per test |
| 618 | (I-1-a-17) | tetramethylammonium hydrogenphosphate | as per test |
| 619 | (I-1-a-17) | tetramethylammonium dihydrogenphosphate | as per test |
| 620 | (I-1-a-17) | tetraethylammonium sulphate | as per test |
| 621 | (I-1-a-17) | tetraethylammonium lactate | as per test |
| 622 | (I-1-a-17) | tetraethylammonium nitrate | as per test |
| 623 | (I-1-a-17) | tetraethylammonium thiosulphate | as per test |
| 624 | (I-1-a-17) | tetraethylammonium thiocyanate | as per test |
| 625 | (I-1-a-17) | tetraethylammonium citrate | as per test |
| 626 | (I-1-a-17) | tetraethylammonium oxalate | as per test |
| 627 | (I-1-a-17) | tetraethylammonium formate | as per test |
| 628 | (I-1-a-17) | tetraethylammonium hydrogenphosphate | as per test |
| 629 | (I-1-a-17) | tetraethylammonium dihydrogenphosphate | as per test |
| 630 | (I-1-a-18) | ammonium sulphate | as per test |
| 631 | (I-1-a-18) | ammonium lactate | as per test |
| 632 | (I-1-a-18) | ammonium nitrate | as per test |
| 633 | (I-1-a-18) | ammonium thiosulphate | as per test |
| 634 | (I-1-a-18) | ammonium thiocyanate | as per test |
| 635 | (I-1-a-18) | ammonium citrate | as per test |
| 636 | (I-1-a-18) | ammonium oxalate | as per test |
| 637 | (I-1-a-18) | ammonium formate | as per test |
| 638 | (I-1-a-18) | ammonium hydrogenphosphate | as per test |
| 639 | (I-1-a-18) | ammonium dihydrogenphosphate | as per test |
| 640 | (I-1-a-18) | ammonium carbonate | as per test |
| 641 | (I-1-a-18) | ammonium benzoate | as per test |
| 642 | (I-1-a-18) | ammonium sulphite | as per test |
| 643 | (I-1-a-18) | ammonium benzoate | as per test |
| 644 | (I-1-a-18) | ammonium hydrogenoxalate | as per test |
| 645 | (I-1-a-18) | ammonium hydrogencitrate | as per test |
| 646 | (I-1-a-18) | ammonium acetate | as per test |
| 647 | (I-1-a-18) | tetramethylammonium sulphate | as per test |
| 648 | (I-1-a-18) | tetramethylammonium lactate | as per test |
| 649 | (I-1-a-18) | tetramethylammonium nitrate | as per test |
| 650 | (I-1-a-18) | tetramethylammonium thiosulphate | as per test |
| 651 | (I-1-a-18) | tetramethylammonium thiocyanate | as per test |
| 652 | (I-1-a-18) | tetramethylammonium citrate | as per test |
| 653 | (I-1-a-18) | tetramethylammonium oxalate | as per test |
| 654 | (I-1-a-18) | tetramethylammonium formate | as per test |
| 655 | (I-1-a-18) | tetramethylammonium hydrogenphosphate | as per test |
| 656 | (I-1-a-18) | tetramethylammonium dihydrogenphosphate | as per test |
| 657 | (I-1-a-18) | tetraethylammonium sulphate | as per test |
| 658 | (I-1-a-18) | tetraethylammonium lactate | as per test |
| 659 | (I-1-a-18) | tetraethylammonium nitrate | as per test |
| 660 | (I-1-a-18) | tetraethylammonium thiosulphate | as per test |
| 661 | (I-1-a-18) | tetraethylammonium thiocyanate | as per test |
| 662 | (I-1-a-18) | tetraethylammonium citrate | as per test |
| 663 | (I-1-a-18) | tetraethylammonium oxalate | as per test |
| 664 | (I-1-a-18) | tetraethylammonium formate | as per test |
| 665 | (I-1-a-18) | tetraethylammonium hydrogenphosphate | as per test |
| 666 | (I-1-a-18) | tetraethylammonium dihydrogenphosphate | as per test |
| 667 | (I-1-c-1) | ammonium sulphate | as per test |
| 668 | (I-1-c-1) | ammonium lactate | as per test |
| 669 | (I-1-c-1) | ammonium nitrate | as per test |
| 670 | (I-1-c-1) | ammonium thiosulphate | as per test |
| 671 | (I-1-c-1) | ammonium thiocyanate | as per test |
| 672 | (I-1-c-1) | ammonium citrate | as per test |
| 673 | (I-1-c-1) | ammonium oxalate | as per test |
| 674 | (I-1-c-1) | ammonium formate | as per test |
| 675 | (I-1-c-1) | ammonium hydrogenphosphate | as per test |
| 676 | (I-1-c-1) | ammonium dihydrogenphosphate | as per test |
| 677 | (I-1-c-1) | ammonium carbonate | as per test |
| 678 | (I-1-c-1) | ammonium benzoate | as per test |
| 679 | (I-1-c-1) | ammonium sulphite | as per test |
| 680 | (I-1-c-1) | ammonium benzoate | as per test |
| 681 | (I-1-c-1) | ammonium hydrogenoxalate | as per test |
| 682 | (I-1-c-1) | ammonium hydrogencitrate | as per test |
| 683 | (I-1-c-1) | ammonium acetate | as per test |
| 684 | (I-1-c-1) | tetramethylammonium sulphate | as per test |
| 685 | (I-1-c-1) | tetramethylammonium lactate | as per test |
| 686 | (I-1-c-1) | tetramethylammonium nitrate | as per test |
| 687 | (I-1-c-1) | tetramethylammonium thiosulphate | as per test |
| 688 | (I-1-c-1) | tetramethylammonium thiocyanate | as per test |
| 689 | (I-1-c-1) | tetramethylammonium citrate | as per test |
| 690 | (I-1-c-1) | tetramethylammonium oxalate | as per test |
| 691 | (I-1-c-1) | tetramethylammonium formate | as per test |
| 692 | (I-1-c-1) | tetramethylammonium hydrogenphosphate | as per test |
| 693 | (I-1-c-1) | tetramethylammonium dihydrogenphosphate | as per test |
| 694 | (I-1-c-1) | tetraethylammonium sulphate | as per test |
| 695 | (I-1-c-1) | tetraethylammonium lactate | as per test |
| 696 | (I-1-c-1) | tetraethylammonium nitrate | as per test |
| 697 | (I-1-c-1) | tetraethylammonium thiosulphate | as per test |
| 698 | (I-1-c-1) | tetraethylammonium thiocyanate | as per test |
| 699 | (I-1-c-1) | tetraethylammonium citrate | as per test |
| 700 | (I-1-c-1) | tetraethylammonium oxalate | as per test |
| 701 | (I-1-c-1) | tetraethylammonium formate | as per test |
| 702 | (I-1-c-1) | tetraethylammonium hydrogenphosphate | as per test |
| 703 | (I-1-c-1) | tetraethylammonium dihydrogenphosphate | as per test |
| 704 | (I-1-c-2) | ammonium sulphate | as per test |
| 705 | (I-1-c-2) | ammonium lactate | as per test |
| 706 | (I-1-c-2) | ammonium nitrate | as per test |
| 707 | (I-1-c-2) | ammonium thiosulphate | as per test |
| 708 | (I-1-c-2) | ammonium thiocyanate | as per test |
| 709 | (I-1-c-2) | ammonium citrate | as per test |
| 710 | (I-1-c-2) | ammonium oxalate | as per test |
| 711 | (I-1-c-2) | ammonium formate | as per test |
| 712 | (I-1-c-2) | ammonium hydrogenphosphate | as per test |
| 713 | (I-1-c-2) | ammonium dihydrogenphosphate | as per test |
| 714 | (I-1-c-2) | ammonium carbonate | as per test |
| 715 | (I-1-c-2) | ammonium benzoate | as per test |
| 716 | (I-1-c-2) | ammonium sulphite | as per test |
| 717 | (I-1-c-2) | ammonium benzoate | as per test |
| 718 | (I-1-c-2) | ammonium hydrogenoxalate | as per test |
| 719 | (I-1-c-2) | ammonium hydrogencitrate | as per test |
| 720 | (I-1-c-2) | ammonium acetate | as per test |
| 721 | (I-1-c-2) | tetramethylammonium sulphate | as per test |
| 722 | (I-1-c-2) | tetramethylammonium lactate | as per test |
| 723 | (I-1-c-2) | tetramethylammonium nitrate | as per test |
| 724 | (I-1-c-2) | tetramethylammonium thiosulphate | as per test |
| 725 | (I-1-c-2) | tetramethylammonium thiocyanate | as per test |
| 726 | (I-1-c-2) | tetramethylammonium citrate | as per test |
| 727 | (I-1-c-2) | tetramethylammonium oxalate | as per test |
| 728 | (I-1-c-2) | tetramethylammonium formate | as per test |
| 729 | (I-1-c-2) | tetramethylammonium hydrogenphosphate | as per test |
| 730 | (I-1-c-2) | tetramethylammonium dihydrogenphosphate | as per test |
| 731 | (I-1-c-2) | tetraethylammonium sulphate | as per test |
| 732 | (I-1-c-2) | tetraethylammonium lactate | as per test |
| 733 | (I-1-c-2) | tetraethylammonium nitrate | as per test |
| 734 | (I-1-c-2) | tetraethylammonium thiosulphate | as per test |
| 735 | (I-1-c-2) | tetraethylammonium thiocyanate | as per test |
| 736 | (I-1-c-2) | tetraethylammonium citrate | as per test |
| 737 | (I-1-c-2) | tetraethylammonium oxalate | as per test |
| 738 | (I-1-c-2) | tetraethylammonium formate | as per test |
| 739 | (I-1-c-2) | tetraethylammonium hydrogenphosphate | as per test |
| 740 | (I-1-c-2) | tetraethylammonium dihydrogenphosphate | as per test |
| 741 | (I-2-a-1) | ammonium sulphate | as per test |
| 742 | (I-2-a-1) | ammonium lactate | as per test |
| 743 | (I-2-a-1) | ammonium nitrate | as per test |
| 744 | (I-2-a-1) | ammonium thiosulphate | as per test |
| 745 | (I-2-a-1) | ammonium thiocyanate | as per test |
| 746 | (I-2-a-1) | ammonium citrate | as per test |
| 747 | (I-2-a-1) | ammonium oxalate | as per test |
| 748 | (I-2-a-1) | ammonium formate | as per test |
| 749 | (I-2-a-1) | ammonium hydrogenphosphate | as per test |
| 750 | (I-2-a-1) | ammonium dihydrogenphosphate | as per test |
| 751 | (I-2-a-1) | ammonium carbonate | as per test |
| 752 | (I-2-a-1) | ammonium benzoate | as per test |
| 753 | (I-2-a-1) | ammonium sulphite | as per test |
| 754 | (I-2-a-1) | ammonium benzoate | as per test |
| 755 | (I-2-a-1) | ammonium hydrogenoxalate | as per test |
| 756 | (I-2-a-1) | ammonium hydrogencitrate | as per test |
| 757 | (I-2-a-1) | ammonium acetate | as per test |
| 758 | (I-2-a-1) | tetramethylammonium sulphate | as per test |
| 759 | (I-2-a-1) | tetramethylammonium lactate | as per test |
| 760 | (I-2-a-1) | tetramethylammonium nitrate | as per test |
| 761 | (I-2-a-1) | tetramethylammonium thiosulphate | as per test |

| # | Active ingredient | Salt | Penetrant |
|---|---|---|---|
| 762 | (I-2-a-1) | tetramethylammonium thiocyanate | as per test |
| 763 | (I-2-a-1) | tetramethylammonium citrate | as per test |
| 764 | (I-2-a-1) | tetramethylammonium oxalate | as per test |
| 765 | (I-2-a-1) | tetramethylammonium formate | as per test |
| 766 | (I-2-a-1) | tetramethylammonium hydrogenphosphate | as per test |
| 767 | (I-2-a-1) | tetramethylammonium dihydrogenphosphate | as per test |
| 768 | (I-2-a-1) | tetraethylammonium sulphate | as per test |
| 769 | (I-2-a-1) | tetraethylammonium lactate | as per test |
| 770 | (I-2-a-1) | tetraethylammonium nitrate | as per test |
| 771 | (I-2-a-1) | tetraethylammonium thiosulphate | as per test |
| 772 | (I-2-a-1) | tetraethylammonium thiocyanate | as per test |
| 773 | (I-2-a-1) | tetraethylammonium citrate | as per test |
| 774 | (I-2-a-1) | tetraethylammonium oxalate | as per test |
| 775 | (I-2-a-1) | tetraethylammonium formate | as per test |
| 776 | (I-2-a-1) | tetraethylammonium hydrogenphosphate | as per test |
| 777 | (I-2-a-1) | tetraethylammonium dihydrogenphosphate | as per test |
| 778 | (I-2-a-2) | ammonium sulphate | as per test |
| 779 | (I-2-a-2) | ammonium lactate | as per test |
| 780 | (I-2-a-2) | ammonium nitrate | as per test |
| 781 | (I-2-a-2) | ammonium thiosulphate | as per test |
| 782 | (I-2-a-2) | ammonium thiocyanate | as per test |
| 783 | (I-2-a-2) | ammonium citrate | as per test |
| 784 | (I-2-a-2) | ammonium oxalate | as per test |
| 785 | (I-2-a-2) | ammonium formate | as per test |
| 786 | (I-2-a-2) | ammonium hydrogenphosphate | as per test |
| 787 | (I-2-a-2) | ammonium dihydrogenphosphate | as per test |
| 788 | (I-2-a-2) | ammonium carbonate | as per test |
| 789 | (I-2-a-2) | ammonium benzoate | as per test |
| 790 | (I-2-a-2) | ammonium sulphite | as per test |
| 791 | (I-2-a-2) | ammonium benzoate | as per test |
| 792 | (I-2-a-2) | ammonium hydrogenoxalate | as per test |
| 793 | (I-2-a-2) | ammonium hydrogencitrate | as per test |
| 794 | (I-2-a-2) | ammonium acetate | as per test |
| 795 | (I-2-a-2) | tetramethylammonium sulphate | as per test |
| 796 | (I-2-a-2) | tetramethylammonium lactate | as per test |
| 797 | (I-2-a-2) | tetramethylammonium nitrate | as per test |
| 798 | (I-2-a-2) | tetramethylammonium thiosulphate | as per test |
| 799 | (I-2-a-2) | tetramethylammonium thiocyanate | as per test |
| 800 | (I-2-a-2) | tetramethylammonium citrate | as per test |
| 801 | (I-2-a-2) | tetramethylammonium oxalate | as per test |
| 802 | (I-2-a-2) | tetramethylammonium formate | as per test |
| 803 | (I-2-a-2) | tetramethylammonium hydrogenphosphate | as per test |
| 804 | (I-2-a-2) | tetramethylammonium dihydrogenphosphate | as per test |
| 805 | (I-2-a-2) | tetraethylammonium sulphate | as per test |
| 806 | (I-2-a-2) | tetraethylammonium lactate | as per test |
| 807 | (I-2-a-2) | tetraethylammonium nitrate | as per test |
| 808 | (I-2-a-2) | tetraethylammonium thiosulphate | as per test |
| 809 | (I-2-a-2) | tetraethylammonium thiocyanate | as per test |
| 810 | (I-2-a-2) | tetraethylammonium citrate | as per test |
| 811 | (I-2-a-2) | tetraethylammonium oxalate | as per test |
| 812 | (I-2-a-2) | tetraethylammonium formate | as per test |
| 813 | (I-2-a-2) | tetraethylammonium hydrogenphosphate | as per test |
| 814 | (I-2-a-2) | tetraethylammonium dihydrogenphosphate | as per test |
| 815 | (I-2-a-3) | ammonium sulphate | as per test |
| 816 | (I-2-a-3) | ammonium lactate | as per test |
| 817 | (I-2-a-3) | ammonium nitrate | as per test |
| 818 | (I-2-a-3) | ammonium thiosulphate | as per test |
| 819 | (I-2-a-3) | ammonium thiocyanate | as per test |
| 820 | (I-2-a-3) | ammonium citrate | as per test |
| 821 | (I-2-a-3) | ammonium oxalate | as per test |
| 822 | (I-2-a-3) | ammonium formate | as per test |
| 823 | (I-2-a-3) | ammonium hydrogenphosphate | as per test |
| 824 | (I-2-a-3) | ammonium dihydrogenphosphate | as per test |
| 825 | (I-2-a-3) | ammonium carbonate | as per test |
| 826 | (I-2-a-3) | ammonium benzoate | as per test |
| 827 | (I-2-a-3) | ammonium sulphite | as per test |
| 828 | (I-2-a-3) | ammonium benzoate | as per test |
| 829 | (I-2-a-3) | ammonium hydrogenoxalate | as per test |
| 830 | (I-2-a-3) | ammonium hydrogencitrate | as per test |
| 831 | (I-2-a-3) | ammonium acetate | as per test |
| 832 | (I-2-a-3) | tetramethylammonium sulphate | as per test |
| 833 | (I-2-a-3) | tetramethylammonium lactate | as per test |
| 834 | (I-2-a-3) | tetramethylammonium nitrate | as per test |
| 835 | (I-2-a-3) | tetramethylammonium thiosulphate | as per test |
| 836 | (I-2-a-3) | tetramethylammonium thiocyanate | as per test |
| 837 | (I-2-a-3) | tetramethylammonium citrate | as per test |
| 838 | (I-2-a-3) | tetramethylammonium oxalate | as per test |
| 839 | (I-2-a-3) | tetramethylammonium formate | as per test |
| 840 | (I-2-a-3) | tetramethylammonium hydrogenphosphate | as per test |
| 841 | (I-2-a-3) | tetramethylammonium dihydrogenphosphate | as per test |
| 842 | (I-2-a-3) | tetraethylammonium sulphate | as per test |
| 843 | (I-2-a-3) | tetraethylammonium lactate | as per test |
| 844 | (I-2-a-3) | tetraethylammonium nitrate | as per test |
| 845 | (I-2-a-3) | tetraethylammonium thiosulphate | as per test |
| 846 | (I-2-a-3) | tetraethylammonium thiocyanate | as per test |
| 847 | (I-2-a-3) | tetraethylammonium citrate | as per test |
| 848 | (I-2-a-3) | tetraethylammonium oxalate | as per test |
| 849 | (I-2-a-3) | tetraethylammonium formate | as per test |
| 850 | (I-2-a-3) | tetraethylammonium hydrogenphosphate | as per test |
| 851 | (I-2-a-3) | tetraethylammonium dihydrogenphosphate | as per test |
| 852 | (I-2-a-4) | ammonium sulphate | as per test |
| 853 | (I-2-a-4) | ammonium lactate | as per test |
| 854 | (I-2-a-4) | ammonium nitrate | as per test |
| 855 | (I-2-a-4) | ammonium thiosulphate | as per test |
| 856 | (I-2-a-4) | ammonium thiocyanate | as per test |
| 857 | (I-2-a-4) | ammonium citrate | as per test |
| 858 | (I-2-a-4) | ammonium oxalate | as per test |
| 859 | (I-2-a-4) | ammonium formate | as per test |
| 860 | (I-2-a-4) | ammonium hydrogenphosphate | as per test |
| 861 | (I-2-a-4) | ammonium dihydrogenphosphate | as per test |
| 862 | (I-2-a-4) | ammonium carbonate | as per test |
| 863 | (I-2-a-4) | ammonium benzoate | as per test |
| 864 | (I-2-a-4) | ammonium sulphite | as per test |
| 865 | (I-2-a-4) | ammonium benzoate | as per test |
| 866 | (I-2-a-4) | ammonium hydrogenoxalate | as per test |
| 867 | (I-2-a-4) | ammonium hydrogencitrate | as per test |
| 868 | (I-2-a-4) | ammonium acetate | as per test |
| 869 | (I-2-a-4) | tetramethylammonium sulphate | as per test |
| 870 | (I-2-a-4) | tetramethylammonium lactate | as per test |
| 871 | (I-2-a-4) | tetramethylammonium nitrate | as per test |
| 872 | (I-2-a-4) | tetramethylammonium thiosulphate | as per test |
| 873 | (I-2-a-4) | tetramethylammonium thiocyanate | as per test |
| 874 | (I-2-a-4) | tetramethylammonium citrate | as per test |
| 875 | (I-2-a-4) | tetramethylammonium oxalate | as per test |
| 876 | (I-2-a-4) | tetramethylammonium formate | as per test |
| 877 | (I-2-a-4) | tetramethylammonium hydrogenphosphate | as per test |
| 878 | (I-2-a-4) | tetramethylammonium dihydrogenphosphate | as per test |
| 879 | (I-2-a-4) | tetraethylammonium sulphate | as per test |
| 880 | (I-2-a-4) | tetraethylammonium lactate | as per test |
| 881 | (I-2-a-4) | tetraethylammonium nitrate | as per test |
| 882 | (I-2-a-4) | tetraethylammonium thiosulphate | as per test |
| 883 | (I-2-a-4) | tetraethylammonium thiocyanate | as per test |
| 884 | (I-2-a-4) | tetraethylammonium citrate | as per test |
| 885 | (I-2-a-4) | tetraethylammonium oxalate | as per test |
| 886 | (I-2-a-4) | tetraethylammonium formate | as per test |
| 887 | (I-2-a-4) | tetraethylammonium hydrogenphosphate | as per test |
| 888 | (I-2-a-4) | tetraethylammonium dihydrogenphosphate | as per test |
| 889 | (I-2-b-1) | ammonium sulphate | as per test |
| 890 | (I-2-b-1) | ammonium lactate | as per test |
| 891 | (I-2-b-1) | ammonium nitrate | as per test |
| 892 | (I-2-b-1) | ammonium thiosulphate | as per test |
| 893 | (I-2-b-1) | ammonium thiocyanate | as per test |
| 894 | (I-2-b-1) | ammonium citrate | as per test |
| 895 | (I-2-b-1) | ammonium oxalate | as per test |
| 896 | (I-2-b-1) | ammonium formate | as per test |
| 897 | (I-2-b-1) | ammonium hydrogenphosphate | as per test |
| 898 | (I-2-b-1) | ammonium dihydrogenphosphate | as per test |
| 899 | (I-2-b-1) | ammonium carbonate | as per test |
| 900 | (I-2-b-1) | ammonium benzoate | as per test |
| 901 | (I-2-b-1) | ammonium sulphite | as per test |
| 902 | (I-2-b-1) | ammonium benzoate | as per test |
| 903 | (I-2-b-1) | ammonium hydrogenoxalate | as per test |
| 904 | (I-2-b-1) | ammonium hydrogencitrate | as per test |
| 905 | (I-2-b-1) | ammonium acetate | as per test |
| 906 | (I-2-b-1) | tetramethylammonium sulphate | as per test |
| 907 | (I-2-b-1) | tetramethylammonium lactate | as per test |
| 908 | (I-2-b-1) | tetramethylammonium nitrate | as per test |
| 909 | (I-2-b-1) | tetramethylammonium thiosulphate | as per test |
| 910 | (I-2-b-1) | tetramethylammonium thiocyanate | as per test |
| 911 | (I-2-b-1) | tetramethylammonium citrate | as per test |

-continued

| # | Active ingredient | Salt | Penetrant |
|---|---|---|---|
| 912 | (I-2-b-1) | tetramethylammonium oxalate | as per test |
| 913 | (I-2-b-1) | tetramethylammonium formate | as per test |
| 914 | (I-2-b-1) | tetramethylammonium hydrogenphosphate | as per test |
| 915 | (I-2-b-1) | tetramethylammonium dihydrogenphosphate | as per test |
| 916 | (I-2-b-1) | tetraethylammonium sulphate | as per test |
| 917 | (I-2-b-1) | tetraethylammonium lactate | as per test |
| 918 | (I-2-b-1) | tetraethylammonium nitrate | as per test |
| 919 | (I-2-b-1) | tetraethylammonium thiosulphate | as per test |
| 920 | (I-2-b-1) | tetraethylammonium thiocyanate | as per test |
| 921 | (I-2-b-1) | tetraethylammonium citrate | as per test |
| 922 | (I-2-b-1) | tetraethylammonium oxalate | as per test |
| 923 | (I-2-b-1) | tetraethylammonium formate | as per test |
| 924 | (I-2-b-1) | tetraethylammonium hydrogenphosphate | as per test |
| 925 | (I-2-b-1) | tetraethylammonium dihydrogenphosphate | as per test |
| 926 | (I-2-b-2) | ammonium sulphate | as per test |
| 927 | (I-2-b-2) | ammonium lactate | as per test |
| 928 | (I-2-b-2) | ammonium nitrate | as per test |
| 929 | (I-2-b-2) | ammonium thiosulphate | as per test |
| 930 | (I-2-b-2) | ammonium thiocyanate | as per test |
| 931 | (I-2-b-2) | ammonium citrate | as per test |
| 932 | (I-2-b-2) | ammonium oxalate | as per test |
| 933 | (I-2-b-2) | ammonium formate | as per test |
| 934 | (I-2-b-2) | ammonium hydrogenphosphate | as per test |
| 935 | (I-2-b-2) | ammonium dihydrogenphosphate | as per test |
| 936 | (I-2-b-2) | ammonium carbonate | as per test |
| 937 | (I-2-b-2) | ammonium benzoate | as per test |
| 938 | (I-2-b-2) | ammonium sulphite | as per test |
| 939 | (I-2-b-2) | ammonium benzoate | as per test |
| 940 | (I-2-b-2) | ammonium hydrogenoxalate | as per test |
| 941 | (I-2-b-2) | ammonium hydrogencitrate | as per test |
| 942 | (I-2-b-2) | ammonium acetate | as per test |
| 943 | (I-2-b-2) | tetramethylammonium sulphate | as per test |
| 944 | (I-2-b-2) | tetramethylammonium lactate | as per test |
| 945 | (I-2-b-2) | tetramethylammonium nitrate | as per test |
| 946 | (I-2-b-2) | tetramethylammonium thiosulphate | as per test |
| 947 | (I-2-b-2) | tetramethylammonium thiocyanate | as per test |
| 948 | (I-2-b-2) | tetramethylammonium citrate | as per test |
| 949 | (I-2-b-2) | tetramethylammonium oxalate | as per test |
| 950 | (I-2-b-2) | tetramethylammonium formate | as per test |
| 951 | (I-2-b-2) | tetramethylammonium hydrogenphosphate | as per test |
| 952 | (I-2-b-2) | tetramethylammonium dihydrogenphosphate | as per test |
| 953 | (I-2-b-2) | tetraethylammonium sulphate | as per test |
| 954 | (I-2-b-2) | tetraethylammonium lactate | as per test |
| 955 | (I-2-b-2) | tetraethylammonium nitrate | as per test |
| 956 | (I-2-b-2) | tetraethylammonium thiosulphate | as per test |
| 957 | (I-2-b-2) | tetraethylammonium thiocyanate | as per test |
| 958 | (I-2-b-2) | tetraethylammonium citrate | as per test |
| 959 | (I-2-b-2) | tetraethylammonium oxalate | as per test |
| 960 | (I-2-b-2) | tetraethylammonium formate | as per test |
| 961 | (I-2-b-2) | tetraethylammonium hydrogenphosphate | as per test |
| 962 | (I-2-b-2) | tetraethylammonium dihydrogenphosphate | as per test |
| 963 | (I-4-a-1) | ammonium sulphate | as per test |
| 964 | (I-4-a-1) | ammonium lactate | as per test |
| 965 | (I-4-a-1) | ammonium nitrate | as per test |
| 966 | (I-4-a-1) | ammonium thiosulphate | as per test |
| 967 | (I-4-a-1) | ammonium thiocyanate | as per test |
| 968 | (I-4-a-1) | ammonium citrate | as per test |
| 969 | (I-4-a-1) | ammonium oxalate | as per test |
| 970 | (I-4-a-1) | ammonium formate | as per test |
| 971 | (I-4-a-1) | ammonium hydrogenphosphate | as per test |
| 972 | (I-4-a-1) | ammonium dihydrogenphosphate | as per test |
| 973 | (I-4-a-1) | ammonium carbonate | as per test |
| 974 | (I-4-a-1) | ammonium benzoate | as per test |
| 975 | (I-4-a-1) | ammonium sulphite | as per test |
| 976 | (I-4-a-1) | ammonium benzoate | as per test |
| 977 | (I-4-a-1) | ammonium hydrogenoxalate | as per test |
| 978 | (I-4-a-1) | ammonium hydrogencitrate | as per test |
| 979 | (I-4-a-1) | ammonium acetate | as per test |
| 980 | (I-4-a-1) | tetramethylammonium sulphate | as per test |
| 981 | (I-4-a-1) | tetramethylammonium lactate | as per test |
| 982 | (I-4-a-1) | tetramethylammonium nitrate | as per test |
| 983 | (I-4-a-1) | tetramethylammonium thiosulphate | as per test |
| 984 | (I-4-a-1) | tetramethylammonium thiocyanate | as per test |
| 985 | (I-4-a-1) | tetramethylammonium citrate | as per test |
| 986 | (I-4-a-1) | tetramethylammonium oxalate | as per test |
| 987 | (I-4-a-1) | tetramethylammonium formate | as per test |
| 988 | (I-4-a-1) | tetramethylammonium hydrogenphosphate | as per test |
| 989 | (I-4-a-1) | tetramethylammonium dihydrogenphosphate | as per test |
| 990 | (I-4-a-1) | tetraethylammonium sulphate | as per test |
| 991 | (I-4-a-1) | tetraethylammonium lactate | as per test |
| 992 | (I-4-a-1) | tetraethylammonium nitrate | as per test |
| 993 | (I-4-a-1) | tetraethylammonium thiosulphate | as per test |
| 994 | (I-4-a-1) | tetraethylammonium thiocyanate | as per test |
| 995 | (I-4-a-1) | tetraethylammonium citrate | as per test |
| 996 | (I-4-a-1) | tetraethylammonium oxalate | as per test |
| 997 | (I-4-a-1) | tetraethylammonium formate | as per test |
| 998 | (I-4-a-1) | tetraethylammonium hydrogenphosphate | as per test |
| 999 | (I-4-a-1) | tetraethylammonium dihydrogenphosphate | as per test |
| 1000 | (I-4-a-2) | ammonium sulphate | as per test |
| 1001 | (I-4-a-2) | ammonium lactate | as per test |
| 1002 | (I-4-a-2) | ammonium nitrate | as per test |
| 1003 | (I-4-a-2) | ammonium thiosulphate | as per test |
| 1004 | (I-4-a-2) | ammonium thiocyanate | as per test |
| 1005 | (I-4-a-2) | ammonium citrate | as per test |
| 1006 | (I-4-a-2) | ammonium oxalate | as per test |
| 1007 | (I-4-a-2) | ammonium formate | as per test |
| 1008 | (I-4-a-2) | ammonium hydrogenphosphate | as per test |
| 1009 | (I-4-a-2) | ammonium dihydrogenphosphate | as per test |
| 1010 | (I-4-a-2) | ammonium carbonate | as per test |
| 1011 | (I-4-a-2) | ammonium benzoate | as per test |
| 1012 | (I-4-a-2) | ammonium sulphite | as per test |
| 1013 | (I-4-a-2) | ammonium benzoate | as per test |
| 1014 | (I-4-a-2) | ammonium hydrogenoxalate | as per test |
| 1015 | (I-4-a-2) | ammonium hydrogencitrate | as per test |
| 1016 | (I-4-a-2) | ammonium acetate | as per test |
| 1017 | (I-4-a-2) | tetramethylammonium sulphate | as per test |
| 1018 | (I-4-a-2) | tetramethylammonium lactate | as per test |
| 1019 | (I-4-a-2) | tetramethylammonium nitrate | as per test |
| 1020 | (I-4-a-2) | tetramethylammonium thiosulphate | as per test |
| 1021 | (I-4-a-2) | tetramethylammonium thiocyanate | as per test |
| 1022 | (I-4-a-2) | tetramethylammonium citrate | as per test |
| 1023 | (I-4-a-2) | tetramethylammonium oxalate | as per test |
| 1024 | (I-4-a-2) | tetramethylammonium formate | as per test |
| 1025 | (I-4-a-2) | tetramethylammonium hydrogenphosphate | as per test |
| 1026 | (I-4-a-2) | tetramethylammonium dihydrogenphosphate | as per test |
| 1027 | (I-4-a-2) | tetraethylammonium sulphate | as per test |
| 1028 | (I-4-a-2) | tetraethylammonium lactate | as per test |
| 1029 | (I-4-a-2) | tetraethylammonium nitrate | as per test |
| 1030 | (I-4-a-2) | tetraethylammonium thiosulphate | as per test |
| 1031 | (I-4-a-2) | tetraethylammonium thiocyanate | as per test |
| 1032 | (I-4-a-2) | tetraethylammonium citrate | as per test |
| 1033 | (I-4-a-2) | tetraethylammonium oxalate | as per test |
| 1034 | (I-4-a-2) | tetraethylammonium formate | as per test |
| 1035 | (I-4-a-2) | tetraethylammonium hydrogenphosphate | as per test |
| 1036 | (I-4-a-2) | tetraethylammonium dihydrogenphosphate | as per test |
| 1037 | (I-4-a-3) | ammonium sulphate | as per test |
| 1038 | (I-4-a-3) | ammonium lactate | as per test |
| 1039 | (I-4-a-3) | ammonium nitrate | as per test |
| 1040 | (I-4-a-3) | ammonium thiosulphate | as per test |
| 1041 | (I-4-a-3) | ammonium thiocyanate | as per test |
| 1042 | (I-4-a-3) | ammonium citrate | as per test |
| 1043 | (I-4-a-3) | ammonium oxalate | as per test |
| 1044 | (I-4-a-3) | ammonium formate | as per test |
| 1045 | (I-4-a-3) | ammonium hydrogenphosphate | as per test |
| 1046 | (I-4-a-3) | ammonium dihydrogenphosphate | as per test |
| 1047 | (I-4-a-3) | ammonium carbonate | as per test |
| 1048 | (I-4-a-3) | ammonium benzoate | as per test |
| 1049 | (I-4-a-3) | ammonium sulphite | as per test |
| 1050 | (I-4-a-3) | ammonium benzoate | as per test |
| 1051 | (I-4-a-3) | ammonium hydrogenoxalate | as per test |
| 1052 | (I-4-a-3) | ammonium hydrogencitrate | as per test |
| 1053 | (I-4-a-3) | ammonium acetate | as per test |
| 1054 | (I-4-a-3) | tetramethylammonium sulphate | as per test |
| 1055 | (I-4-a-3) | tetramethylammonium lactate | as per test |
| 1056 | (I-4-a-3) | tetramethylammonium nitrate | as per test |
| 1057 | (I-4-a-3) | tetramethylammonium thiosulphate | as per test |
| 1058 | (I-4-a-3) | tetramethylammonium thiocyanate | as per test |
| 1059 | (I-4-a-3) | tetramethylammonium citrate | as per test |
| 1060 | (I-4-a-3) | tetramethylammonium oxalate | as per test |
| 1061 | (I-4-a-3) | tetramethylammonium formate | as per test |

-continued

| # | Active ingredient | Salt | Penetrant |
|---|---|---|---|
| 1062 | (I-4-a-3) | tetramethylammonium hydrogenphosphate | as per test |
| 1063 | (I-4-a-3) | tetramethylammonium dihydrogenphosphate | as per test |
| 1064 | (I-4-a-3) | tetraethylammonium sulphate | as per test |
| 1065 | (I-4-a-3) | tetraethylammonium lactate | as per test |
| 1066 | (I-4-a-3) | tetraethylammonium nitrate | as per test |
| 1067 | (I-4-a-3) | tetraethylammonium thiosulphate | as per test |
| 1068 | (I-4-a-3) | tetraethylammonium thiocyanate | as per test |
| 1069 | (I-4-a-3) | tetraethylammonium citrate | as per test |
| 1070 | (I-4-a-3) | tetraethylammonium oxalate | as per test |
| 1071 | (I-4-a-3) | tetraethylammonium formate | as per test |
| 1072 | (I-4-a-3) | tetraethylammonium hydrogenphosphate | as per test |
| 1073 | (I-4-a-3) | tetraethylammonium dihydrogenphosphate | as per test |
| 1074 | (I-5-a-1) | ammonium sulphate | as per test |
| 1075 | (I-5-a-1) | ammonium lactate | as per test |
| 1076 | (I-5-a-1) | ammonium nitrate | as per test |
| 1077 | (I-5-a-1) | ammonium thiosulphate | as per test |
| 1078 | (I-5-a-1) | ammonium thiocyanate | as per test |
| 1079 | (I-5-a-1) | ammonium citrate | as per test |
| 1080 | (I-5-a-1) | ammonium oxalate | as per test |
| 1081 | (I-5-a-1) | ammonium formate | as per test |
| 1082 | (I-5-a-1) | ammonium hydrogenphosphate | as per test |
| 1083 | (I-5-a-1) | ammonium dihydrogenphosphate | as per test |
| 1084 | (I-5-a-1) | ammonium carbonate | as per test |
| 1085 | (I-5-a-1) | ammonium benzoate | as per test |
| 1086 | (I-5-a-1) | ammonium sulphite | as per test |
| 1087 | (I-5-a-1) | ammonium benzoate | as per test |
| 1088 | (I-5-a-1) | ammonium hydrogenoxalate | as per test |
| 1089 | (I-5-a-1) | ammonium hydrogencitrate | as per test |
| 1090 | (I-5-a-1) | ammonium acetate | as per test |
| 1091 | (I-5-a-1) | tetramethylammonium sulphate | as per test |
| 1092 | (I-5-a-1) | tetramethylammonium lactate | as per test |
| 1093 | (I-5-a-1) | tetramethylammonium nitrate | as per test |
| 1094 | (I-5-a-1) | tetramethylammonium thiosulphate | as per test |
| 1095 | (I-5-a-1) | tetramethylammonium thiocyanate | as per test |
| 1096 | (I-5-a-1) | tetramethylammonium citrate | as per test |
| 1097 | (I-5-a-1) | tetramethylammonium oxalate | as per test |
| 1098 | (I-5-a-1) | tetramethylammonium formate | as per test |
| 1099 | (I-5-a-1) | tetramethylammonium hydrogenphosphate | as per test |
| 1100 | (I-5-a-1) | tetramethylammonium dihydrogenphosphate | as per test |
| 1101 | (I-5-a-1) | tetraethylammonium sulphate | as per test |
| 1102 | (I-5-a-1) | tetraethylammonium lactate | as per test |
| 1103 | (I-5-a-1) | tetraethylammonium nitrate | as per test |
| 1104 | (I-5-a-1) | tetraethylammonium thiosulphate | as per test |
| 1105 | (I-5-a-1) | tetraethylammonium thiocyanate | as per test |
| 1106 | (I-5-a-1) | tetraethylammonium citrate | as per test |
| 1107 | (I-5-a-1) | tetraethylammonium oxalate | as per test |
| 1108 | (I-5-a-1) | tetraethylammonium formate | as per test |
| 1109 | (I-5-a-1) | tetraethylammonium hydrogenphosphate | as per test |
| 1110 | (I-5-a-1) | tetraethylammonium dihydrogenphosphate | as per test |
| 1111 | (I-6-a-1) | ammonium sulphate | as per test |
| 1112 | (I-6-a-1) | ammonium lactate | as per test |
| 1113 | (I-6-a-1) | ammonium nitrate | as per test |
| 1114 | (I-6-a-1) | ammonium thiosulphate | as per test |
| 1115 | (I-6-a-1) | ammonium thiocyanate | as per test |
| 1116 | (I-6-a-1) | ammonium citrate | as per test |
| 1117 | (I-6-a-1) | ammonium oxalate | as per test |
| 1118 | (I-6-a-1) | ammonium formate | as per test |
| 1119 | (I-6-a-1) | ammonium hydrogenphosphate | as per test |
| 1120 | (I-6-a-1) | ammonium dihydrogenphosphate | as per test |
| 1121 | (I-6-a-1) | ammonium carbonate | as per test |
| 1122 | (I-6-a-1) | ammonium benzoate | as per test |
| 1123 | (I-6-a-1) | ammonium sulphite | as per test |
| 1124 | (I-6-a-1) | ammonium benzoate | as per test |
| 1125 | (I-6-a-1) | ammonium hydrogenoxalate | as per test |
| 1126 | (I-6-a-1) | ammonium hydrogencitrate | as per test |
| 1127 | (I-6-a-1) | ammonium acetate | as per test |
| 1128 | (I-6-a-1) | tetramethylammonium sulphate | as per test |
| 1129 | (I-6-a-1) | tetramethylammonium lactate | as per test |
| 1130 | (I-6-a-1) | tetramethylammonium nitrate | as per test |
| 1131 | (I-6-a-1) | tetramethylammonium thiosulphate | as per test |
| 1132 | (I-6-a-1) | tetramethylammonium thiocyanate | as per test |
| 1133 | (I-6-a-1) | tetramethylammonium citrate | as per test |
| 1134 | (I-6-a-1) | tetramethylammonium oxalate | as per test |
| 1135 | (I-6-a-1) | tetramethylammonium formate | as per test |
| 1136 | (I-6-a-1) | tetramethylammonium hydrogenphosphate | as per test |
| 1137 | (I-6-a-1) | tetramethylammonium dihydrogenphosphate | as per test |
| 1138 | (I-6-a-1) | tetraethylammonium sulphate | as per test |
| 1139 | (I-6-a-1) | tetraethylammonium lactate | as per test |
| 1140 | (I-6-a-1) | tetraethylammonium nitrate | as per test |
| 1141 | (I-6-a-1) | tetraethylammonium thiosulphate | as per test |
| 1142 | (I-6-a-1) | tetraethylammonium thiocyanate | as per test |
| 1143 | (I-6-a-1) | tetraethylammonium citrate | as per test |
| 1144 | (I-6-a-1) | tetraethylammonium oxalate | as per test |
| 1145 | (I-6-a-1) | tetraethylammonium formate | as per test |
| 1146 | (I-6-a-1) | tetraethylammonium hydrogenphosphate | as per test |
| 1147 | (I-6-a-1) | tetraethylammonium dihydrogenphosphate | as per test |
| 1148 | (I-6-a-2) | ammonium sulphate | as per test |
| 1149 | (I-6-a-2) | ammonium lactate | as per test |
| 1150 | (I-6-a-2) | ammonium nitrate | as per test |
| 1151 | (I-6-a-2) | ammonium thiosulphate | as per test |
| 1152 | (I-6-a-2) | ammonium thiocyanate | as per test |
| 1153 | (I-6-a-2) | ammonium citrate | as per test |
| 1154 | (I-6-a-2) | ammonium oxalate | as per test |
| 1155 | (I-6-a-2) | ammonium formate | as per test |
| 1156 | (I-6-a-2) | ammonium hydrogenphosphate | as per test |
| 1157 | (I-6-a-2) | ammonium dihydrogenphosphate | as per test |
| 1158 | (I-6-a-2) | ammonium carbonate | as per test |
| 1159 | (I-6-a-2) | ammonium benzoate | as per test |
| 1160 | (I-6-a-2) | ammonium sulphite | as per test |
| 1161 | (I-6-a-2) | ammonium benzoate | as per test |
| 1162 | (I-6-a-2) | ammonium hydrogenoxalate | as per test |
| 1163 | (I-6-a-2) | ammonium hydrogencitrate | as per test |
| 1164 | (I-6-a-2) | ammonium acetate | as per test |
| 1165 | (I-6-a-2) | tetramethylammonium sulphate | as per test |
| 1166 | (I-6-a-2) | tetramethylammonium lactate | as per test |
| 1167 | (I-6-a-2) | tetramethylammonium nitrate | as per test |
| 1168 | (I-6-a-2) | tetramethylammonium thiosulphate | as per test |
| 1169 | (I-6-a-2) | tetramethylammonium thiocyanate | as per test |
| 1170 | (I-6-a-2) | tetramethylammonium citrate | as per test |
| 1171 | (I-6-a-2) | tetramethylammonium oxalate | as per test |
| 1172 | (I-6-a-2) | tetramethylammonium formate | as per test |
| 1173 | (I-6-a-2) | tetramethylammonium hydrogenphosphate | as per test |
| 1174 | (I-6-a-2) | tetramethylammonium dihydrogenphosphate | as per test |
| 1175 | (I-6-a-2) | tetraethylammonium sulphate | as per test |
| 1176 | (I-6-a-2) | tetraethylammonium lactate | as per test |
| 1177 | (I-6-a-2) | tetraethylammonium nitrate | as per test |
| 1178 | (I-6-a-2) | tetraethylammonium thiosulphate | as per test |
| 1179 | (I-6-a-2) | tetraethylammonium thiocyanate | as per test |
| 1180 | (I-6-a-2) | tetraethylammonium citrate | as per test |
| 1181 | (I-6-a-2) | tetraethylammonium oxalate | as per test |
| 1182 | (I-6-a-2) | tetraethylammonium formate | as per test |
| 1183 | (I-6-a-2) | tetraethylammonium hydrogenphosphate | as per test |
| 1184 | (I-6-a-2) | tetraethylammonium dihydrogenphosphate | as per test |
| 1185 | (I-8-a-1) | ammonium sulphate | as per test |
| 1186 | (I-8-a-1) | ammonium lactate | as per test |
| 1187 | (I-8-a-1) | ammonium nitrate | as per test |
| 1188 | (I-8-a-1) | ammonium thiosulphate | as per test |
| 1189 | (I-8-a-1) | ammonium thiocyanate | as per test |
| 1190 | (I-8-a-1) | ammonium citrate | as per test |
| 1191 | (I-8-a-1) | ammonium oxalate | as per test |
| 1192 | (I-8-a-1) | ammonium formate | as per test |
| 1193 | (I-8-a-1) | ammonium hydrogenphosphate | as per test |
| 1194 | (I-8-a-1) | ammonium dihydrogenphosphate | as per test |
| 1195 | (I-8-a-1) | ammonium carbonate | as per test |
| 1196 | (I-8-a-1) | ammonium benzoate | as per test |
| 1197 | (I-8-a-1) | ammonium sulphite | as per test |
| 1198 | (I-8-a-1) | ammonium benzoate | as per test |
| 1199 | (I-8-a-1) | ammonium hydrogenoxalate | as per test |
| 1200 | (I-8-a-1) | ammonium hydrogencitrate | as per test |
| 1201 | (I-8-a-1) | ammonium acetate | as per test |
| 1202 | (I-8-a-1) | tetramethylammonium sulphate | as per test |
| 1203 | (I-8-a-1) | tetramethylammonium lactate | as per test |
| 1204 | (I-8-a-1) | tetramethylammonium nitrate | as per test |
| 1205 | (I-8-a-1) | tetramethylammonium thiosulphate | as per test |
| 1206 | (I-8-a-1) | tetramethylammonium thiocyanate | as per test |
| 1207 | (I-8-a-1) | tetramethylammonium citrate | as per test |
| 1208 | (I-8-a-1) | tetramethylammonium oxalate | as per test |
| 1209 | (I-8-a-1) | tetramethylammonium formate | as per test |
| 1210 | (I-8-a-1) | tetramethylammonium hydrogenphosphate | as per test |

| # | Active ingredient | Salt | Penetrant |
|---|---|---|---|
| 1211 | (I-8-a-1) | tetramethylammonium dihydrogenphosphate | as per test |
| 1212 | (I-8-a-1) | tetraethylammonium sulphate | as per test |
| 1213 | (I-8-a-1) | tetraethylammonium lactate | as per test |
| 1214 | (I-8-a-1) | tetraethylammonium nitrate | as per test |
| 1215 | (I-8-a-1) | tetraethylammonium thiosulphate | as per test |
| 1216 | (I-8-a-1) | tetraethylammonium thiocyanate | as per test |
| 1217 | (I-8-a-1) | tetraethylammonium citrate | as per test |
| 1218 | (I-8-a-1) | tetraethylammonium oxalate | as per test |
| 1219 | (I-8-a-1) | tetraethylammonium formate | as per test |
| 1220 | (I-8-a-1) | tetraethylammonium hydrogenphosphate | as per test |
| 1221 | (I-8-a-1) | tetraethylammonium dihydrogenphosphate | as per test |
| 1222 | (I-8-a-2) | ammonium sulphate | as per test |
| 1223 | (I-8-a-2) | ammonium lactate | as per test |
| 1224 | (I-8-a-2) | ammonium nitrate | as per test |
| 1225 | (I-8-a-2) | ammonium thiosulphate | as per test |
| 1226 | (I-8-a-2) | ammonium thiocyanate | as per test |
| 1227 | (I-8-a-2) | ammonium citrate | as per test |
| 1228 | (I-8-a-2) | ammonium oxalate | as per test |
| 1229 | (I-8-a-2) | ammonium formate | as per test |
| 1230 | (I-8-a-2) | ammonium hydrogenphosphate | as per test |
| 1231 | (I-8-a-2) | ammonium dihydrogenphosphate | as per test |
| 1232 | (I-8-a-2) | ammonium carbonate | as per test |
| 1233 | (I-8-a-2) | ammonium benzoate | as per test |
| 1234 | (I-8-a-2) | ammonium sulphite | as per test |
| 1235 | (I-8-a-2) | ammonium benzoate | as per test |
| 1236 | (I-8-a-2) | ammonium hydrogenoxalate | as per test |
| 1237 | (I-8-a-2) | ammonium hydrogencitrate | as per test |
| 1238 | (I-8-a-2) | ammonium acetate | as per test |
| 1239 | (I-8-a-2) | tetramethylammonium sulphate | as per test |
| 1240 | (I-8-a-2) | tetramethylammonium lactate | as per test |
| 1241 | (I-8-a-2) | tetramethylammonium nitrate | as per test |
| 1242 | (I-8-a-2) | tetramethylammonium thiosulphate | as per test |
| 1243 | (I-8-a-2) | tetramethylammonium thiocyanate | as per test |
| 1244 | (I-8-a-2) | tetramethylammonium citrate | as per test |
| 1245 | (I-8-a-2) | tetramethylammonium oxalate | as per test |
| 1246 | (I-8-a-2) | tetramethylammonium formate | as per test |
| 1247 | (I-8-a-2) | tetramethylammonium hydrogenphosphate | as per test |
| 1248 | (I-8-a-2) | tetramethylammonium dihydrogenphosphate | as per test |
| 1249 | (I-8-a-2) | tetraethylammonium sulphate | as per test |
| 1250 | (I-8-a-2) | tetraethylammonium lactate | as per test |
| 1251 | (I-8-a-2) | tetraethylammonium nitrate | as per test |
| 1252 | (I-8-a-2) | tetraethylammonium thiosulphate | as per test |
| 1253 | (I-8-a-2) | tetraethylammonium thiocyanate | as per test |
| 1254 | (I-8-a-2) | tetraethylammonium citrate | as per test |
| 1255 | (I-8-a-2) | tetraethylammonium oxalate | as per test |
| 1256 | (I-8-a-2) | tetraethylammonium formate | as per test |
| 1257 | (I-8-a-2) | tetraethylammonium hydrogenphosphate | as per test |
| 1258 | (I-8-a-2) | tetraethylammonium dihydrogenphosphate | as per test |
| 1259 | (I-8-a-3) | ammonium sulphate | as per test |
| 1260 | (I-8-a-3) | ammonium lactate | as per test |
| 1261 | (I-8-a-3) | ammonium nitrate | as per test |
| 1262 | (I-8-a-3) | ammonium thiosulphate | as per test |
| 1263 | (I-8-a-3) | ammonium thiocyanate | as per test |
| 1264 | (I-8-a-3) | ammonium citrate | as per test |
| 1265 | (I-8-a-3) | ammonium oxalate | as per test |
| 1266 | (I-8-a-3) | ammonium formate | as per test |
| 1267 | (I-8-a-3) | ammonium hydrogenphosphate | as per test |
| 1268 | (I-8-a-3) | ammonium dihydrogenphosphate | as per test |
| 1269 | (I-8-a-3) | ammonium carbonate | as per test |
| 1270 | (I-8-a-3) | ammonium benzoate | as per test |
| 1271 | (I-8-a-3) | ammonium sulphite | as per test |
| 1272 | (I-8-a-3) | ammonium benzoate | as per test |
| 1273 | (I-8-a-3) | ammonium hydrogenoxalate | as per test |
| 1274 | (I-8-a-3) | ammonium hydrogencitrate | as per test |
| 1275 | (I-8-a-3) | ammonium acetate | as per test |
| 1276 | (I-8-a-3) | tetramethylammonium sulphate | as per test |
| 1277 | (I-8-a-3) | tetramethylammonium lactate | as per test |
| 1278 | (I-8-a-3) | tetramethylammonium nitrate | as per test |
| 1279 | (I-8-a-3) | tetramethylammonium thiosulphate | as per test |
| 1280 | (I-8-a-3) | tetramethylammonium thiocyanate | as per test |
| 1281 | (I-8-a-3) | tetramethylammonium citrate | as per test |
| 1282 | (I-8-a-3) | tetramethylammonium oxalate | as per test |
| 1283 | (I-8-a-3) | tetramethylammonium formate | as per test |
| 1284 | (I-8-a-3) | tetramethylammonium hydrogenphosphate | as per test |
| 1285 | (I-8-a-3) | tetramethylammonium dihydrogenphosphate | as per test |
| 1286 | (I-8-a-3) | tetraethylammonium sulphate | as per test |
| 1287 | (I-8-a-3) | tetraethylammonium lactate | as per test |
| 1288 | (I-8-a-3) | tetraethylammonium nitrate | as per test |
| 1289 | (I-8-a-3) | tetraethylammonium thiosulphate | as per test |
| 1290 | (I-8-a-3) | tetraethylammonium thiocyanate | as per test |
| 1291 | (I-8-a-3) | tetraethylammonium citrate | as per test |
| 1292 | (I-8-a-3) | tetraethylammonium oxalate | as per test |
| 1293 | (I-8-a-3) | tetraethylammonium formate | as per test |
| 1294 | (I-8-a-3) | tetraethylammonium hydrogenphosphate | as per test |
| 1295 | (I-8-a-3) | tetraethylammonium dihydrogenphosphate | as per test |
| 1296 | (I-8-a-4) | ammonium sulphate | as per test |
| 1297 | (I-8-a-4) | ammonium lactate | as per test |
| 1298 | (I-8-a-4) | ammonium nitrate | as per test |
| 1299 | (I-8-a-4) | ammonium thiosulphate | as per test |
| 1300 | (I-8-a-4) | ammonium thiocyanate | as per test |
| 1301 | (I-8-a-4) | ammonium citrate | as per test |
| 1302 | (I-8-a-4) | ammonium oxalate | as per test |
| 1303 | (I-8-a-4) | ammonium formate | as per test |
| 1304 | (I-8-a-4) | ammonium hydrogenphosphate | as per test |
| 1305 | (I-8-a-4) | ammonium dihydrogenphosphate | as per test |
| 1306 | (I-8-a-4) | ammonium carbonate | as per test |
| 1307 | (I-8-a-4) | ammonium benzoate | as per test |
| 1308 | (I-8-a-4) | ammonium sulphite | as per test |
| 1309 | (I-8-a-4) | ammonium benzoate | as per test |
| 1310 | (I-8-a-4) | ammonium hydrogenoxalate | as per test |
| 1311 | (I-8-a-4) | ammonium hydrogencitrate | as per test |
| 1312 | (I-8-a-4) | ammonium acetate | as per test |
| 1313 | (I-8-a-4) | tetramethylammonium sulphate | as per test |
| 1314 | (I-8-a-4) | tetramethylammonium lactate | as per test |
| 1315 | (I-8-a-4) | tetramethylammonium nitrate | as per test |
| 1316 | (I-8-a-4) | tetramethylammonium thiosulphate | as per test |
| 1317 | (I-8-a-4) | tetramethylammonium thiocyanate | as per test |
| 1318 | (I-8-a-4) | tetramethylammonium citrate | as per test |
| 1319 | (I-8-a-4) | tetramethylammonium oxalate | as per test |
| 1320 | (I-8-a-4) | tetramethylammonium formate | as per test |
| 1321 | (I-8-a-4) | tetramethylammonium hydrogenphosphate | as per test |
| 1322 | (I-8-a-4) | tetramethylammonium dihydrogenphosphate | as per test |
| 1323 | (I-8-a-4) | tetraethylammonium sulphate | as per test |
| 1324 | (I-8-a-4) | tetraethylammonium lactate | as per test |
| 1325 | (I-8-a-4) | tetraethylammonium nitrate | as per test |
| 1326 | (I-8-a-4) | tetraethylammonium thiosulphate | as per test |
| 1327 | (I-8-a-4) | tetraethylammonium thiocyanate | as per test |
| 1328 | (I-8-a-4) | tetraethylammonium citrate | as per test |
| 1329 | (I-8-a-4) | tetraethylammonium oxalate | as per test |
| 1330 | (I-8-a-4) | tetraethylammonium formate | as per test |
| 1331 | (I-8-a-4) | tetraethylammonium hydrogenphosphate | as per test |
| 1332 | (I-8-a-4) | tetraethylammonium dihydrogenphosphate | as per test |
| 1333 | (I-9-a-1) | ammonium sulphate | as per test |
| 1334 | (I-9-a-1) | ammonium lactate | as per test |
| 1335 | (I-9-a-1) | ammonium nitrate | as per test |
| 1336 | (I-9-a-1) | ammonium thiosulphate | as per test |
| 1337 | (I-9-a-1) | ammonium thiocyanate | as per test |
| 1338 | (I-9-a-1) | ammonium citrate | as per test |
| 1339 | (I-9-a-1) | ammonium oxalate | as per test |
| 1340 | (I-9-a-1) | ammonium formate | as per test |
| 1341 | (I-9-a-1) | ammonium hydrogenphosphate | as per test |
| 1342 | (I-9-a-1) | ammonium dihydrogenphosphate | as per test |
| 1343 | (I-9-a-1) | ammonium carbonate | as per test |
| 1344 | (I-9-a-1) | ammonium benzoate | as per test |
| 1345 | (I-9-a-1) | ammonium sulphite | as per test |
| 1346 | (I-9-a-1) | ammonium benzoate | as per test |
| 1347 | (I-9-a-1) | ammonium hydrogenoxalate | as per test |
| 1348 | (I-9-a-1) | ammonium hydrogencitrate | as per test |
| 1349 | (I-9-a-1) | ammonium acetate | as per test |
| 1350 | (I-9-a-1) | tetramethylammonium sulphate | as per test |
| 1351 | (I-9-a-1) | tetramethylammonium lactate | as per test |
| 1352 | (I-9-a-1) | tetramethylammonium nitrate | as per test |
| 1353 | (I-9-a-1) | tetramethylammonium thiosulphate | as per test |
| 1354 | (I-9-a-1) | tetramethylammonium thiocyanate | as per test |
| 1355 | (I-9-a-1) | tetramethylammonium citrate | as per test |
| 1356 | (I-9-a-1) | tetramethylammonium oxalate | as per test |
| 1357 | (I-9-a-1) | tetramethylammonium formate | as per test |
| 1358 | (I-9-a-1) | tetramethylammonium hydrogenphosphate | as per test |

-continued

| # | Active ingredient | Salt | Penetrant |
|---|---|---|---|
| 1359 | (I-9-a-1) | tetramethylammonium dihydrogenphosphate | as per test |
| 1360 | (I-9-a-1) | tetraethylammonium sulphate | as per test |
| 1361 | (I-9-a-1) | tetraethylammonium lactate | as per test |
| 1362 | (I-9-a-1) | tetraethylammonium nitrate | as per test |
| 1363 | (I-9-a-1) | tetraethylammonium thiosulphate | as per test |
| 1364 | (I-9-a-1) | tetraethylammonium thiocyanate | as per test |
| 1365 | (I-9-a-1) | tetraethylammonium citrate | as per test |
| 1366 | (I-9-a-1) | tetraethylammonium oxalate | as per test |
| 1367 | (I-9-a-1) | tetraethylammonium formate | as per test |
| 1368 | (I-9-a-1) | tetraethylammonium hydrogenphosphate | as per test |
| 1369 | (I-9-a-1) | tetraethylammonium dihydrogenphosphate | as per test |
| 1370 | (I-10-a-1) | ammonium sulphate | as per test |
| 1371 | (I-10-a-1) | ammonium lactate | as per test |
| 1372 | (I-10-a-1) | ammonium nitrate | as per test |
| 1373 | (I-10-a-1) | ammonium thiosulphate | as per test |
| 1374 | (I-10-a-1) | ammonium thiocyanate | as per test |
| 1375 | (I-10-a-1) | ammonium citrate | as per test |
| 1376 | (I-10-a-1) | ammonium oxalate | as per test |
| 1377 | (I-10-a-1) | ammonium formate | as per test |
| 1378 | (I-10-a-1) | ammonium hydrogenphosphate | as per test |
| 1379 | (I-10-a-1) | ammonium dihydrogenphosphate | as per test |
| 1380 | (I-10-a-1) | ammonium carbonate | as per test |
| 1381 | (I-10-a-1) | ammonium benzoate | as per test |
| 1382 | (I-10-a-1) | ammonium sulphite | as per test |
| 1383 | (I-10-a-1) | ammonium benzoate | as per test |
| 1384 | (I-10-a-1) | ammonium hydrogenoxalate | as per test |
| 1385 | (I-10-a-1) | ammonium hydrogencitrate | as per test |
| 1386 | (I-10-a-1) | ammonium acetate | as per test |
| 1387 | (I-10-a-1) | tetramethylammonium sulphate | as per test |
| 1388 | (I-10-a-1) | tetramethylammonium lactate | as per test |
| 1389 | (I-10-a-1) | tetramethylammonium nitrate | as per test |
| 1390 | (I-10-a-1) | tetramethylammonium thiosulphate | as per test |
| 1391 | (I-10-a-1) | tetramethylammonium thiocyanate | as per test |
| 1392 | (I-10-a-1) | tetramethylammonium citrate | as per test |
| 1393 | (I-10-a-1) | tetramethylammonium oxalate | as per test |
| 1394 | (I-10-a-1) | tetramethylammonium formate | as per test |
| 1395 | (I-10-a-1) | tetramethylammonium hydrogenphosphate | as per test |
| 1396 | (I-10-a-1) | tetramethylammonium dihydrogenphosphate | as per test |
| 1397 | (I-10-a-1) | tetraethylammonium sulphate | as per test |
| 1398 | (I-10-a-1) | tetraethylammonium lactate | as per test |
| 1399 | (I-10-a-1) | tetraethylammonium nitrate | as per test |
| 1400 | (I-10-a-1) | tetraethylammonium thiosulphate | as per test |
| 1401 | (I-10-a-1) | tetraethylammonium thiocyanate | as per test |
| 1402 | (I-10-a-1) | tetraethylammonium citrate | as per test |
| 1403 | (I-10-a-1) | tetraethylammonium oxalate | as per test |
| 1404 | (I-10-a-1) | tetraethylammonium formate | as per test |
| 1405 | (I-10-a-1) | tetraethylammonium hydrogenphosphate | as per test |
| 1406 | (I-10-a-1) | tetraethylammonium dihydrogenphosphate | as per test |

Crop protection materials of the invention may also comprise further components, examples being surfactants and/or dispersing assistants or emulsifiers.

Suitable nonionic surfactants and/or dispersing assistants include all substances of this type that can typically be used in agrochemical compositions. Preferably mention may be made of polyethylene oxide-polypropylene oxide block copolymers, polyethylene glycol ethers of linear alcohols, reaction products of fatty acids with ethylene oxide and/or propylene oxide, and also polyvinyl alcohol, polyvinylpyrrolidone, copolymers of polyvinyl alcohol and polyvinylpyrrolidone, and copolymers of (meth)acrylic acid and (meth) acrylic esters, and additionally alkyl ethoxylates and alkylaryl ethoxylates, which optionally may be phosphated and optionally may be neutralized with bases, mention being made, by way of example, of sorbitol ethoxylates, and, as well, polyoxyalkylenamine derivatives.

Suitable anionic surfactants include all substances of this type that can typically be used in agrochemical compositions. Preference is given to alkali metal salts and alkaline earth metal salts of alkylsulphonic acids or alkylarylsulphonic acids.

A further preferred group of anionic surfactants and/or dispersing assistants are the following salts that are of low solubility in plant oil: salts of polystyrenesulphonic acids, salts of polyvinylsulphonic acids, salts of naphthalenesulphonic acid-formaldehyde condensation products, salts of condensation products of naphthalenesulphonic acid, phenolsulphonic acid and formaldehyde, and salts of ligninsulphonic acid.

Suitable additives which may be included in the formulations of the invention are emulsifiers, foam inhibitors, preservatives, antioxidants, colorants and inert filling materials.

Preferred emulsifiers are ethoxylated nonylphenols, reaction products of alkylphenols with ethylene oxide and/or propylene oxide, ethoxylated arylalkylphenols, and also ethoxylated and propoxylated arylalkylphenols, and also sulphated or phosphated arylalkyl ethoxylates and/or arylalkyl ethoxy-propoxylates, mention being made by way of example of sorbitan derivatives, such as polyethylene oxide-sorbitan fatty acid esters, and sorbitan fatty acid esters.

The examples which follow serve to illustrate the invention and should in no way be interpreted as being restrictive.

Example A-1: Boosting plant penetration by means of ammonium or phosphonium salts and synergistically boosting plant penetration by means of ammonium/phosphonium salts in combination with penetrants This test measured the penetration of active ingredients through enzymatically isolated cuticles of apple leaves.

The leaves used were cut in the fully developed state from apple trees of the Golden Delicious variety. The cuticles were isolated as follows:

first of all, leaf discs marked on the underside with dye and formed by punching were filled by means of vacuum infiltration with a pectinase solution (0.2% to 2% strength) buffered to a pH of between 3 and 4, then sodium azide was added and the leaf discs thus treated were left to stand until the original leaf structure broke down and the non-cellular cuticle underwent detachment.

Thereafter only those cuticles from the top leaf sides that were free from stomata and hairs were used. They were washed a number of times in alternation with water and with a buffer solution of pH 7. The clean cuticles obtained were, finally, applied to Teflon plaques, smoothed with a gentle jet of air, and dried.

In the next step the cuticular membranes obtained in this way were placed in stainless steel diffusion cells (i.e. transport chambers) for the purpose of membrane transport investigations. For these investigations the cuticles were placed centrally using tweezers on the edges of the diffusion cells, which were coated with silicone grease, and sealed with a ring, which was likewise greased. The arrangement had been chosen so that the morphological outer face of the cuticles was directed outwards, in other words to the air, while the original inner side was facing the interior of the diffusion cell.

The diffusion cells were filled with a 30% strength ethylene glycol/water solution. Penetration was determined by applying 10 μl of the spray liquor, whose composition is indicated below, to the outer face of each cuticle. The spray liquor is made up using local tap water of medium hardness.

After the spray liquors had been applied, the water was evaporated and the chambers were then inverted and placed in thermostated troughs in which the temperature and atmospheric humidity above the cuticle was adjustable by means of a gentle stream of air onto the cuticle with the spray coating (20° C., 60% rh). At regular intervals an autosampler took aliquots which were assayed for active ingredient by HPLC.

The results of the experiment are apparent from the table below. The figures indicated are average values from 8 to 10 measurements. It is clearly apparent that ammonium sulphate alone already significantly enhances penetration and that together with RME there is a superadditive (synergistic) effect.

TABLE A-1

| Active ingredient | Penetration after 24 h/% | | | |
|---|---|---|---|---|
| | EC | EC + AS (1 g/l) | EC + RME (1 g/l) | EC + RME (1 g/l) + AS (1 g/l) |
| Example I-1-a-1 (structure) | 0.6 | 2.5 | 13.5 | 41 |

Example I-1-a-1
500 ppm in DMF/Emulgator W 7:1 (w/w)

RME = Rapeseed oil methyl ester (formulated for use as 500 EW, concentration figure in g active ingredient/l)
AS = ammonium sulphate
EC = emulsifiable concentrate
Emulgator W = emulsifier Example A-2

Example A-2 was carried out in the same way as in Example A-1.

TABLE A-2

| Active ingredient | Penetration after 24 h/% | | |
|---|---|---|---|
| | EC | EC + RME (1 g/l) | EC + RME (1 g/l) + AT (1 g/l) |
| Example I-1-a-1 (structure) | <0.2 | 3.5 | 12 |

Example I-1-a-1
500 ppm in DMF/EmulgatorW 7:1 (w/w)

RME = Rapeseed oil methyl ester (formulated for use as 500 EW, concentration figure in g active ingredient/l)
AT = ammonium thiocyanate
EC = emulsifiable concentrate
Emulgator W = emulsifier Example A-3

Example A-3 was carried out in the same way as in Example A-1.

TABLE A-3

| Active ingredient | Penetration after 24 h/% | | | |
|---|---|---|---|---|
| | EC + RME (1 g/l) | EC + RME (1 g/l) + salt (1 g/l) | | |
| | | Salt | Penetration after 24 h/% | |
| Example I-1-a-1 (structure) | 10 | Diammonium hydrogen-phosphate | 26 | |
| | | Ammonium dihydrogen-phosphate | 42 | |

Example I-1-a-1
500 ppm in DMF/Emulgator W 7:1 (w/w)

RME = Rapeseed oil methyl ester (formulated for use as 500 EW, concentration figure in g active ingredient/l)
EC = emulsifiable concentrate
Emulgator W = emulsifier Example B: Activity boosting by means of ammonium/phosphonium salts The following data demonstrate that ammonium salts and/or phosphonium salts are capable of boosting further the activity of ketoenol-containing crop protection compositions.

*Myzus persicae* test

Solvent: 7 parts by weight dimethylformamide
Emulsifier: 1 part by weight alkylaryl polyglycol ether An appropriate preparation of active ingredient is prepared by mixing 1 part by weight of active ingredient with the stated amounts of solvent and emulsifier and diluting the concentrate with water to the desired concentration. Where it is necessary to add ammonium salts, phosphonium salts or penetrant, the appropriate amount is added by pipette, after dilution, to each of the ready-prepared product solutions. Single-leaf paprika plants (*Capsicum annuum*) heavily infested by the green peach aphid (*Myzus persicae*) are treated by spraying the top side of the leaf (spray volume 600 1/ha) with the preparation of active ingredient at the desired concentration. After the desired time the destruction in % is ascertained. 100% means that all of the animals have been killed; 0% means that no animals have been killed.

TABLE B

| Active ingredient | Active ingredient g/ha | Degree of destruction/% after 3 days | |
|---|---|---|---|
| | | No AS | AS (1 g/1) |
| Ex. I-1-c-1 | 120 | 37 | 67 |

AS = ammonium sulphate

Example C: Activity boosting by means of ammonium/phosphonium salts in combination with penetrants The following data demonstrate that ammonium salts and/or phosphonium salts are capable of boosting activity still further even when ready-to-apply crop protection compositions which comprise penetrants in order to boost activity are applied.

*Myzus persicae* test

Solvent: 7 parts by weight dimethylformamide

Emulsifier: 1 part by weight alkylaryl polyglycol ether

An appropriate preparation of active ingredient is prepared by mixing 1 part by weight of active ingredient with the stated amounts of solvent and emulsifier and diluting the concentrate with water to the desired concentration. Where it is necessary to add ammonium salts, phosphonium salts or penetrant, the appropriate amount is added by pipette, after dilution, to each of the ready prepared product solutions. Single-leaf paprika plants (*Capsicum annuum*) heavily infested by the green peach aphid (*Myzus persicae*) are treated by spraying the top side of the leaf (spray volume 600 1/ha) with the preparation of active ingredient at the desired concentration. After the desired time the destruction in % is ascertained. 100% means that all of the animals have been killed; 0% means that no animals have been killed.

TABLE C

| Active ingredient | Active ingredient g / ha | Degree of destruction/% after 4 days | |
|---|---|---|---|
| | | RME (1 g/l) | RME (1 g/l) + AS (1 g/l) |
| Ex. I-1-a-2 | 120 | 37 | 92 |

RME = Rapeseed oil methyl ester (formulated for use as 500 EW, concentration figure in g active ingredient/l)
AS = ammonium sulphate Example D: Activity boosting by means of ammonium/phosphonium salts

*Myzus persicae* test

Solvent: 7 parts by weight dimethylformamide

Emulsifier: 2 parts by weight alkylaryl polyglycol ether

An appropriate preparation of active ingredient is prepared by mixing 1 part by weight of active ingredient with the stated amounts of solvent and emulsifier and diluting the concentrate with water to the desired concentration. For the application with ammonium salts or phosphonium salts, these salts are added in a concentration of 1000 ppm to the spray liquor.

Paprika plants (*Capsicum annum*) heavily infested by the green peach aphid (*Myzus persicae*) are treated by being sprayed to runoff with the preparation of active ingredient at the desired concentration. After the desired time the destruction in % is ascertained. 100% means that all of the animals have been killed; 0% means that no animals have been killed.

TABLE D

| Active ingredient | Active ingredient ppm | Degree of destruction/% after 6 days |
|---|---|---|
| | | +AS (1000 ppm) |
| I-1-a-3 | 20 | 60 75 |
| I-1-a-3 | 4 | 0 90 |
| I-1-a-4 | 20 | 95 98 |
| I-1-a-4 | 4 | 40 65 |
| I-1-a-5 | 4 | 90 98 |
| I-1-a-7 | 4 | 40 80 |
| I-1-a-8 | 0.8 | 20 55 |
| I-1-a-10 | 20 | 40 85 |
| I-1-a-10 | 4 | 0 35 |
| I-1-a-11 | 20 | 0 70 |
| I-1-a-12 | 20 | 55 65 |
| I-2-a-1 | 4 | 90 98 |
| I-2-a-1 | 0.8 | 20 65 |
| I-2-a-2 | 4 | 65 90 |
| I-2-a-2 | 0.8 | 0 25 |
| I-2-a-3 | 20 | 0 15 |
| I-2-a-4 | 20 | 60 80 |
| I-4-a-1 | 20 | 75 95 |
| I-4-a-1 | 4 | 0 45 |
| I-4-a-3 | 20 | 40 85 |

TABLE D-continued

| Active ingredient | ppm | Degree of destruction/% after 6 days +AS (1000 ppm) |
|---|---|---|
| I-4-a-3 | 4 | 5 / 70 |
| I-5-a-1 | 20 | 0 / 55 |
| I-10-a-1 | 20 | 0 / 25 |

AS = Ammonium sulphate

Example E

*Aphis gossypii* test

Solvent: 7 parts by weight dimethylformamide

Emulsifier: 2 parts by weight alkylaryl polyglycol ether

An appropriate preparation of active ingredient is prepared by mixing 1 part by weight of active ingredient with the stated amounts of solvent and emulsifier and diluting the concentrate with water to the desired concentration. For the application with ammonium salts or phosphonium salts, these salts are added in a concentration of 1000 ppm to the spray liquor.

Cotton plants (*Gossypium hirsutum*) heavily infested by the cotton aphid (*Aphis gossypii*) are sprayed to runoff with the preparation of active ingredient at the desired concentration.

After the desired time the destruction in % is ascertained. 100% means that all of the aphids have been killed; 0% means than no aphids were killed.

TABLE E

| Active ingredient | Active ingredient ppm | Degree of destruction/% after 6 days +AS (1000 ppm) |
|---|---|---|
| I-1-a-3 | 20 | 20 / 80 |
| I-1-a-3 | 4 | 5 / 35 |
| I-1-a-4 | 4 | 60 / 85 |
| I-1-a-4 | 0.8 | 15 / 65 |
| I-1-a-5 | 0.8 | 35 / 55 |
| I-1-a-6 | 4 | 25 / 55 |
| I-1-a-6 | 0.8 | 15 / 30 |
| I-1-a-7 | 20 | 85 / 99 |
| I-1-a-7 | 4 | 55 / 90 |
| I-1-a-8 | 0.8 | 0 / 40 |
| I-1-a-10 | 20 | 40 / 75 |
| I-1-a-10 | 4 | 20 / 65 |
| I-1-a-11 | 20 | 45 / 80 |
| I-1-a-11 | 4 | 5 / 35 |
| I-1-a-12 | 4 | 65 / 95 |
| I-1-a-12 | 0.8 | 5 / 45 |
| I-1-a-14 | 4 | 55 / 90 |
| I-1-a-14 | 0.8 | 25 / 40 |
| I-1-a-15 | 20 | 80 / 95 |
| I-1-a-15 | 4 | 40 / 75 |
| I-1-a-16 | 20 | 75 / 85 |
| I-1-a-16 | 4 | 40 / 75 |
| I-1-a-17 | 20 | 70 / 85 |
| I-1-a-17 | 4 | 50 / 80 |
| I-2-a-1 | 4 | 80 / 95 |
| I-2-a-1 | 0.8 | 0 / 85 |
| I-2-a-2 | 4 | 85 / 95 |
| I-2-a-2 | 0.8 | 30 / 70 |
| I-2-a-3 | 20 | 0 / 30 |
| I-2-a-4 | 4 | 70 / 90 |
| I-2-a-4 | 0.8 | 10 / 45 |
| I-4-a-1 | 4 | 0 / 40 |
| I-4-a-2 | 4 | 50 / 60 |
| I-4-a-3 | 4 | 25 / 70 |
| I-4-a-3 | 0.8 | 0 / 40 |
| I-10-a-1 | 20 | 0 / 45 |

TABLE E-continued

| Active ingredient | Active ingredient ppm | Degree of destruction/% after 6 days +AS (1000 ppm) |
|---|---|---|
| I-10-a-2 | 20 | 10 / 80 |
| I-10-a-2 | 4 | 0 / 50 |

AS = Ammonium sulphate

Example F: Activity boosting by means of ammonium/phosphonium salts in combination with penetrants

*Myzus persicae* test

Solvent: 7 parts by weight dimethylformamide

Emulsifier: 2 parts by weight alkylaryl polyglycol ether

An appropriate preparation of active ingredient is prepared by mixing 1 part by weight of active ingredient with the stated amounts of solvent and emulsifier and diluting the concentrate with water to the desired concentration. For the application with ammonium salts or phosphonium salts and penetrant (rapeseed oil methyl ester 500 EW), they are each added in a concentration of 1000 ppm to the spray liquor.

Paprika plants (*Capsicum annuum*) heavily infested by the green peach aphid (*Myzus persicae*) are treated by being sprayed to runoff with the preparation of active ingredient at the desired concentration. After the desired time the destruction in % is ascertained. 100% means that all of the animals have been killed; 0% means that no animals have been killed.

TABLE F

| Active ingredient | Concentration / ppm | Degree of destruction/% after 6 days | | |
|---|---|---|---|---|
| | | +AS (1000 ppm) | +RME (1000 ppm) | +RME +AS (each 1000 ppm) |
| I-1-a-3 | 4 | 0 | 20 | 10 | 90 |
| I-1-a-4 | 4 | 40 | 65 | 95 | 98 |
| I-1-a-4 | 0.8 | 0 | 5 | 0 | 20 |
| I-1-a-5 | 4 | 90 | 98 | 98 | 100 |
| I-1-a-5 | 0.8 | 0 | 0 | 95 | 99 |
| I-1-a-7 | 0.8 | 0 | 10 | 35 | 75 |
| I-1-a-8 | 0.8 | 20 | 55 | 60 | 80 |
| I-1-a-9 | 0.8 | 0 | 5 | 35 | 75 |
| I-1-a-10 | 4 | 0 | 35 | 75 | 85 |
| I-1-a-11 | 4 | 0 | 5 | 55 | 99 |
| I-1-a-12 | 20 | 55 | 65 | 70 | 98 |
| I-1-a-12 | 4 | 0 | 5 | 0 | 50 |
| I-1-a-13 | 4 | 0 | 0 | 65 | 75 |
| I-1-a-13 | 0.8 | 0 | 0 | 0 | 30 |
| I-1-a-15 | 0.8 | 15 | 0 | 50 | 80 |
| I-1-a-18 | 4 | 0 | 0 | 35 | 55 |
| I-2-a-1 | 0.8 | 20 | 65 | 95 | 100 |
| I-2-a-2 | 0.8 | 0 | 25 | 15 | 99 |
| I-2-a-3 | 20 | 0 | 15 | 35 | 80 |
| I-2-a-4 | 4 | 0 | 0 | 0 | 70 |
| I-4-a-1 | 0.8 | 0 | 5 | 0 | 40 |
| I-4-a-3 | 0.8 | 0 | 5 | 20 | 98 |
| I-5-a-1 | 4 | 0 | 5 | 55 | 95 |
| I-8-a-1 | 100 | 15 | 30 | 30 | 45 |
| I-8-a-2 | 100 | 0 | 15 | 15 | 55 |
| I-9-a-1 | 100 | 15 | 0 | 5 | 50 |
| I-10-a-1 | 20 | 0 | 25 | 65 | 99 |
| I-10-a-1 | 4 | 0 | 5 | 20 | 55 |
| I-10-a-2 | 20 | 5 | 10 | 0 | 65 |

RME = Rapeseed oil methyl ester (formulated as 500 EW, concentration figure in g active ingredient/l)
AS = Ammonium sulphate Example G

*Aphis gossypii* test

Solvent: 7 parts by weight dimethylformamide

Emulsifier: 2 parts by weight alkylaryl polyglycol ether

An appropriate preparation of active ingredient is prepared by mixing 1 part by weight of active ingredient with the stated amounts of solvent and emulsifier and diluting the concentrate with emulsifier-containing water to the desired concentration. For the application with ammonium salts or phosphonium salts and penetrants (rapeseed oil methyl esters 500 EW), they are each added in a concentration of 1000 ppm a.i. to the spray liquor.

Cotton plants (*Gossypium hirsutum*) heavily infested by the cotton aphid (*Aphis gossypii*) are sprayed to runoff with the preparation of active ingredient at the desired concentration.

After the desired time the destruction in % is ascertained. 100% means that all of the aphids have been killed; 0% means than no aphids were killed.

TABLE G

| Active ingredient | Concentration / ppm | Degree of destruction/% after 6 days | | |
|---|---|---|---|---|
| | | +AS (1000 ppm) | +RME (1000 ppm) | +RME +AS (each 1000 ppm) |
| I-1-a-4 | 0.8 | 15 | 65 | 30 | 80 |
| I-1-a-5 | 0.8 | 35 | 55 | 45 | 85 |
| I-1-a-6 | 4 | 25 | 55 | 50 | 80 |
| I-1-a-7 | 4 | 55 | 90 | 85 | 95 |
| I-1-a-7 | 0.8 | 35 | 45 | 50 | 75 |
| I-1-a-8 | 0.8 | 0 | 40 | 20 | 60 |
| I-1-a-11 | 4 | 5 | 35 | 45 | 80 |
| I-1-a-12 | 0.8 | 5 | 45 | 45 | 65 |
| I-1-a-16 | 20 | 75 | 85 | 95 | 99 |
| I-1-c-2 | 20 | 85 | 85 | 90 | 99 |
| I-2-a-2 | 0.8 | 30 | 70 | 50 | 95 |
| I-2-a-3 | 20 | 0 | 30 | 0 | 65 |
| I-2-a-3 | 4 | 0 | 5 | 0 | 15 |
| I-2-a-4 | 0.8 | 10 | 45 | 45 | 70 |
| I-4-a-1 | 0.8 | 0 | 15 | 0 | 45 |
| I-4-a-2 | 4 | 5 | 60 | 0 | 65 |
| I-4-a-3 | 0.8 | 0 | 40 | 0 | 80 |
| I-6-a-1 | 100 | 40 | 40 | 60 | 80 |
| I-6-a-2 | 100 | 0 | 30 | 15 | 40 |
| I-8-a-1 | 100 | 0 | 15 | 15 | 40 |
| I-8-a-3 | 20 | 15 | 50 | 50 | 90 |
| I-8-a-4 | 90 | 30 | 35 | 30 | 75 |
| I-10-a-1 | 20 | 0 | 45 | 45 | 70 |

RME = Rapeseed oil methyl ester (formulated as 500 EW, concentration figure in g active ingredient/l)
AS = Ammonium sulphate

The invention claimed is:
1. Composition comprising
spirotetramat
and at least one salt of formula (II)

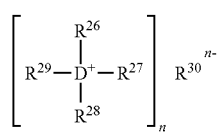 (II)

in which
D is nitrogen or phosphorus,
$R^{26}$, $R^{27}$, $R^{28}$ and $R^{29}$ independently of one another are hydrogen or in each case optionally substituted $C_1$-$C_8$-alkyl or singly or multiply unsaturated, optionally substituted $C_1$-$C_8$-alkylene, the substituents being selectable from the group consisting of halogen, nitro and cyano, n is 1, 2, 3 or 4,
$R^{30}$ is an organic or inorganic anion.

2. Composition according to claim 1, wherein the spirotetramat content is between 0.5% and 50% by weight.

3. Composition according to claim 1, wherein the amount of salt is between 0.5 and 80 mmol/l.

4. Composition according to claim 1, wherein D is nitrogen.

5. Composition according to claim 4, wherein $R^{30}$ is hydrogencarbonate, tetraborate, fluoride, bromide, iodide, chloride, monohydrogenphosphate, dihydrogenphosphate, hydrogensulphate, tartrate, sulphate, nitrate, thiosulphate, thiocyanate, formate, lactate, acetate, propionate, butyrate, pentanoate, citrate or oxalate.

6. Composition according to claim 4, wherein $R^{30}$ is carbonate, pentaborate, sulphite, benzoate, hydrogenoxalate, hydrogencitrate, methylsulphate or tetrafluoroborate.

7. Composition according to claim 4, wherein $R^{30}$ is lactate, sulphate, nitrate, thiosulphate, thiocyanate, citrate, oxalate or formate.

8. Composition according to claim 4, wherein $R^{30}$ is thiocyanate, dihydrogenphosphate, monohydrogenphosphate or sulphate.

9. Composition according to claim 1, further comprising at least one penetrant.

10. Composition according to claim 9, wherein the penetrant is i) a fatty alcohol alkoxylate of the formula (III)

$$R—O-(-AO)_v—R' \quad (III)$$

in which
R is linear or branched alkyl having 4 to 20 carbon atoms,
R' is hydrogen, methyl, ethyl, n-propyl, isopropyl, n-butyl, isobutyl, tert-butyl, n-pentyl or n-hexyl,
AO is an ethylene oxide radical, a propylene oxide radical, a butylene oxide radical or is mixtures of ethylene oxide and propylene oxide radicals or butylene oxide radicals, and
v is a number from 2 to 30,
and/or ii) a mineral or vegetable oil and/or iii) an ester of a mineral or vegetable oil.

11. Composition according to claim 9, wherein the penetrant is an ester of a vegetable oil.

12. Composition according to claim 9, wherein the penetrant is rapeseed oil methyl ester.

13. Composition according to claim 9, wherein the amount of penetrant is 1% to 95% by weight.

14. Method of controlling parasitic insects and/or spider mites, comprising applying a composition according to claim 1, undiluted or diluted to an insect and/or spider mite or a habitat thereof in an amount such that an effective amount of spirotetramat acts on the insect and/or spider mite or said habitat.

15. Method of boosting the activity of spirotetramat comprising applying the composition of claim 1, wherein the composition comprises an application-ready spray liquor.

16. Method according to claim 15, wherein the spray liquor is prepared using a penetrant.

17. Method according to claim 15, wherein the salt of the formula (II) is present in a final concentration of 0.5 to 80 mmol/l.

18. Method according to claim 16, wherein the penetrant is present in a concentration of 0.1 to 10 g/l.

19. Method according to claim 16, wherein the penetrant is present in a concentration of 0.1 to 10 g/l and the salt of the formula (II) in a concentration of 0.5 to 80 mmol/l.

20. A composition for boosting the activity of spirotetramat comprising a composition of claim 1, wherein said composition is in the form of an application-ready spray liquor.

21. A composition according to claim 20, wherein, in the application-ready spray liquor the salt of the formula (II) is present in a concentration of 0.5 to 80 mmol/l.

22. A composition according to claim 20, further comprising a penetrant.

* * * * *